(12) United States Patent
Singh et al.

(10) Patent No.: US 8,883,833 B2
(45) Date of Patent: Nov. 11, 2014

(54) SUBSTITUTED BENZOAZOLE PDE4 INHIBITORS FOR TREATING INFLAMMATORY, CARDIOVASCULAR AND CNS DISORDERS

(75) Inventors: Jasbir Singh, Naperville, IL (US); Mark E. Gurney, Grand Rapids, MI (US); Alex Burgin, Kingston, WA (US); Vincent Sandanayaka, Northboro, MA (US); Alexander Kiselyov, San Diego, CA (US); Munagala Rao, Westmont, IL (US)

(73) Assignee: Decode Genetics EHF (IS)

( * ) Notice: Subject to any disclaimer, the term of this patent is extended or adjusted under 35 U.S.C. 154(b) by 246 days.

(21) Appl. No.: 12/275,165

(22) Filed: Nov. 20, 2008

(65) Prior Publication Data
US 2009/0130077 A1    May 21, 2009

Related U.S. Application Data

(60) Provisional application No. 60/989,557, filed on Nov. 21, 2007.

(51) Int. Cl.
*C07D 513/04* (2006.01)
*C07D 498/04* (2006.01)
(Continued)

(52) U.S. Cl.
CPC ............ *C07D 417/14* (2013.01); *C07D 263/58* (2013.01); *A61K 31/454* (2013.01); *C07D 277/64* (2013.01); *A61K 31/519* (2013.01); *C07D 277/82* (2013.01); *C07D 498/04* (2013.01); *C07D 417/06* (2013.01); *A61K 31/496* (2013.01); *A61K 31/428* (2013.01); *C07D 263/56* (2013.01); *C07D 417/04* (2013.01); *A61K 31/423* (2013.01); *A61K 31/4439* (2013.01); *C07D 513/04* (2013.01)
USPC .................... 514/367; 514/254.02; 514/260.1; 514/321; 514/338; 514/375; 544/255; 544/368; 546/270.1; 546/271.7; 548/164; 548/161; 548/179; 548/180; 548/152; 548/222; 548/217

(58) Field of Classification Search
CPC .. C07D 513/04; C07D 498/04; C07D 417/04; C07D 417/06; C07D 417/14; C07D 277/64; C07D 277/82; C07D 263/56; C07D 263/58; A61K 31/519; A61K 31/496; A61K 31/454; A61K 31/4439; A61K 31/428; A61K 31/423
USPC ......... 514/254.02, 260.1, 321, 338, 367, 375; 544/255, 368; 546/270.1, 271.7; 548/164, 161, 179, 180, 152, 222, 217
See application file for complete search history.

(56) References Cited

U.S. PATENT DOCUMENTS

2003/0130254 A1    7/2003    Marfat et al.
2007/0078136 A1    4/2007    Vaccaro et al.
2008/0045536 A1    2/2008    Vaccaro et al.

FOREIGN PATENT DOCUMENTS

EP            1 095 040 B1    3/2004

OTHER PUBLICATIONS

Houslay et al. Drug Discovery Today 2005, 10, 1503-1517.*

(Continued)

*Primary Examiner* — Joseph Kosack
*Assistant Examiner* — Matthew Coughlin
(74) *Attorney, Agent, or Firm* — Heslin Rothenberg Farley & Mesiti P.C.

(57) ABSTRACT

The invention relates to substituted benzothiazoles, benzoxazoles—and their counterparts having pyridine and pyrimidine rings replacing the benzene ring—that are PDE4 inhibitors useful for treating stroke, myocardial infarct, and cardiovascular inflammatory conditions, to pharmaceutical compositions comprising these compounds, and to methods for the treatment of stroke, myocardial infarct, and cardiovascular inflammatory conditions in a mammal. The compounds have general formula I:

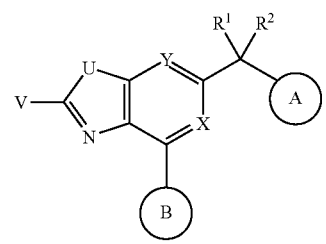

in which A and B are carbocycles or heterocycles. A particular embodiment is

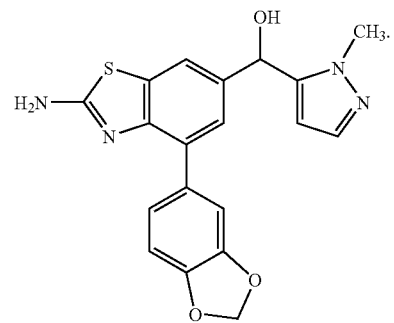

28 Claims, No Drawings

(51) Int. Cl.

| | |
|---|---|
| *C07D 417/04* | (2006.01) |
| *C07D 417/06* | (2006.01) |
| *C07D 417/14* | (2006.01) |
| *C07D 277/64* | (2006.01) |
| *C07D 277/82* | (2006.01) |
| *C07D 263/56* | (2006.01) |
| *C07D 263/58* | (2006.01) |
| *A61K 31/519* | (2006.01) |
| *A61K 31/496* | (2006.01) |
| *A61K 31/454* | (2006.01) |
| *A61K 31/4439* | (2006.01) |
| *A61K 31/428* | (2006.01) |
| *A61K 31/423* | (2006.01) |

(56) References Cited

OTHER PUBLICATIONS

Giron, D. J. Therm. Anal. Cal. 2001, 64, pp. 37-60.*
Giron, D. J. Therm. Anal. Cal. 2002, 68, pp. 335-357.*
B. Rodriquez-Spong et al. Advanced Drug Delivery Reviews, 2004, 56, pp. 241-274.*
Souillac, et al., Characterization of Delivery Systems, Differential Scanning Calorimetry, pp. 217-218 (in Encyclopedia of Controlled Drug Delivery, 1999, John Wiley & Sons, pp. 212-227).*
Berge et al. J. Pharm. Sci. 1997, 66, pp. 1-19.*
Stahl et al. Handbook of Pharmaceutical Salts, Wiley & Sons, 2008, p. 1-7.*
Serajuddin, Advanced Drug Delivery Reviews 2007, 59, 603-616.*
Schultheiss et al. (Crystal Growth & Design 2009, 9, 2950-2967).*
MPEP 1490, Section V, pp. 1400-105 through 1400-107, Aug. 5, 2006.*
Hocek, et al, Synthesis of carba-analogues of myoseverin by regioselective cross-coupling reactions of 2,6-dichloro-9-isopropylpurine, Tetrahedron (2003), 59(5), 607-611.
International Search Report for PCT/US2008/084199, Feb. 25, 2009.
International Search Report for PCT/US2008/084225, Feb. 25, 2009.
Shiota et al., Regioselective Reactions of Organozinc Reagents with 2,4-Dichloroquinoline and 5,7-Dichloropyrazolo[1,5-a]pyrimidine, Journal of Organic Chemistry (1999), 64(2), pp. 453-457.

* cited by examiner

SUBSTITUTED BENZOAZOLE PDE4 INHIBITORS FOR TREATING INFLAMMATORY, CARDIOVASCULAR AND CNS DISORDERS

CROSS-REFERENCE TO RELATED APPLICATIONS

This application claims priority from U.S. provisional application 60/989,557, filed Nov. 21, 2007, the entire disclosure of which is incorporated herein by reference. The application is related to, but does not claim priority from, four other US non-provisional applications filed of even date herewith and having Jasbir Singh as a common inventor. The applications are titled "BIARYL PDE4 INHIBITORS FOR TREATING INFLAMMATORY, CARDIOVASCULAR AND CNS DISORDERS", "BIARYL PDE4 INHIBITORS FOR TREATING PULMONARY AND CARDIOVASCULAR DISORDERS", "SUBSTITUTED BENZOAZOLE PDE4 INHIBITORS FOR TREATING PULMONARY AND CARDIOVASCULAR DISORDERS" and "4-(OR 5-) SUBSTITUTED CATECHOL DERIVATIVES". Their disclosures are incorporated herein by reference.

FIELD OF THE INVENTION

The invention relates to substituted benzothiazoles, benzoxazoles—and their counterparts having pyridine and pyrimidine rings replacing the benzene ring—that are useful for treating stroke, myocardial infarct, and cardiovascular inflammatory conditions, to pharmaceutical compositions comprising these compounds, and to methods for the treatment of stroke, myocardial infarct, and cardiovascular inflammatory conditions in a mammal.

BACKGROUND OF THE INVENTION

PDE4 is the major cAMP-metabolizing enzyme found in inflammatory and immune cells. PDE4 inhibitors have proven potential as anti-inflammatory drugs, especially in inflammatory pulmonary diseases such as asthma, COPD and rhinitis. They suppress the release of cytokines and other inflammatory signals and inhibit the production of reactive oxygen species. A large number of PDE4 inhibitors have been developed for a variety of clinical indications (Torphy and Page. 2000. TIPS 21, 157-159; Burnouf and Pruniaux. 2002. Curr. Pharm. Design 8, 1255-1296; Lipworth. 2005. Lancet 365, 167-175). To quote from a recent article in the British Journal of Pharmacology, "PDE4 inhibitors have been in development as a novel anti-inflammatory therapy since the 1980s with asthma and chronic obstructive pulmonary disease (COPD) being primary indications. Despite initial optimism, none have yet reached the market. In most cases, the development of PDE4 inhibitors of various structural classes, including cilomilast, filaminast, lirimilast, piclamilast, tofimilast . . . has been discontinued due to lack of efficacy. A primary problem is the low therapeutic ratio of these compounds, which severely limits the dose that can be given. Indeed, for many of these compounds it is likely that the maximum tolerated dose is either sub-therapeutic or at the very bottom of the efficacy dose-response curve. Therefore, the challenge is to overcome this limitation." [Giembycz, Brit. J. Pharmacol. 155, 288-290 (2008)]. Many of the PDE4 inhibitors of the prior art have not reached the market because of the adverse side effect of emesis (Giembycz 2005. Curr. Opin. Pharm. 5, 238-244). Analysis of all known PDE4 inhibitors suggests that they are competitive with cAMP and bind within the active site (Houslay et al. 2005. DDT 10, 1503-1519); this may explain their narrow therapeutic ratio. The compounds of the present invention are non-competitive inhibitors of cAMP while being gene-specific inhibitors (PDE4D), and, based on the target rationale and in vitro potency, a person of skill in the art would expect the compounds to be useful as anti-inflammatory agents for the treatment, amelioration or prevention of inflammatory diseases and of complications arising therefrom and useful as CNS agents for amelioration of the cognitive decline in Alzheimer's disease, Parkinson's disease, the treatment of schizophrenia and depression, and neuroprotective in Huntington's disease.

SUMMARY OF THE INVENTION

The present invention relates to compounds exhibiting PDE4 enzyme inhibition, having the general formula I

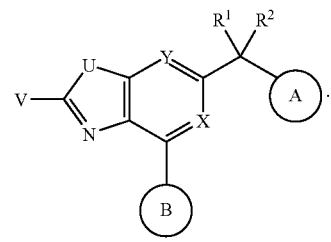

In these compounds
U is selected from the group consisting of —S— and —O—;
V is selected from the group consisting of H, $CH_3$, $NH_2$, and $CF_3$;
X is selected from the group consisting of CH, C—F, C—Cl, C—Br, C—I, C—$NH_2$, C—OH, C—$OCH_3$, N, and N—O;
Y is selected from the group consisting of N, CH, CF and C-lower alkyl;
$R^1$ is H or lower alkyl;
$R^2$ is selected from the group consisting of H, alkyl, OH, $NH_2$, and $OCH_3$;
B is an optionally substituted, mono- or bicyclic aryl or heteroaryl; and
A is an optionally substituted heterocycle or an optionally substituted carbocycle.

There is also provided, in accordance with embodiments of the invention, a pharmaceutical composition comprising a compound as described herein, and a pharmaceutically acceptable carrier, excipient or diluent therefore. When the compound is present as a salt, the salt should be a pharmaceutically acceptable salt.

In a third aspect, the invention relates to methods for the treatment or prophylaxis of a disease or condition mediated by phosphodiesterase-4. The methods comprise administering to a mammal a therapeutically effective amount of a compound having the general formula I. The disease or condition may be related to allergic, acute or chronic inflammation. The disease may be, for example, atherosclerosis, thrombosis, stroke, acute coronary syndrome, stable angina, peripheral vascular disease, critical leg ischemia, intermittent claudication, abdominal aortic aneurysm or myocardial infarction.

Selective PDE4 inhibitors of the invention may be useful in improving cognition and thus useful for treating learning disorders, memory loss and other cognitive dysfunctions. Selective PDE4 inhibitors of the invention are also useful for treating asthma and Chronic Obstructive Pulmonary Disease (COPD). Compounds of the invention, which inhibit tumor growth and metastases, also find utility in the treatment and prevention of cancer, including esophageal cancer, brain cancer, pancreatic cancer, and colon cancer.

These and other embodiments of the present invention will become apparent in conjunction with the description and claims that follow.

DETAILED DESCRIPTION OF THE INVENTION

Throughout this specification the substituents are defined when introduced and retain their definitions.

Unless otherwise specified, alkyl is intended to include linear, branched, or cyclic hydrocarbon structures and combinations thereof. A combination would be, for example, cyclopropylmethyl. Lower alkyl refers to alkyl groups of from 1 to 6 carbon atoms. Examples of lower alkyl groups include methyl, ethyl, propyl, isopropyl, butyl, s- and t-butyl and the like. Preferred alkyl groups are those of $C_{20}$ or below; $C_1$ to $C_8$ are more preferred. Cycloalkyl is a subset of alkyl and includes cyclic hydrocarbon groups of from 3 to 8 carbon atoms. Examples of cycloalkyl groups include c-propyl, c-butyl, c-pentyl, norbornyl and the like.

$C_1$ to $C_{20}$ hydrocarbon includes alkyl, cycloalkyl, polycycloalkyl, alkenyl, alkynyl, aryl and combinations thereof. Examples include benzyl, phenethyl, cyclohexylmethyl, camphoryl and naphthylethyl. Hydrocarbon refers to any substituent comprised of hydrogen and carbon as the only elemental constituents.

Unless otherwise specified, the term "carbocycle" is intended to include ring systems in which the ring atoms are all carbon but of any oxidation state. Thus ($C_3$-$C_{10}$) carbocycle refers to both non-aromatic and aromatic systems, including such systems as cyclopropane, benzene, cyclopentene and cyclohexene; ($C_8$-$C_{12}$) carbopolycycle refers to such systems as norbornane, decalin, indane and naphthalene. Carbocycle, if not otherwise limited, refers to monocycles, bicycles and polycycles.

Alkoxy or alkoxyl refers to groups of from 1 to 8 carbon atoms of a straight, branched or cyclic configuration and combinations thereof attached to the parent structure through an oxygen. Examples include methoxy, ethoxy, propoxy, isopropoxy, cyclopropyloxy, cyclohexyloxy and the like. Lower-alkoxy refers to groups containing one to four carbons. For the purpose of this application, alkoxy and lower alkoxy include methylenedioxy and ethylenedioxy. Alkoxyalkyl refers to ether groups of from 3 to 8 atoms of a straight, branched, cyclic configuration and combinations thereof attached to the parent structure through an alkyl. Examples include methoxymethyl, methoxyethyl, ethoxypropyl, and the like. Alkoxyaryl refers to alkoxy substituents attached to an aryl, wherein the aryl is attached to the parent structure. Arylalkoxy refers to aryl substituents attached to an oxygen, wherein the oxygen is attached to the parent structure. Substituted arylalkoxy refers to a substituted aryl substituent attached to an oxygen, wherein the oxygen is attached to the parent structure.

Oxaalkyl refers to alkyl residues in which one or more carbons (and their associated hydrogens) have been replaced by oxygen. Examples include methoxypropoxy; 3,6,9-trioxadecyl; 2,6,7-trioxabicyclo[2.2.2]octane and the like. The term oxaalkyl is intended as it is understood in the art [see Naming and Indexing of Chemical Substances for Chemical Abstracts, published by the American Chemical Society, 196, but without the restriction of 127(a)], i.e. it refers to compounds in which the oxygen is bonded via a single bond to its adjacent atoms (forming ether bonds); it does not refer to doubly bonded oxygen, as would be found in carbonyl groups. Similarly, thiaalkyl and azaalkyl refer to alkyl residues in which one or more carbons has been replaced by sulfur or nitrogen, respectively. Examples include ethylaminoethyl and methylthiopropyl.

Unless otherwise specified, acyl refers to formyl and to groups of 1, 2, 3, 4, 5, 6, 7 and 8 carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, benzyloxycarbonyl and the like. Lower-acyl refers to groups containing one to four carbons. The double bonded oxygen, when referred to as a substituent itself is called "oxo".

Aryl and heteroaryl mean (i) a phenyl group (or benzene) or a monocyclic 5- or 6-membered heteroaromatic ring containing 1-4 heteroatoms selected from O, N, or S; (ii) a bicyclic 9- or 10-membered aromatic or heteroaromatic ring system containing 0-4 heteroatoms selected from O, N, or S; or (iii) a tricyclic 13- or 14-membered aromatic or heteroaromatic ring system containing 0-5 heteroatoms selected from O, N, or S. Aryl, as understood herein, includes residues in which one or more rings are aromatic, but not all need be. Thus aromatic 6- to 14-membered carbocyclic rings include, e.g., benzene, naphthalene, indane, tetralin, and fluorene and the 5- to 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole.

Arylalkyl refers to a substituent in which an aryl residue is attached to the parent structure through alkyl. Examples are benzyl, phenethyl and the like. Heteroarylalkyl refers to a substituent in which a heteroaryl residue is attached to the parent structure through alkyl. In one embodiment, the alkyl group of an arylalkyl or a heteroarylalkyl is an alkyl group of from 1 to 6 carbons. Examples include, e.g., pyridinylmethyl, pyrimidinylethyl and the like.

Heterocycle means a cycloalkyl or aryl carbocycle residue in which from one to three carbons is replaced by a heteroatom selected from the group consisting of N, O and S. The nitrogen and sulfur heteroatoms may optionally be oxidized, and the nitrogen heteroatom may optionally be quaternized. Unless otherwise specified, a heterocycle may be non-aromatic or aromatic. It is to be noted that heteroaryl is a subset of heterocycle in which the heterocycle is aromatic. Examples of heterocyclic residues that fall within the scope of the invention include pyrazole, pyrrole, indole, quinoline, isoquinoline, tetrahydroisoquinoline, benzofuran, benzodioxan, benzodioxole (commonly referred to as methylenedioxyphenyl, when occurring as a substituent), morpholine, thiazole, pyridine (including 2-oxopyridine), pyridine N-oxide, pyrimidine, thiophene (i.e. thiene), furan, oxazole, oxazoline, oxazolidine, isoxazolidine, isoxazole, dioxane, azetidine, piperazine, piperidine, pyrrolidine, pyridazine, azepine, pyrazolidine, imidazole, imidazoline, imidazolidine, imidazolopyridine, pyrazine, thiazolidine, isothiazole, 1,2-thiazine-1,1-dioxide, quinuclidine, isothiazolidine, benzimidazole, thiadiazole, benzopyran, benzothiazole, benzotriazole, benzoxazole, tetrahydrofuran, tetrahydropyran, benzothiene, thiamorpholine, thiamorpholine sulfoxide, thiamorpholine sulfone, oxadiazole, triazole, tetrazole, isatin (dioxoindole), phthalimide (dioxoisoindole), pyrrolopyridine, triazolopyridine and the dihydro and tetrahydro congeners of the fully unsaturated ring systems among the foregoing.

An oxygen heterocycle is a heterocycle containing at least one oxygen in the ring; it may contain additional oxygens, as well as other heteroatoms. Oxygen heterocycles found in the examples of the invention include tetrahydrofuran, benzodioxole, morpholine, isoxazole and 2,6,7-trioxabicyclo[2.2.2]octane. A sulphur heterocycle is a heterocycle containing at least one sulphur in the ring; it may contain additional sulphurs, as well as other heteroatoms. A nitrogen heterocycle is a heterocycle containing at least one nitrogen in the ring; it may contain additional nitrogens, as well as other heteroatoms.

As used herein, the term "optionally substituted" may be used interchangeably with "unsubstituted or substituted". The term "substituted" refers to the replacement of one or more hydrogen atoms in a specified group with a specified radical. For example, substituted alkyl, aryl, cycloalkyl, heterocyclyl etc. refer to alkyl, aryl, cycloalkyl, or heterocyclyl wherein up to three H atoms in each residue are replaced with halogen, haloalkyl, alkyl, acyl, alkoxyalkyl, hydroxyalkyl, carbonyl (i.e. oxo), phenyl, heteroaryl, benzenesulfonyl, hydroxy, alkoxy, haloalkoxy, oxaalkyl, carboxy, alkoxycarbonyl [—C(=O)O-alkyl], alkoxycarbonylamino [—NHC(=O)O-alkyl], alkoxycarbonylaminoalkyl [-alkyl-NHC(=O)O-alkyl], carboxyalkylcarbonylamino [—NHC(=O)-alkyl-COOH], carboxamido [—C(=O)NH$_2$], aminocarbonyloxy [—OC(=O)NH$_2$], alkylaminocarbonyl [—C(=O)NH-alkyl], dialkylaminocarbonyl [—C(=O)N(alkyl)$_2$], aminocarbonylalkyl [-alkyl-C(=O)NH$_2$], cyano, acetoxy, nitro, amino, alkylamino, dialkylamino, aminoalkyl, (alkyl)(aryl)aminoalkyl, alkylaminoalkyl (including cycloalkylaminoalkyl), dialkylaminoalkyl, dialkylaminoalkoxy, alkyl(hydroxyalkyl)amino, heterocyclylalkoxy, mercapto, alkylthio, alkylsulfonyl, alkylsulfonylamino, alkylsulfinyl, alkylsulfonyl, arylthio, arylsulfonyl, arylsulfonylamino, arylsulfinyl, arylsulfonyl, acylaminoalkyl, acylaminoalkoxy, acylamino, amidino, aryl, benzyl, heterocyclyl, heterocyclylalkyl, phenoxy, benzyloxy, heteroaryloxy, heterocyclylamino, hydroxyimino, alkoxyimino, oxaalkyl, aminosulfonyl, trityl, amidino, guanidino, ureido, —NHC(=O)NHalkyl, —NHC(=O)NH-heterocyclyl, -alkyl-NHC(=O)N(alkyl)$_2$, heterocyclylalkylcarbonylamino, benzyloxyphenyl, and benzyloxy. Although oxo is included among the substituents referred to in "optionally substituted", it will be appreciated by persons of skill in the art that, because oxo is a divalent radical, there are circumstances in which it will not be appropriate as a substituent (e.g. on phenyl). Additional substituents that are considered within the scope of the term, particularly for R$^1$, are the are the residues of amino acids, amino acid amides, protected residues of aminoacids and their amides, and N-methylated (mono- or di-, as appropriate) amino acids and amino acid amides.

For the purpose of ring A or A$^1$, the substituents alkyl, acyl, alkoxyalkyl, hydroxyloweralkyl, phenyl, heteroaryl, benzenesulfonyl, loweralkoxy, haloalkoxy, oxaalkyl, alkoxycarbonyl, alkoxycarbonylamino, carboxamido, alkylaminocarbonyl, amino, alkylamino, (alkyl)(aryl)aminoalkyl, alkylaminoalkyl, heterocyclylalkoxy, alkylthio, sulfonylamino, alkylsulfinyl, alkylsulfonyl, acylaminoalkyl, acylaminoalkoxy, acylamino, amidino, aryl, benzyl, heterocyclyl, heterocyclylalkyl, heterocyclylalkoxy, phenoxy, benzyloxy, heteroaryloxy, heterocyclylamino, oxaalkyl, aminosulfonyl, amidino, guanidino, ureido, benzyloxyphenyl, and benzyloxy may be further substituted with one or two substituents from the list of substituents above. Substituents that are considered within the scope of the term, particularly for A, are the are the residues of amino acids, amino acid amides and protected residues of aminoacids and their amides, as well as the following specific residues: —CH$_3$, —CH$_2$CF$_3$, —CF$_3$, —CHO, —COOH, —CN, halogen, —OH, —OEt, —C(=O)NH$_2$, —C(=O)NHEt, —C(=O)NMe$_2$-COOCH$_3$, —COOEt, —CH$_2$NHC(=O)NH$_2$, —CH(CH$_3$)NHC(=O)NH$_2$, —CH$_2$NHC(=O)H, —CH$_2$NHC(=O)CH$_3$, —CH$_2$C(=O)NH$_2$, —CH$_2$COOH, —CH$_2$COOEt, —CH$_2$NHC(=O)OEt, —CH$_2$NHC(=O)O—C$_6$H$_5$, —CH$_2$NHC(=O)C(=O)NH$_2$, —CH$_2$NHC(=O)NHEt, —C(CH$_3$)$_2$OH, —CH$_2$NHC(=O)N(CH$_3$)$_2$, —CH$_2$NHC(=O)NHCH$_3$, —CH$_2$NH$_2$, —CH(CH$_3$)NH$_2$, —C(CH$_3$)$_2$NH$_2$, —CH$_2$OH, —CH$_2$CH$_2$OH, —CH$_2$NHSO$_2$CH$_3$, —CH$_2$C(=O)NHEt, —OCH$_3$, —OC(=O)NH$_2$, —OCH$_2$CH$_2$N(CH$_3$)$_2$, —OCH$_2$CH$_2$OCH$_3$, —NHC(=O)NH$_2$, —NHC(=O)NHEt, —NHCH$_3$, —NHEt, —NH(tBoc), —NHCH$_2$COOH ("residue of glycine"), —N(CH$_3$)CH$_2$COOH ("residue of N-methylglycine"), —NHC(=O)NHCH$_2$CH$_2$Cl, —NHSO$_2$NH$_2$, —NHEt, —N(CH$_3$)$_2$, —NH$_2$, —NH(CH$_3$)C(=O)NH$_2$, —NHSO$_2$CH$_3$, —N(SO$_2$CH$_3$)$_2$, —NHC(=O)OCH$_3$, —NHC(=O)OtBu, —NHC(=O)CH$_3$, —SO$_2$NH$_2$, —NHC(=O)CH$_2$CH$_2$COOH, —NHC(=O)NHCH$_2$COOH, —CH$_2$NHCHO, —NHC(=O)NHCH$_2$COOEt, —NHC(=O)NH(CH$_2$)$_3$COOEt, —NHC(=O)NH(CH$_2$)$_2$COOEt, —N(CH$_3$)CH$_2$CH$_2$OH, —NHC(=O)OEt, —N(Et)C(=O)OEt, —NHC(=O)NH(CH$_2$)$_2$COOH, —NHC(=O)CH$_2$N(CH$_3$)$_2$, —NHC(=O)NH(CH$_2$)$_3$COOH, —NHC(=O)CH$_2$NH$_2$, —NHC(=O)CH$_2$CH$_2$NH$_2$, —NHC(=O)CH$_2$NH(tBoc),

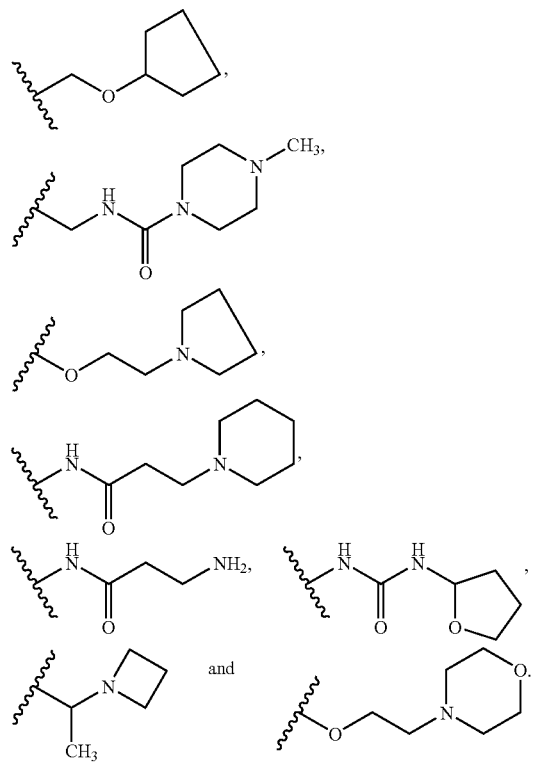

The term "a residue of an amino acid, amino acid amide", etc. refers to an amino acid etc. minus the functional groups that are considered part of the bond to the parent structure. For example, in the molecule BA-64 illustrated below:

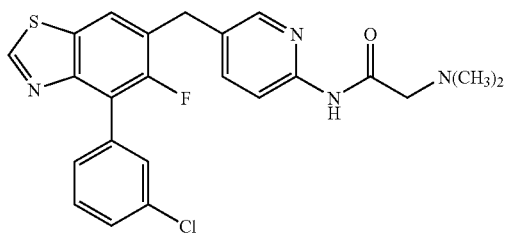

BA-64 after one subtracts the hydrogen that connects N,N-dimethylglycinamide to the phenyl ring, the structure of A that remains is:

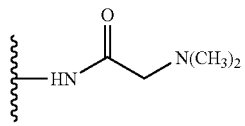

This is not sensu stricto an N-methylamino acid amide, since it lacks the hydrogen on the C-terminal amide. This and similar structures that lack atoms at the points of attachment (e.g. the OH of COOH or the H of $NH_2$) are referred to herein as "residues" of their respective parents.

The terms "haloalkyl" and "haloalkoxy" mean alkyl or alkoxy, respectively, substituted with one or more halogen atoms. The terms "alkylcarbonyl" and "alkoxycarbonyl" mean —C(=O)alkyl or —C(O)alkoxy, respectively.

The term "halogen" means fluorine, chlorine, bromine or iodine. In one embodiment, halogen may be fluorine or chlorine.

Substituents R″ are generally defined when introduced and retain that definition throughout the specification and in all independent claims.

In the characterization of some of the substituents, it is recited that certain substituents may combine to form rings. Unless stated otherwise, it is intended that such rings may exhibit various degrees of unsaturation (from fully saturated to fully unsaturated), may include heteroatoms and may be substituted with lower alkyl or alkoxy.

It will be recognized that the compounds of this invention can exist in radiolabeled form, i.e., the compounds may contain one or more atoms containing an atomic mass or mass number different from the atomic mass or mass number usually found in nature. Radioisotopes of hydrogen, carbon, phosphorous, fluorine, and chlorine include $^2H$, $^3H$, $^{13}C$, $^{14}C$, $^{15}N$, $^{35}S$, $^{18}F$, and $^{36}Cl$, respectively. Compounds that contain those radioisotopes and/or other radioisotopes of other atoms are within the scope of this invention. Tritiated, i.e. $^3H$, and carbon-14, i.e., $^{14}C$, radioisotopes are particularly preferred for their ease in preparation and detectability. Compounds that contain isotopes $^{11}C$, $^{13}N$, $^{15}O$ and $^{18}F$ are well suited for positron emission tomography. Radiolabeled compounds of formula I of this invention and prodrugs thereof can generally be prepared by methods well known to those skilled in the art. Conveniently, such radiolabeled compounds can be prepared by carrying out the procedures disclosed in the Examples and Schemes by substituting a readily available radiolabeled reagent for a non-radiolabeled reagent.

As used herein (particularly in the claims), and as would be understood by the person of skill in the art, the recitation of "a compound" is intended to include salts, solvates, cocrystals and inclusion complexes of that compound as well as any stereoisomeric form, or a mixture of any such forms of that compound in any ratio. Thus, in accordance with some embodiments of the invention, a compound as described herein, including in the contexts of pharmaceutical compositions, methods of treatment, and compounds per se, is provided as the salt form. Thus, for example, the recitation "a compound of formula I" as depicted above, in which R1 is imidazolyl, would include imidazolium salts. In a particular embodiment, the term "compound of formula I" refers to the compound or a pharmaceutically acceptable salt thereof.

The compounds described herein may contain asymmetric centers and may thus give rise to enantiomers, diastereomers, and other stereoisomeric forms. Each chiral center may be defined, in terms of absolute stereochemistry, as (R)— or (S)—. The present invention is meant to include all such possible isomers, in any ratio from racemic to optically pure forms. Optically active (R)— and (S)-isomers may be prepared using chiral synthons or chiral reagents, or resolved using conventional techniques. The prefix "rac" refers to a racemate. When the compounds described herein contain olefinic double bonds or other centers of geometric asymmetry, and unless specified otherwise, it is intended that the compounds include both E and Z geometric isomers. The representation of the configuration of any carbon-carbon double bond appearing herein is selected for convenience only, and unless explicitly stated, is not intended to designate a particular configuration. Thus a carbon-carbon double bond depicted arbitrarily as E may be Z, E, or a mixture of the two in any proportion. Likewise, all tautomeric forms are also intended to be included.

The term "solvate" refers to a compound of Formula I in the solid state, wherein molecules of a suitable solvent are incorporated in the crystal lattice. A suitable solvent for therapeutic administration is physiologically tolerable at the dosage administered. Examples of suitable solvents for therapeutic administration are ethanol and water. When water is the solvent, the solvate is referred to as a hydrate. In general, solvates are formed by dissolving the compound in the appropriate solvent and isolating the solvate by cooling or using an antisolvent. The solvate is typically dried or azeotroped under ambient conditions. Inclusion complexes are described in *Remington: The Science and Practice of Pharmacy* 19th Ed. (1995) volume 1, page 176-177, which is incorporated herein by reference. The most commonly employed inclusion complexes are those with cyclodextrins, and all cyclodextrin complexes, natural and synthetic, are specifically encompassed within the claims.

The term "pharmaceutically acceptable salt" refers to salts prepared from pharmaceutically acceptable non-toxic acids or bases including inorganic acids and bases and organic acids and bases. When the compounds of the present invention are basic, salts may be prepared from pharmaceutically acceptable non-toxic acids including inorganic and organic acids. Suitable pharmaceutically acceptable anions for the compounds of the present invention include acetate, benzenesulfonate (besylate), benzoate, bicarbonate, bisulfate, carbonate, camphorsulfonate, citrate, ethanesulfonate, fumarate, gluconate, glutamate, glycolate, bromide, chloride, isethionate, lactate, maleate, malate, mandelate, methanesulfonate, mucate, nitrate, pamoate, pantothenate, phosphate, succinate, sulfate, tartrate, trifluoroacetate, p-toluenesulfonate, acetamidobenzoate, adipate, alginate, aminosalicylate, anhydromethylenecitrate, ascorbate, aspartate, calcium edetate, camphorate, camsylate, caprate, caproate, capiylate, cinnamate, cyclamate, dichloroacetate, edetate (EDTA), edisylate, embonate, estolate, esylate, fluoride, formate, gentisate, gluceptate, glucuronate, glycerophosphate, glycolate, glycollylarsanilate, hexylresorcinate, hippurate, hydroxynaphthoate, iodide, lactobionate, malonate, mesylate, napadisylate, napsylate, nicotinate, oleate, orotate, oxalate, oxoglutarate, palmitate, pectinate, pectinate polymer, phenylethylbarbiturate, picrate, pidolate, propionate, rhodanide, salicylate, sebacate, stearate, tannate, theoclate, tosylate and the like. The desired salt may be obtained by ion exchange of whatever counter ion is obtained in the synthesis of the quat. These methods are well known to persons of skill. Although pharmaceutically acceptable counter ions will be preferred for preparing pharmaceutical formulations, other anions are quite acceptable as synthetic intermediates. When the compounds contain an acidic side chain, suitable pharmaceutically acceptable base addition salts for the compounds of the present invention include metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine.

The graphic representations of racemic, ambiscalemic and scalemic or enantiomerically pure compounds used herein are taken from Maehr J. Chem. Ed. 62, 114-120 (1985): solid and broken wedges are used to denote the absolute configuration of a chiral element; wavy lines and single thin lines indicate disavowal of any stereochemical implication which the bond it represents could generate; solid and broken bold lines are geometric descriptors indicating the relative configuration shown but denoting racemic character; and wedge outlines and dotted or broken lines denote enantiomerically pure compounds of indeterminate absolute configuration.

Terminology related to "protecting", "deprotecting" and "protected" functionalities occurs throughout this application. Such terminology is well understood by persons of skill in the art and is used in the context of processes that involve sequential treatment with a series of reagents. In that context, a protecting group refers to a group, which is used to mask a functionality during a process step in which it would otherwise react, but in which reaction is undesirable. The protecting group prevents reaction at that step, but may be subsequently removed to expose the original functionality. The removal or "deprotection" occurs after the completion of the reaction or reactions in which the functionality would interfere. Thus, when a sequence of reagents is specified, as it is in the processes of the invention, the person of ordinary skill can readily envision those groups that would be suitable as "protecting groups". Suitable groups for that purpose are discussed in standard textbooks in the field of chemistry, such as Protective Groups in Organic Synthesis by T. W. Greene [John Wiley & Sons, New York, 1991], which is incorporated herein by reference.

A comprehensive list of abbreviations utilized by organic chemists appears in the first issue of each volume of the Journal of Organic Chemistry. The list, which is typically presented in a table entitled "Standard List of Abbreviations", is incorporated herein by reference.

In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants that are in themselves known, but are not mentioned here. The starting materials, are either commercially available, synthesized as described in the examples or may be obtained by the methods well known to persons of skill in the art.

PDE4 inhibitors have been shown to be effective therapeutic agents in clinical studies. For example, administration of cilomilast and roflumilast (PDE4 inhibitors) to patients suffering from asthma and COPD showed initially excellent results, although the effect of cilomilast disappeared on longterm trial [Lipworth, *Lancet* 365, 167-175 (2005)]. Genetic studies have clearly demonstrated an association between PDE4D and ischemic stroke (Gretarsdottir et al. 2003. Nature Genetics. 35, 1-8). L-454,560, a selective PDE4 inhibitor has been shown to improve learning in a rat model in vivo [Huang et al. *Biochemical Pharmacology* 73, 1971-1981 (2007)]. This suggests that selective PDE4 inhibitors will be useful in treating learning disorders, memory loss (e.g. Alzheimer's disease) and other cognitive dysfunctions. Rolipram, another selective PDE4 inhibitor, has been shown to enhance cognition in multiple rodent models [Blokland et al., Current Pharmaceutical Design 12, 2511-2523 (2006)] as well as in primates [Rutten et al., 2008, Psychopharmacology 196, 643-648 (2008)]. Rolipram also improves the outcome in two separate studies in mice in vivo in models accepted by persons of skill in the art as predictive of utility in schizophrenia [Kanes et al., *Neuroscience* 144, 239-246 (2007); Davis and Gould, *Behav. Neurosci.* 119, 595-602 (2005)]. Rolipram has also been shown to exhibit a neuroprotective effect in a rat model of Huntington's disease [DeMarch et al. Neurobiol. Dis. 25, 266-273 (2007)]. This suggests that PDE4 modulators will be useful for treating many CNS disorders. Selective PDE4 inhibitors (e.g. rolipram) are also useful for treating bone loss [Yao et al., *J. Musculoskelet. Neuronal Interact.* 7, 119-130 (2007)].

Additionally, a PDE4 inhibitor, YM976, was shown to ameliorate the effects of experimentally-induced interstitial cystitis in rats, resulting in a decrease in the frequency of urination and an increase in the volume of urine at each time of urination [Kitta et al., *BJU Int.* 102, 1472-1476 (2008)]. Another PDE4 inhibitor, IC485, was shown to be equally efficacious as tolteradine tartrate, a marketed drug for treating overactive bladder, in a rodent model of obstructive bladder [Kaiho et al. BJU Int. 101, 615-20 (2008)]. These findings suggest that PDE4 inhibitors will be useful in treating symptoms of bladder overactivity, inflammation and pain.

In addition to the foregoing studies demonstrating utility in in vivo models, a number of authors have suggested connections between PDE4 inhibition and putative utilities as antidepressants [Houslay et al., Drug Discov Today 10, 1503-1519 (2005); Polesskaya et al., Biol. Psychiatr. 61, 56-64 (2007); anon. Current Opin. Invetig. Drugs 5, 34-39 (2004)] and as anxiolytics [Zhang et al., *Neuropsychopharmacology* Aug. 15, 2007 Epub; Cherry et al., *Biochim. Biophys. Acta* 1518, 27-35 (2001)]. Rolipram has been shown in human clinical trials to ameliorate depression [Hebenstreit et al., Pharmacopsychiat. 22, 156-160 (1989)]. Other possible utilities may include Pick's disease and epilepsy.

Furthermore, the compounds, compositions and methods of the present invention may be useful in treating cancer. Phosphodiesterase activity has been shown to be associated with hematological malignancies [Lerner et al., *Biochem. J.* 393, 21-41 (2006); Ogawa et al., *Blood* 99, 3390-3397 (2002)]. The compounds may also be administered to overcome cognitive impairment induced by one or more of the following agents, alcohol, amphetamine, antipsychotic medication, anti-retroviral therapy, MDMA (3,4-methylenedioxy-N-methylamphetamine, cannabis, cocaine, delta-9 tetrahydrocannabinol, dexamphetamine, haloperidol, heroin and other opiates, ketamine and metamphetamine.

Furthermore, the compounds, compositions and methods of the present invention, particularly when radiolabeled as described above or labeled by methods well-known in the art with florescent and spin labels, may be employed as imaging agents and in other ways for diagnosis and/or treatment. Moreover, immobilization of compounds of the invention on solid support could be of utility for affinity purification and modification of compounds of the invention with chemically active groups may be used for protein labeling.

For many of the utilities outlined above, it may be advantageous to administer compounds of the general formula I together with cholinesterase inhibitors (e.g. tacrine, huperzine, donepezil); NMDA antagonists (e.g. lanicemine, remacemide, neramexane, memantine); calpain inhibitors (e.g. CEP-3122); antioxidants (e.g. vitamin E, coenzyme Q10) and agents that have shown clinical efficacy but whose mechanism is unclear (e.g. dimebon). Compounds of formula I may also be administered together with one or more of the following agents to improve cognition: amisulpride, atomoxetine, bromocryptine, buspirone, caffeine, chlorpromazihe, clonidine, clozapine, diazepam, flumazenil, fluoxetine, galantamine, guanfacine, methylphenidate, idazoxan, modafinil, olanzapine, paroxetine, pergolide, phenserine, quetiapine, risperidone, rivastigmine, SGS742 and sulpiride.

The terms "methods of treating or preventing" mean amelioration, prevention or relief from the symptoms and/or effects associated with disorders. The term "preventing" as used herein refers to administering a medicament beforehand to forestall or obtund an acute episode. The person of ordinary skill in the medical art (to which the present method claims are directed) recognizes that the term "prevent" is not an absolute term. In the medical art it is understood to refer to the prophylactic administration of a drug to substantially diminish the likelihood or seriousness of a condition, and this is the sense intended in applicants' claims. As used herein, reference to "treatment" of a patient is intended to include prophylaxis.

The term "mammal" is used in its dictionary sense. Humans are included in the group of mammals, and humans would be the preferred subjects of the methods.

The cognitive impairment to be treated may arise from one or more of the following disorders, which may not in themselves be necessarily associated with PDE4 abnormality: acute pain, AD/HD—Attention deficit hyperactivity disorder, AIDS dementia complex, alcoholism, amphetamine addiction, amygdalo-hippocampectomy, anorexia nervosa, anterior parietal damage, antisocial behavior, antisocial personality disorder, anxiety, autism, basal ganglia lesions, bipolar disorder, borderline personality disorder, camptocormia, capgras syndrome, carcinoid syndrome, carotid endarterectomy surgery, chronic drug misuse, chronic fatigue syndrome, chronic occupational solvent encephalopathy, chronic pain, brain ischemia, coronary artery bypass surgery, critical illness requiring intensive care, dementia Alzheimer-type (DAT), dementia Lewy Body type, dementia of frontal type, dementia caused by ischemia, dental pain, developmental dyslexia, diabetes, dorsolateral frontal cortical compression, Down's Syndrome, drug abuse, dysexecutive syndrome, fibromyalgia, frontal lobe damage, frontal lobe excision, frontal variant frontotemporal dementia, gluten ataxia, hallucinosis, head injury, hearing loss, heart disease, heart failure, heavy social drinking, hepatic encephalopathy, heroin addiction, herpes encephalitis, hippocampal atrophy, HIV/AIDS, Huntington's disease, hydrocephalus, hypercortisolemia, hyperostosis frontalis interna, hypertension, idiopathic pain, insomnia, Korsakoff syndrome, late paraphrenia, lead exposure, left ventricular systolic dysfunction, orbitofrontal cortex lesion, liver failure, long term health effects of diving, Machado-Joseph disease, mad hatter's disease, manic depression, melancholia, mercury poisoning, mild cognitive impairment (MCI), mild cognitive impairment (MCI) of aging, motor neuron disease, multiple sclerosis, multiple system atrophy, narcolepsy, neuronal migration disorders, normal pressure hydrocephalus, obsessive compulsive disorder, organophosphate pesticide exposure, panic disorder, paraphrenia, Parkinson's disease, periventricular brain insult, personality disorder, gasoline sniffing, phenylketonuria, postconcussion syndrome, premature birth needing intensive care, premenstrual dysphoric disorder, progressive supranuclear palsy, psychopathy, psychosis, questionable dementia, renal cancer, Roifman syndrome, schizoaffective disorder, schizophrenia, seasonal affective disorder, self harm, semantic dementia, specific language impairment, social withdrawal in schizophrenia, solvent encephalopathy, spina bifida, Steele-Richardson-Olzsewski syndrome, stiff person syndrome, striatocapsular infarct, subarachnoid hemorrhage, substance abuse, tardive dyskinesia, temporal lobe excision, temporal lobe lesion, tinnitus, Tourette's syndrome, transient cerebral ischemia, traumatic brain injury, trichotillomania, tuberous sclerosis, and white matter lesions.

While it may be possible for compounds of formula I to be administered as the raw chemical, it will often be preferable to present them as part of a pharmaceutical composition. In accordance with an embodiment of the present invention there is provided a pharmaceutical composition comprising a compound of formula I or a pharmaceutically acceptable salt thereof, together with one or more pharmaceutically carriers thereof and optionally one or more other therapeutic ingredients. The carrier(s) must be "acceptable" in the sense of being compatible with the other ingredients of the formulation and not deleterious to the recipient thereof. Furthermore, when reference is made in an independent claim to a compound or a pharmaceutically acceptable salt thereof, it will be understood that claims which depend from that independent claim which refer to such a compound also include pharmaceutically acceptable salts of the compound, even if explicit reference is not made to the salts in the dependent claim.

The formulations include those suitable for oral, parenteral (including subcutaneous, intradermal, intramuscular, intravenous and intraarticular), rectal and topical (including dermal, buccal, sublingual and intraocular) administration. The most suitable route may depend upon the condition and disorder of the recipient. The formulations may conveniently be presented in unit dosage form and may be prepared by any of the methods well known in the art of pharmacy. Such methods include the step of bringing into association a compound of formula I or a pharmaceutically acceptable salt or solvate thereof ("active ingredient") with the carrier, which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide sustained, delayed or controlled release of the active ingredient therein. The pharmaceutical compositions may include a "pharmaceutically acceptable inert carrier", and this expression is intended to include one or more inert excipients, which include starches, polyols, granulating agents, microcrystalline cellulose, diluents, lubricants, binders, disintegrating agents, and the like. If desired, tablet dosages of the disclosed compositions may be coated by standard-aqueous or non-aqueous techniques, "Pharmaceutically acceptable carrier" also encompasses controlled release means.

Pharmaceutical compositions may also optionally include other therapeutic ingredients, anti-caking agents, preservatives, sweetening agents, colorants, flavors, desiccants, plasticizers, dyes, and the like. Any such optional ingredient must be compatible with the compound of formula I to insure the stability of the formulation. The composition may contain other additives as needed, including for example lactose, glucose, fructose, galactose, trehalose, sucrose, maltose, raffinose, maltitol, melezitose, stachyose, lactitol, palatinite, starch, xylitol, mannitol, myoinositol, and the like, and hydrates thereof, and amino acids, for example alanine, glycine and betaine, and peptides and proteins, for example albumen.

Examples of excipients for use as the pharmaceutically acceptable carriers and the pharmaceutically acceptable inert carriers and the aforementioned additional ingredients include, but are not limited to binders, fillers, disintegrants, lubricants, anti-microbial agents, and coating agents.

The dose range for adult humans is generally from 0.005 mg to 10 g/day orally. Tablets or other forms of presentation provided in discrete units may conveniently contain an amount of compound of formula I which is effective at such dosage or as a multiple of the same, for instance, units containing 5 mg to 500 mg, usually around 10 mg to 200 mg. The precise amount of compound administered to a patient will be the responsibility of the attendant physician. However, the dose employed will depend on a number of factors, including the age and sex of the patient, the precise disorder being treated, and its severity.

A dosage unit (e.g. an oral dosage unit) can include from, for example, 1 to 30 mg, 1 to 40 mg, 1 to 100 mg, 1 to 300 mg, 1 to 500 mg, 2 to 500 mg, 3 to 100 mg, 5 to 20 mg, 5 to 100 mg (e.g. 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 150 mg, 200 mg, 250 mg, 300 mg, 350 mg, 400 mg, 450 mg, 500 mg) of a compound described herein.

For additional information about pharmaceutical compositions and their formulation, see, for example, Remington: The Science and Practice of Pharmacy, 20$^{th}$ Edition, 2000. The agents can be administered, e.g., by intravenous injection, intramuscular injection, subcutaneous injection, intraperitoneal injection, topical, sublingual, intraarticular (in the joints), intradermal, buccal, ophthalmic (including intraocular), intranasaly (including using a cannula), or by other routes. The agents can be administered orally, e.g., as a tablet or cachet containing a predetermined amount of the active ingredient, gel, pellet, paste, syrup, bolus, electuary, slurry, capsule, powder, granules, as a solution or a suspension in an aqueous liquid or a non-aqueous liquid, as an oil-in-water liquid emulsion or a water-in-oil liquid emulsion, via a micellar formulation (see, e.g. WO 97/11682) via a liposomal formulation (see, e.g., EP 736299, WO 99/59550 and WO 97/13500), via formulations described in WO 03/094886 or in some other form. The agents can also be administered transdermally (i.e. via reservoir-type or matrix-type patches, microneedles, thermal poration, hypodermic needles, iontophoresis, electroporation, ultrasound or other forms of sonophoresis, jet injection, or a combination of any of the preceding methods (Prausnitz et al. 2004, Nature Reviews Drug Discovery 3:115)). The agents can be administered locally, for example, at the site of injury to an injured blood vessel. The agents can be coated on a stent. The agents can be administered using high-velocity transdermal particle injection techniques using the hydrogel particle formulation described in U.S. 20020061336. Additional particle formulations are described in WO 00/45792, WO 00/53160, and WO 02/19989. An example of a transdermal formulation containing plaster and the absorption promoter dimethylisosorbide can be found in WO 89/04179. WO 96/11705 provides formulations suitable for transdermal administration. The agents can be administered in the form a suppository or by other vaginal or rectal means. The agents can be administered in a transmembrane formulation as described in WO 90/07923. The agents can be administered non-invasively via the dehydrated particles described in U.S. Pat. No. 6,485,706. The agent can be administered in an enteric-coated drug formulation as described in WO 02/49621. The agents can be administered intranasaly using the formulation described in U.S. Pat. No. 5,179,079. Formulations suitable for parenteral injection are described in WO 00/62759. The agents can be administered using the casein formulation described in U.S. 20030206939 and WO 00/06108. The agents can be administered using the particulate formulations described in U.S. 20020034536.

The agents, alone or in combination with other suitable components, can be administered by pulmonary route utilizing several techniques including but not limited to intratracheal instillation (delivery of solution into the lungs by syringe), intratracheal delivery of liposomes, insufflation (administration of powder formulation by syringe or any other similar device into the lungs) and aerosol inhalation. Aerosols (e.g., jet or ultrasonic nebulizers, metered-dose inhalers (MDIs), and dry-Powder inhalers (DPIs)) can also be used in intranasal applications. Aerosol formulations are stable dispersions or suspensions of solid material and liquid droplets in a gaseous medium and can be placed into pressurized acceptable propellants, such as hydrofluoroalkanes (HFAs, i.e. HFA-134a and HFA-227, or a mixture thereof), dichlorodifluoromethane (or other chlorofluorocarbon propellants such as a mixture of Propellants 11, 12, and/or 114), propane, nitrogen, and the like. Pulmonary formulations may include permeation enhancers such as fatty acids, and saccharides, chelating agents, enzyme inhibitors (e.g., protease inhibitors), adjuvants (e.g., glycocholate, surfactin, span 85, and nafamostat), preservatives (e.g., benzalkonium chloride or chlorobutanol), and ethanol (normally up to 5% but possibly up to 20%, by weight). Ethanol is commonly included in aerosol compositions as it can improve the function of the metering valve and in some cases also improve the stability of the dispersion. Pulmonary formulations may also include surfactants which include but are not limited to bile salts and those described in U.S. Pat. No. 6,524,557 and references therein. The surfactants described in U.S. Pat. No. 6,524,557, e.g., a $C_8$-$C_{16}$ fatty acid salt, a bile salt, a phospholipid, or alkyl saccharide are advantageous in that some of them also reportedly enhance absorption of the compound in the formulation. Also suitable in the invention are dry powder formulations comprising a therapeutically effective amount of active compound blended with an appropriate carrier and adapted for use in connection with a dry-Powder inhaler. Absorption enhancers which can be added to dry powder formulations of the present invention include those described in U.S. Pat. No. 6,632,456. WO 02/080884 describes new methods for the surface modification of powders. Aerosol formulations may include U.S. Pat. Nos. 5,230,884, 5,292,499, WO 017/8694, WO 01/78696, U.S. 2003019437, U.S. 20030165436, and WO 96/40089 (which includes vegetable oil). Sustained release formulations suitable for inhalation are described in U.S. 20010036481 A1, 20030232019A1, and U.S. 20040018243A1 as well as in WO 01/13891, WO 02/067902, WO 03/072080, and WO 03/079885. Pulmonary formulations containing microparticles are described in WO 03/015750, U.S. 20030008013, and WO 00/00176. Pulmonary formulations containing stable glassy state powder are described in U.S. 20020141945 and U.S. Pat. No. 6,309,671. Other aerosol formulations are described in EP 1338272A1 WO 90/09781, U.S. Pat. Nos. 5,348,730, 6,436,367, WO 91/04011, and U.S. Pat. Nos. 6,294,153 and 6,290,987 describes a liposomal based formulation that can be administered via aerosol or other means. Powder formulations for inhalation are described in U.S. 20030053960 and WO 01/60341. The agents can be administered intranasally as described in U.S. 20010038824.

Solutions of medicament in buffered saline and similar vehicles are commonly employed to generate an aerosol in a nebulizer. Simple nebulizers operate on Bernoulli's principle and employ a stream of air or oxygen to generate the spray particles. More complex nebulizers employ ultrasound to create the spray particles. Both types are well known in the art and are described in standard textbooks of pharmacy such as Sprowls' American Pharmacy and Remington's The Science and Practice of Pharmacy. Other devices for generating aerosols employ compressed gases, usually hydrofluorocarbons and chlorofluorocarbons, which are mixed with the medicament and any necessary excipients in a pressurized container, these devices are likewise described in standard textbooks such as Sprowls and Remington.

The agent can be incorporated into a liposome to improve half-life. The agent can also be conjugated to polyethylene glycol (PEG) chains. Methods for pegylation and additional formulations containing PEG-conjugates (i.e. PEG-based hydrogels, PEG modified liposomes) can be found in Harris and Chess, Nature Reviews Drug Discovery 2:214-221 and the references therein. The agent can be administered via a nanocochlcate or cochleate delivery vehicle (BioDelivery Sciences International). The agents can be delivered transmucosally (i.e. across a mucosal surface such as the vagina, eye or nose) using formulations such as that described in U.S. Pat. No. 5,204,108. The agents can be formulated in microcapsules as described in WO 88/01165. The agent can be administered intra-orally using the formulations described in U.S. 20020055496, WO 00/47203, and U.S. Pat. No. 6,495,120. The agent can be delivered using nanoemulsion formulations described in WO 01/91728A2.

In general, compounds of formula I may be prepared by the methods illustrated in the general reaction schemes as, for example, described below, or by modifications thereof, using readily available starting materials, reagents and conventional synthesis procedures. In these reactions, it is also possible to make use of variants that are in themselves known, but are not mentioned here.

The invention relates to compounds of formula I:

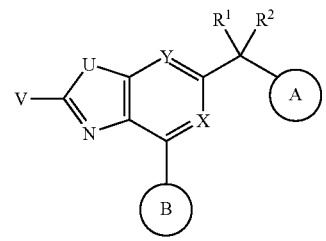

as described above.

In accordance with some embodiments of the invention, Y is CH. In accordance with other embodiments, Y is N.

In accordance with some embodiments of the invention, U is S. In accordance with other embodiments, U is O.

In accordance with some embodiments of the invention, V is selected from H, $CH_3$ and $NH_2$. In accordance with some embodiments, V is H. In accordance with some embodiments, V is $CH_3$. In accordance with some embodiments, V is $NH_2$.

In accordance with some embodiments of the invention, B is phenyl which has a substituent at the 3-position, the 4-position and at both the 3- and 4-positions. In some embodiments, B is selected from 3-chlorophenyl, 3-nitrophenyl, 3-cyanophenyl, 3-bromophenyl, 3-acetylphenyl, 3-trifluoromethylphenyl, and 3-methylthiophenyl. In some embodiments B is benzo[c][1,2,5]oxadiazol-5-yl and benzo[d][1,3]dioxol-5-yl.

In accordance with some embodiments of the invention, $R^1$ and $R^2$ are both H. In some embodiments, $R^1$ is H and $R^2$ is OH.

In accordance with some embodiments of the invention, A is optionally substituted phenyl; in other embodiments A is selected from the group consisting of optionally substituted 5- and 6-membered ring nitrogen heterocycles. In accordance with some embodiments of the invention, A is selected from the group consisting of optionally substituted pyridinyl, phenyl, morpholin-4-yl, piperazin-1-yl, piperidiny-1-yl, imidazol-1-yl, pyrazol-1-yl, and pyrazol-5-yl.

In accordance with some embodiments of the invention, X is selected from the group consisting of CH, C—F, C—OH and N.

In accordance with some embodiments of the invention, the compounds are of formula

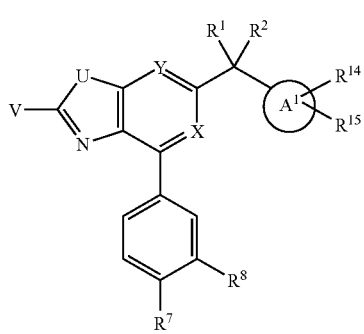

wherein

A¹ is phenyl, five-membered heteroaryl, six-membered heteroaryl, 4-7 membered non-aryl heterocycle or fused bicycle;

R⁷ is H or F;

R⁸ is chosen from halogen, nitro, acetyl, hydroxyethyl, amino, methylthio, trifluoromethyl, methoxymethyl, methoxycarbonyl, trifluoromethoxy, cyano and 1,3,4-thiadiazol-2-yl, or taken together R⁷ and R⁸ are methylenedioxy, =N—O—N=, —NH—CH=N— or difluoromethylenedioxy;

R¹⁴ is chosen from H, halogen, haloalkyl, alkyl, acyl, alkoxyalkyl, hydroxyalkyl, carbonyl, phenyl, heteroaryl, benzenesulfonyl, hydroxy, alkoxy, haloalkoxy, oxaalkyl, carboxy, alkoxycarbonyl, alkoxycarbonylalkyl, alkoxycarbonylamino, carboxyalkyl, alkoxycarbonylaminoalkyl, carboxyalkylcarbonylamino, carboxamido, aminocarbonyloxy, alkylaminocarbonyl, dialkylaminocarbonyl, aminocarbonylalkyl, cyano, acetoxy, nitro, amino, alkylamino, dialkylamino, aminoalkyl, (alkyl)(aryl)aminoalkyl, alkylaminoalkyl, dialkylaminoalkyl, dialkylaminoalkoxy, alkyl(hydroxyalkyl)amino, heterocyclylalkoxy, mercapto, alkylthio, alkylsulfonyl, alkylsulfonylamino, alkylsulfinyl, alkylsulfonyl, arylthio, arylsulfonyl, arylsulfonylamino, arylsulfinyl, arylsulfonyl, acylaminoalkyl, acylaminoalkoxy, acylamino, amidino, aryl, benzyl, heterocyclyl, heterocyclylalkyl, phenoxy, benzyloxy, heteroaryloxy, heterocyclylamino, hydroxyimino, alkoxyimino, oxaalkyl, aminosulfonyl, trityl, amidino, guanidino, ureido, —NHC(=O)NHalkyl, —NHC(=O)NH-heterocyclyl, -alkyl-NHC(=O)N(alkyl)₂, heterocyclylalkylcarbonylamino, benzyloxyphenyl, benzyloxy, the residues of amino acids, amino acid amides, protected residues of aminoacids, protected residues of amino acid amides, N-methylated amino acids and N-methylated amino acid amides;

alternatively, R¹⁴ may be chosen from H, —CH₃, —CH₂CF₃, —CF₃, —CHO, —COOH, —CN, halogen, —OH, —OEt, —C(=O)NH₂, —C(=O)NHEt, —C(=O)NMe₂-COOCH₃, —COOEt, —CH₂NHC(=O)NH₂, —CH(CH₃)NHC(=O)NH₂, —CH₂NHC(=O)H, —CH₂NHC(=O)CH₃, —CH₂C(=O)NH₂, —CH₂COOH, —CH₂COOEt, —CH₂NHC(=O)OEt, —CH₂NHC(=O)O—C₆H₅, —CH₂NHC(=O)C(=O)NH₂, —CH₂NHC(=O)NHEt, —C(CH₃)₂OH, —CH₂NHC(=O)N(CH₃)₂, —CH₂NHC(=O)NHCH₃, —CH₂NH₂, —CH(CH₃)NH₂, —C(CH₃)₂NH₂, —CH₂OH, —CH₂CH₂OH, —CH₂NHSO₂CH₃, —CH₂C(=O)NHEt, —OCH₃, —OC(=O)NH₂, —OCH₂CH₂N(CH₃)₂, —OCH₂CH₂OCH₃, —NHC(=O)NH₂, —NHC(=O)NHEt, —NHCH₃, —NHEt, —NH(tBoc), —NHCH₂COOH, —N(CH₃)CH₂COOH, —NHC(=O)NHCH₂CH₂Cl, —NHSO₂NH₂, —NHEt, —N(CH₃)₂, —NH₂, —NH(CH₃)C(=O)NH₂, —NHSO₂CH₃, —N(SO₂CH₃)₂, —NHC(=O)OCH₃, —NHC(=O)OtBu, —NHC(=O)CH₃, —SO₂NH₂, —NHC(=O)CH₂CH₂COOH, —NHC(=O)NHCH₂COOH, —CH₂NHCHO, —NHC(=O)NHCH₂COOEt, —NHC(=O)NH(CH₂)₃COOEt, —NHC(=O)NH(CH₂)₂COOEt, —N(CH₃)CH₂CH₂OH, —NHC(=O)OEt, —N(Et)C(=O)OEt, —NHC(=O)NH(CH₂)₂COOH, —NHC(=O)CH₂N(CH₃)₂, —NHC(=O)NH(CH₂)₃COOH, —NHC(=O)CH₂NH₂, —NHC(=O)CH₂CH₂NH₂, —NHC(=O)CH₂NH(tBoc),

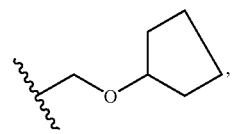

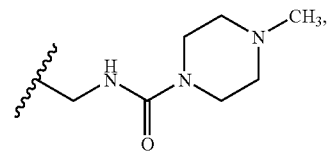

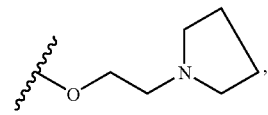

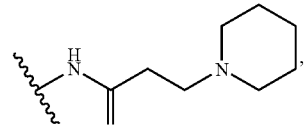

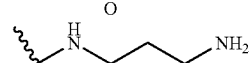

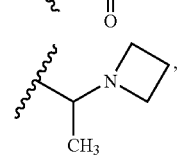

and monocyclic heterocycle substituted with any of the foregoing;

R¹⁵ is chosen from H, NO₂, OH, NH₂, and —NHSO₂NH₂; or R¹⁵ together with R¹⁴ forms methylene dioxy.

An example of the embodiment in which A¹ is a monocyclic heterocycle attached to a monocyclic heterocycle substituted with a carboxylic acid is found in example BB-01 below:

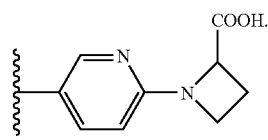 [SMILES: *c1ccc(N2CCC2C(=O)O)nc1]

Exemplary carboxyalkoxy and carboxyalkylthio are lactic acid and thioglycollic acid respectively. Exemplary amino acids are glycine, alanine and proline.

In some embodiments of the invention, the compound is selected from the following:

TABLE 1

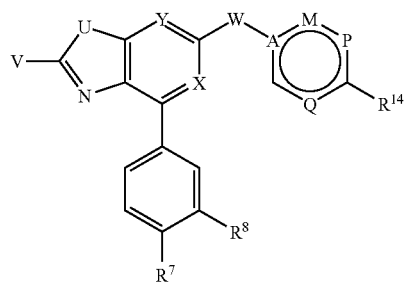

| Cmpd No | V | U | X | Y | W | A | M | P | Q | R14 | R3 | R4 |
|---|---|---|---|---|---|---|---|---|---|---|---|---|
| BA-01 | NH2 | S | CH | CH | CH2 | C | CH | CH | CH | F | NO2 | H |
| BA-02 | NH2 | S | CH | CH | CH2 | N | CH | N | — | H | NO2 | H |
| BA-03 | NH2 | S | CH | CH | CH2 | C | CH | CH | CH | F | N—O—N | |
| BA-04 | NH2 | S | CH | CH | CH2 | C | CH | CH | CH | F | O—CH2—O | |
| BA-05 | NH2 | S | CH | CH | CH(OH) | C | CH | CH | CH | F | O—CH2—O | |
| BA-06 | NH2 | S | CH | CH | CH(OH) | C | NMe | N | — | H | O—CH2—O | |
| BA-07 | NH2 | S | CH | CH | CH2 | C | CH | CH | CH | F | CF3 | H |
| BA-08 | NH2 | S | CH | CH | CH2 | C | NMe | N | — | H | O—CH2—O | |
| BA-09 | NH2 | S | CH | CH | CH2 | N | N | CH | — | H | O—CH2—O | |
| BA-11 | NH2 | S | N | N | CH2 | C | CH | CH | CH | F | O—CH2—O | |
| BA-10 | NH2 | S | CH | CH | CH2 | N | N | CH | — | H | NO2 | H |
| BA-12 | NH2 | S | CH | CH | CH2 | N | N | CH | — | H | COCH3 | H |
| BA-13 | NH2 | S | CH | CH | CH2 | C | CH | CH | CH | F | Br | H |
| BA-14 | NH2 | S | CH | CH | CH2 | N | N | CH | — | H | SCH3 | H |
| BA-15 | NH2 | S | C—OH | CH | CH2 | C | CH | CH | CH | NH2 | NO2 | H |
| BA-16 | NH2 | S | CF | CH | CH2 | C | CH | CH | CH | NH2 | Cl | H |
| BA-18 | NH2 | S | CH | CH | CH2 | C | CH | CH | CH | NHSO2CH3 | Cl | H |
| BA-19 | NH2 | S | CF | CH | CH2 | C | CH | CH | CH | NHSO2CH3 | Cl | H |
| BA-20 | NH2 | O | CH | CH | CH2 | C | CH | CH | CH | NHSO2CH3 | Cl | H |
| BA-21 | NH2 | S | CF | CH | CH2 | C | CH | CH | CH | NHCONH2 | Cl | H |
| BA-22 | NH2 | O | CH | CH | CH2 | C | CH | CH | CH | NH2 | Cl | H |
| BA-23 | H | S | CF | CH | CH2 | C | CH | CH | CH | NH2 | Cl | H |
| BA-25 | H | S | CH | CH | CH2 | C | CH | CH | CH | NH2 | Cl | H |
| BA-26 | NH2 | S | CH | CH | CH2 | C | CH | CH | CH | NH2 | Cl | H |
| BA-27 | NH2 | S | CH | CH | CH2 | C | CH | CH | CH | NHCONH2 | Cl | H |
| BA-28 | H | S | CH | CH | CH2 | C | CH | CH | CH | NHCONH2 | Cl | H |
| BA-24 | CH3 | O | CH | CH | CH2 | C | CH | CH | CH | NHCONH2 | Cl | H |
| BA-29 | NH2 | S | CF | CH | CH2 | C | CH | CH | CH | NHCONH—Et | Cl | H |
| BA-30 | H | S | CF | CH | CH2 | C | CH | CH | CH | NHCONH—Et | Cl | H |
| BA-32 | NH2 | O | CH | CH | CH2 | C | CH | CH | CH | NH2 | Cl | H |
| BA-33 | H | S | CF | CH | CH2 | C | CH | N | CH | NHCONH—Et | Cl | H |
| BA-38 | H | S | CF | CH | CH2 | C | CH | N | CH | OCH3 | Cl | H |
| BA-39 | H | S | CF | CH | CH2 | C | CH | C(OH) | CH | H | Cl | H |
| BA-40 | H | S | CF | CH | CH2 | C | CH | N | CH | NHCOO—Et | Cl | H |
| BA-51 | H | S | CF | CH | CH2 | C | CH | CH | CH | NHCONH2 | Cl | H |
| BA-53 | H | S | CF | CH | CH2 | C | CH | N | CH | NHCONHEt | CN | H |
| BA-55 | H | S | CF | CH | CH2 | C | CH | CH | CH | NMe2 | Cl | H |
| BA-57 | H | S | CF | CH | CH2 | C | CH | CH | CH | N-Pyrrolidine | Cl | H |
| BA-58 | H | S | CH | CH | CH2 | C | CH | CH | CH | NMe2 | Cl | H |
| BA-59 | H | S | CH | CH | CH2 | C | CH | CH | CH | N-Pyrrolidine | Cl | H |
| BA-60 | H | S | CF | CH | CH2 | C | CH | CH | CH | CN | Cl | H |
| BA-61 | H | S | CF | CH | CH2 | C | CH | CH | CH | N-azetidine | Cl | H |
| BA-63 | H | S | CF | CH | CH2 | C | CH | CH | CH | NH2 | Cl | H |
| BA-64 | H | S | CF | CH | CH2 | C | CH | CH | CH | NHCO—CH2—NMe2 | Cl | H |
| BA-66 | CH3 | S | CH | CH | CH2 | C | CH | CH | CH | NH2 | Cl | H |
| BA-67 | CH3 | S | CH | CH | CH2 | C | CH | CH | CH | NHCO—CH2—NMe2 | Cl | H |
| BA-74 | H | S | CF | CH | CH2 | C | CH | CH | CH | N-azetidine-(R)-2-carboxamide | Cl | H |
| BA-75 | H | S | CF | CH | CH2 | C | CH | CH | CH | N-azetidine-(S)-2-carboxamide | Cl | H |

TABLE 2

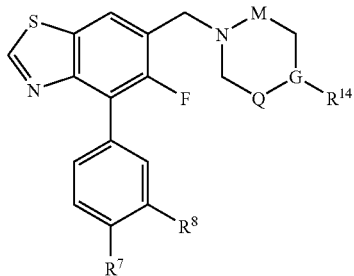

| Cmpd no | M | Q | L | G | R14 | R8 | R7 |
|---|---|---|---|---|---|---|---|
| BA-31 | CH2 | CH2 | CH2 | N | CONH2 | Cl | H |
| BA-43 | CH2 | CH2 | CH2 | O | — | Cl | H |
| BA-44 | CH2 | CH2 | CH2 | N | COCH3 | Cl | H |
| BA-45 | CH2 | CH2 | CH2 | CH | NH—CO2—Et | Cl | H |
| BA-46 | CH2 | CH2 | CH2 | CH | NCONH2 | Cl | H |
| BA-47 | CH2 | CH2 | CH2 | CH | NH2 | Cl | H |
| BA-48 | CH2 | CH2 | CH2 | N | H | Cl | H |
| BA-49 | CH2 | CH2 | CH2 | N | CO2Et | Cl | H |
| BA-50 | CH2 | CH2 | CH2 | N | CH3 | Cl | H |
| BA-52 | CH2 | CH2 | CH2 | N | CO—NHEt | Cl | H |
| BA-54 | CH2 | — | CH2 | CH | H | Cl | H |
| BA-71 | CH2 | CO | CH2 | N | H | Cl | H |
| BA-72 | CO | CH2 | CH2 | N | CONH—Et | Cl | H |
| BA-73 | CO | CH2 | CH2 | N | H | Cl | H |

All of the compounds falling within the foregoing parent genus I and its subgenera are useful as PDE4 inhibitors. It may be found upon examination that species and genera not presently excluded are not patentable to the inventors in this application because of prior art. In this case, the exclusion of species and genera in applicants' claims are to be considered artifacts of patent prosecution and not reflective of the inventors' concept or description of their invention. The invention, in a composition aspect, is all active compounds of formula I except those that are in the public's possession.

In general, compounds of formula I may be prepared by the methods illustrated in the general reaction schemes as, for example, described below, or by modifications thereof, using readily available starting materials, reagents and conventional synthesis procedures. In these reactions, it is also possible to make use of variants that are in themselves known, but are not mentioned here.

Tables 1 and 2 above list compounds representative of embodiments of the invention. Processes for obtaining compounds of formula I are presented below. Other compounds of formula I may be prepared in analogous fashion to those whose synthesis is exemplified herein. The procedures below illustrate such methods. Furthermore, although the syntheses depicted herein may result in the preparation of enantiomers having a particular stereochemistry, included within the scope of the present invention are compounds of formula I in any stereoisomeric form, and preparation of compounds of formula I in stereoisomeric forms other than those depicted herein would be obvious to one of ordinary skill in the chemical arts based on the procedures presented herein.

Synthetic Methods

Generally compounds of the Formula I, can be prepared by sequential introduction of substitution at the 4 and 6 positions of the benzoazoles. The introduction of the substituents at the C4 position to form a C—C bond can be accomplished by organometallic coupling protocols (e.g. Suzuki, Stille reaction) or by displacement of a halogen using metal assisted displacement with a cyclic or heterocyclic NH compound forming a C—N bond at the C4 position of the benzoazole. The atom numberings referenced in this section are shown in G1 (scheme 1). These reactions can be performed with benzoazole derivatives bearing a variety of functionalities at the C-2 which may include V=H, CH3, a protected or derivatized amine or ether. The 2-amino group of benzoazole (V=NH2) can be converted thru intermediacy of a diazo (—N+=N) group to from V=H (for example). The substituent at the C-6 position can be introduced by a wide variety of approaches. These chemistries employed depend of the 1-carbon functionality (CH3, CHO, COOR', CN etc.) present at the C-6. The benzoazoles bearing diverse functional groups which are amenable to standard function group interconversion, for example alkyl, ester, nitrile which could provide alcohol, alkyl halide could be manipulated by standard and these may include aldehyde, nitrile and esters, which allow generation of alcohol which could be converted to a carbonate or alkyl halide. These functionalities allow introduction of aryl, heteroaryl substituents through C—C forming chemistries. Alternatively nucleophilic displacement of the alkyl halide, OTs, OTf etc. allow incorporation of substituents via C—N bond forming approach to introduce cyclic, acylic, amine derived functional groups (G7). This strategy allows incorporation of acyclic, heterocyclic or heteroaryl derived substituents at the C6 position of the benzoazole nucleus.

Scheme A1

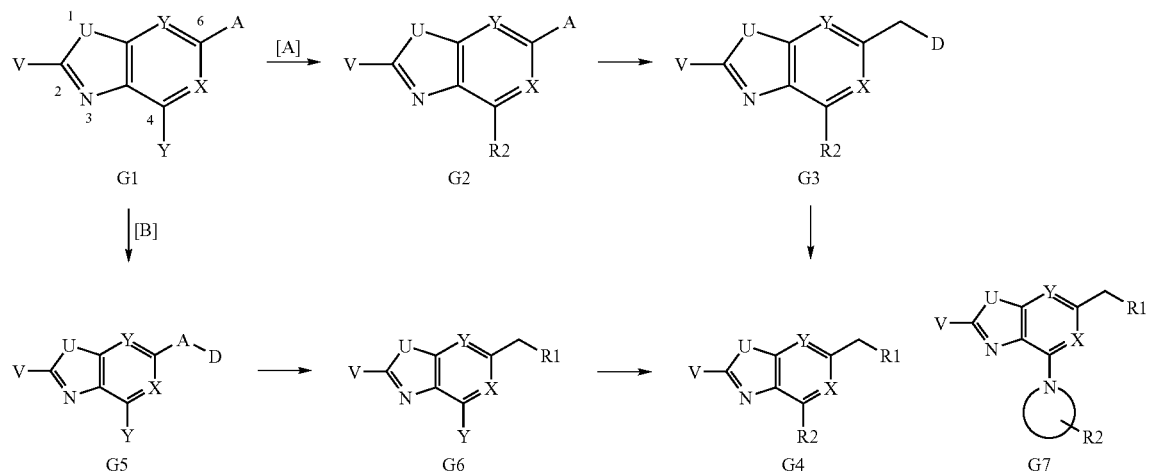

Moreover, introduction of substituents at C6 or C4 could be carried in either sequence, i.e. formation of C4 substituent followed by C6 (route A, G1->G2) or vice versa (route B, G1-.G5). Either of these substituents may carry additional functional groups which could be further derivatized through standard functional group transformation chemistries that are well know in the art. Some of these include formation of amide, sulfonamide, ureas, imidazolone, oxazolones, and carbamates from appropriate amine, carboxylic acid, alcohols or phenol groups. Additionally, when the R1 group contains an ortho-halo N-heterocycles (e.g 2-halo pyridine or 2-halo-pyrimidine) G8, a nucleophilic displacement of the halo (or —OTf, ONf derived from pyridin-2-one) groups. Examples of these nucleophile include an amine (primary, sec. tert.; acyclic or cyclic including) or NH-containing heteroaryl (for example, substituted imidazole or pyrazole); or alcohol/thiol allowing incorporation of additional —O, —S or —N linked substituents to provide G9. Alternatively, an appropriately functionalized pyridine can be converted to corresponding 2-OTf or 2-ONf which could then participate in similar chemistries.

Scheme A2

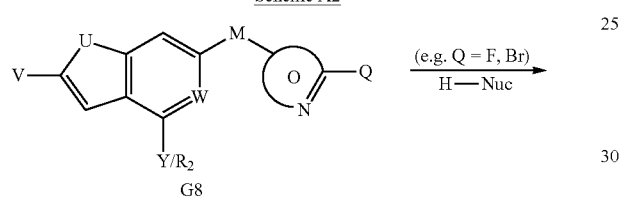

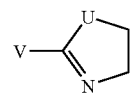

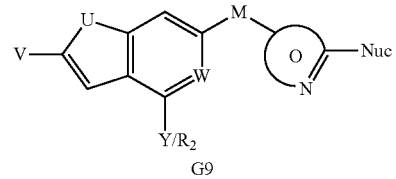

The R1 group could also be assembled form an acyclic intermediate (Scheme A3) to form a heterocylic or heteroaromatic ring. Examples of these chemistries include formation of 5-membered heteroaryls (G12) such as oxadiazole, thiadiazole, triazole form acyl hydrazide (G11); thiazole from 2-halo-ketone or dipolar cycloaddition reactions when the C4 or C6 substituent is an olefin or acetylic group (G10->G13)). Alternatively the 6-membered heteroaryl or heterocyclic rings could be formed using Diels-Alder or hetero-Diels-Alder chemistries using appropriately substituted alkyl aryl ether bearing either a dienophile or a diene at C4 or C6 position.

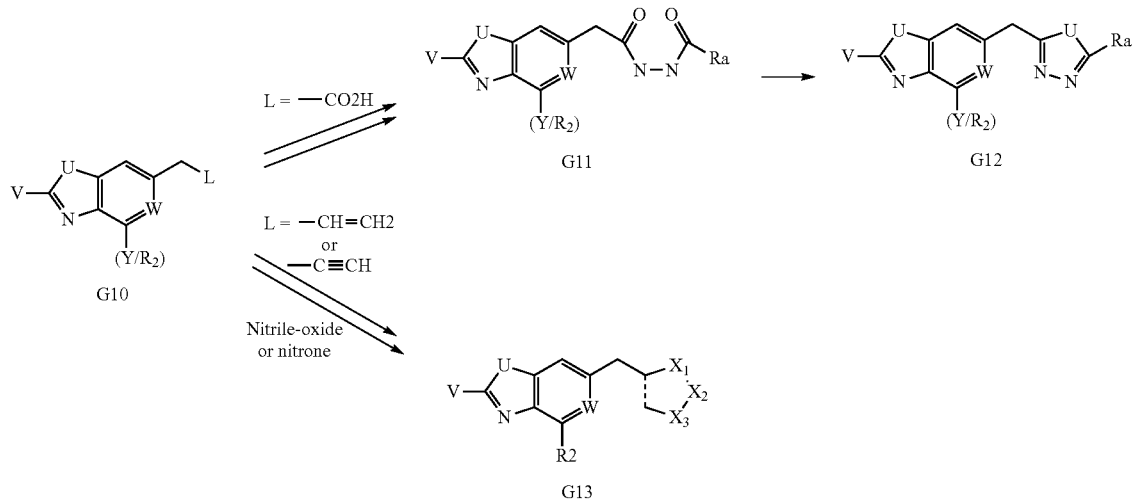

----- single or double bond e.g. isoxazole, isoxazoline

U = O, S, NR''''

With an aldehyde, ketone, nitrile or an ester at C6, addition of an organometallic (Grignard or organozinc reagent) allows formation of heteroatom containing substituents where Ra or Rb bear a heteroatom. Alternatively, when C6 is C—H, Friedle-Craft acylation provide a ketone (G17), which is subsequently transformed to sec. alcohol (via reduction), tert. alcohol (thru addition of an alkyl/aryl using RMgX or R2Zn) or sec. or tertiary amine thru mediation of an imine/oxime; or to —CH2-, providing variations at the linker position (G16).

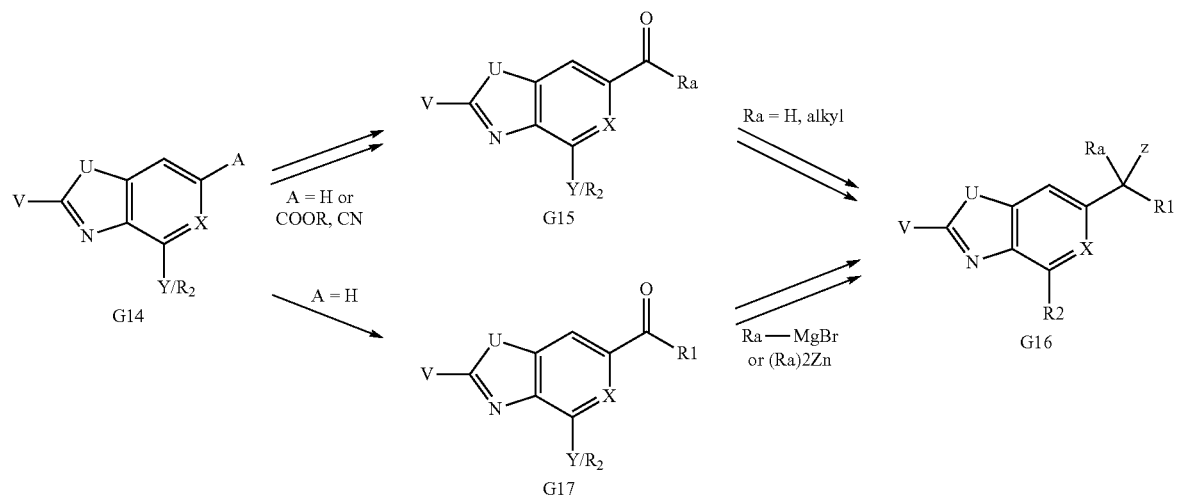

The above approaches describe means to decorate a benzoazole nucleus. On the other hand, one may also be able to start with 1,3 functionalized phenyl or heteroaryl (G20 or G22) which is then elaborated through construction of the fused five membered ring to assemble the benzoazole nucleus later stages in the synthesis of analogs corresponding to the genus 1. This approach is depicted in scheme A5. Example of this strategy is also provided in some non-limiting specific example in the later section.

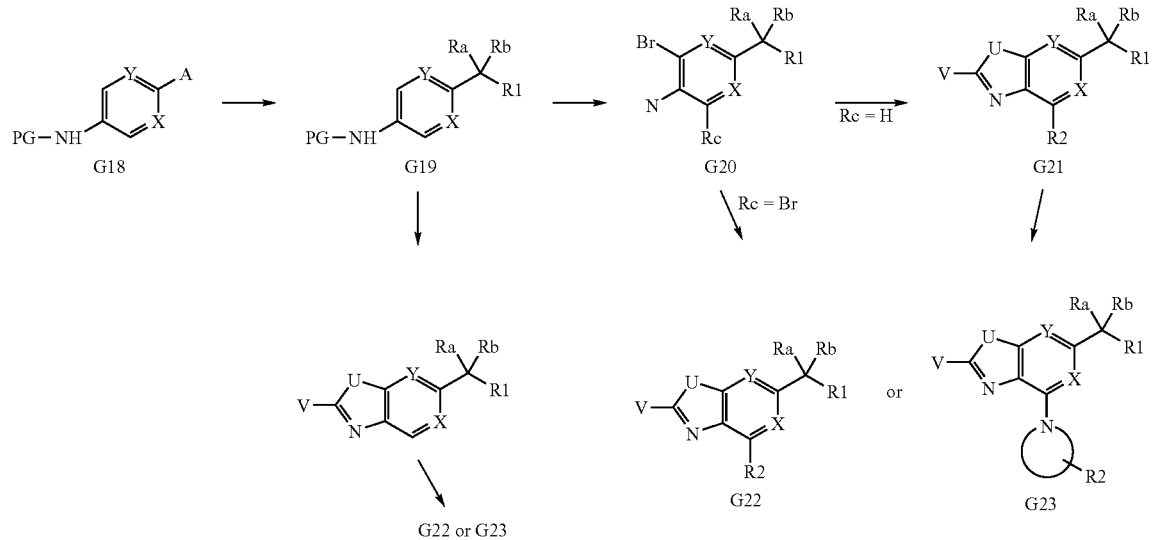

The diverse selection of substituents present in R1 could be formed by standard functional group transformations that are well know in the art. Some of these include formation of amide, sulfomanide, ureas, imidazolone, oxazolones, carbamates from the alkoxy-biaryl fragments bearing and appropriate amine, carboxylic acid, alcochols or phenol groups. When the R1 group contains an ortho-halo pyridine or pyrimidine for example, the nucleophilic displacement of the halo (or —OTf, ONf derived from pyridone) groups. Examples of the nucleophile include an amine (primary, sec. tert.; acyclic or cyclic including), alcohol or HN-containing heterocyclic groups (for example, substituted imidazole or pyrazole). These displacement reactions could be carried out using alkali or tert. amine base; or could be mediated thru use of an organometallic reagent such as Pd, or Al reagent.

Scheme 1 provides an outline of the synthesis of example 1.

Synthetic Methods

Generally compounds of the Formula I, can be prepared by sequential introduction of substitution at the 4 and 6 positions of the benzoazoles. The introduction of the substituents at the C4 position to form a C—C bond can be accomplished by organometallic coupling protocols (e.g. Suzuki, Stille reaction) or by displacement of a halogen using metal assisted displacement with a cyclic or heterocyclic NH compound forming a C—N bond at the C4 position of the benzoazole. The atom numberings referenced in this section are shown in G 1 (scheme 1). These reactions can be performed with benzoazole derivatives bearing a variety of functionalities at the C-2 which may include V=H, CH3, a protected or derivatized amine or ether. The 2-amino group of benzoazole (V=NH2) can be converted thru intermediacy of a diazo (—N+=N) group to from V=H (for example). The substituent at the C-6 position can be introduced by a wide variety of approaches. These chemistries employed depend of the 1-carbon functionality (CH3, CHO, COOR', CN etc.) present at the C-6. The benzoazoles bearing diverse functional groups which are amenable to standard function group interconversion, for example alkyl, ester, nitrile which could provide alcohol, alkyl halide could be manipulated by standard and these may include aldehyde, nitrile and esters, which allow generation of alcohol which could be converted to a carbonate or alkyl halide. These functionalities allow introduction of aryl, heteroaryl substituents through C—C forming chemistries. Alternatively nucleophilic displacement of the alkyl halide, OTs, OTf etc. allow incorporation of substituents via C—N bond forming approach to introduce cyclic, acyclic, amine derived functional groups (G7). This strategy allows incorporation of acyclic, heterocyclic or heteroaryl derived substituents at the C6 position of the benzoazole nucleus.

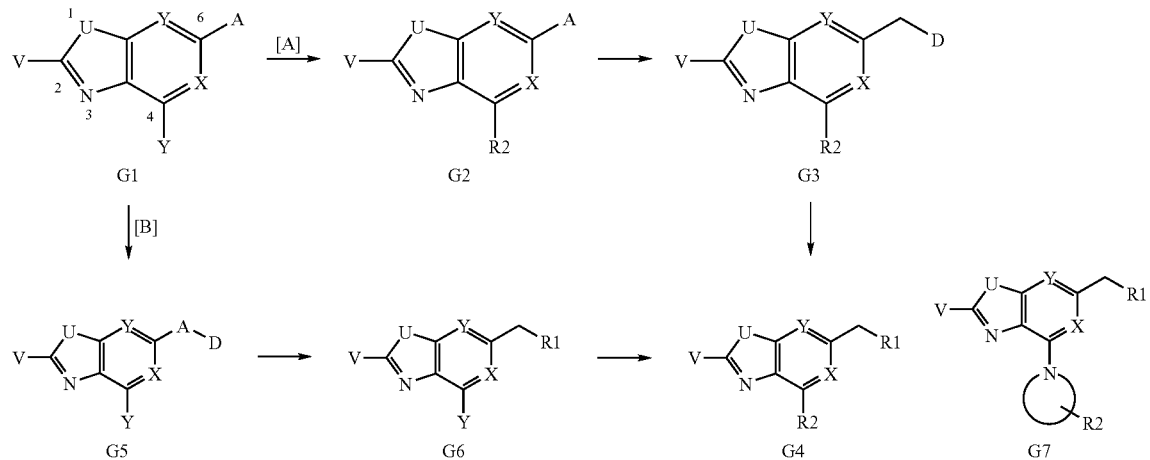

Scheme A1

Moreover, introduction of substituents at C6 or C4 could be carried in either sequence, i.e. formation of C4 substituent followed by C6 (route A, G1->G2) or vice versa (route B, G1-.G5). Either of these substituents may carry additional functional groups which could be further derivatized through standard functional group transformation chemistries that are well know in the art. Some of these include formation of amide, sulfonamide, ureas, imidazolone, oxazolones, and carbamates from appropriate amine, carboxylic acid, alcohols or phenol groups. Additionally, when the R1 group contains an ortho-halo N-heterocycles (e.g 2-halo pyridine or 2-halo-pyrimidine) G8, a nucleophilic displacement of the halo (or —OTf, ONf derived from pyridin-2-one) groups. Examples of these nucleophile include an amine (primary, sec. tert.; acyclic or cyclic including) or NH-containing heteroaryl (for example, substituted imidazole or pyrazole); or alcohol/thiol allowing incorporation of additional —O, —S or —N linked substituents to provide G9. Alternatively, an appropriately functionalized pyridine can be converted to corresponding 2-OTf or 2-ONf which could then participate in similar chemistries.

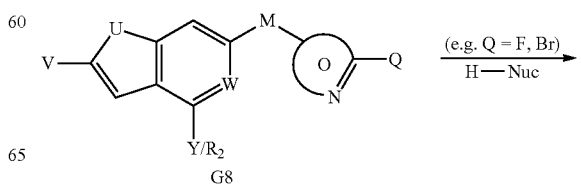

Scheme A2

-continued

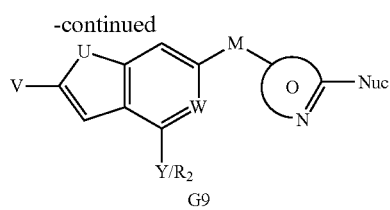

The R1 group could also be assembled form an acyclic intermediate (Scheme A3) to form a heterocylic or heteroaromatic ring. Examples of these chemistries include formation of 5-membered heteroaryls (G12) such as oxadiazole, thiadiaz-

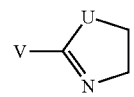

ole, triazole form acyl hydrazide (G11); thiazole from 2-haloketone or dipolar cycloaddition reactions when the C4 or C6 substituent is an olefin or acetylic group (G10->G13)). Alternatively the 6-membered heteroaryl or heterocyclic rings could be formed using Diels-Alder or hetero-Diels-Alder chemistries using appropriately substituted alkyl aryl ether bearing either a dienophile or a diene at C4 or C6 position.

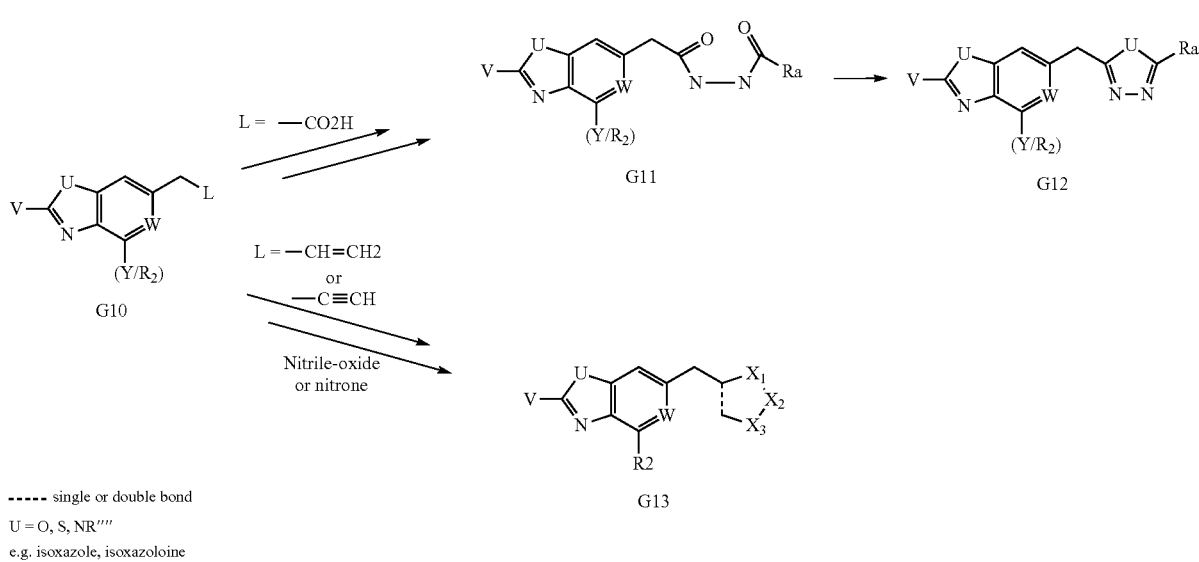

----- single or double bond
U = O, S, NR''''
e.g. isoxazole, isoxazoloine

With an aldehyde, ketone, nitrile or an ester at C6, addition of an organometallic (Grignard or organozinc reagent) allows formation of heteroatom containing substituents where Ra or Rb bear a heteroatom. Alternatively, when C6 is C—H, Friedle-Craft acylation provide a ketone (G17), which is subsequently transformed to sec. alcohol (via reduction), tert. alcohol (thru addition of an alkyl/aryl using RMgX or R2Zn) or sec. or tertiary amine thru mediation of an imine/oxime; or to —CH2-, providing variations at the linker position (G16).

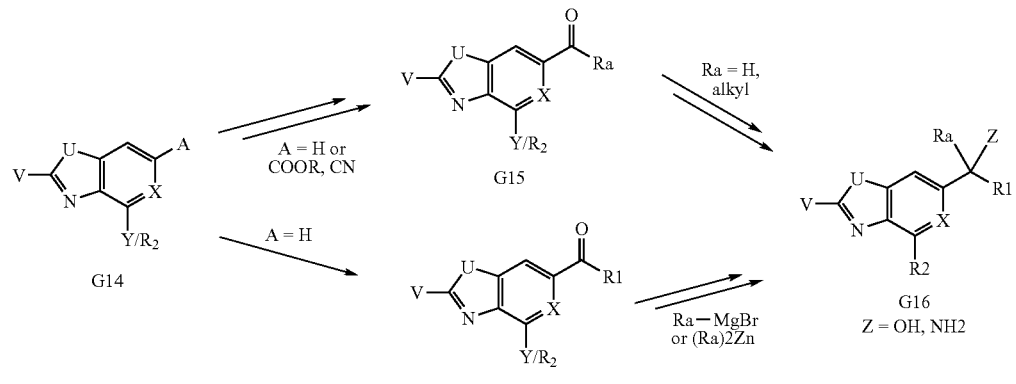

The above approaches describe means to decorate a benzoazole nucleus. On the other hand, one may also be able to start with 1,3 functionalized phenyl or heteroaryl (G20 or G22) which is then elaborated through construction of the fused five membered ring to assemble the benzoazole nucleus later stages in the synthesis of analogs corresponding to the genus I. This approach is depicted in scheme A5. Example of this strategy is also provided in some non-limiting specific example in the later section.

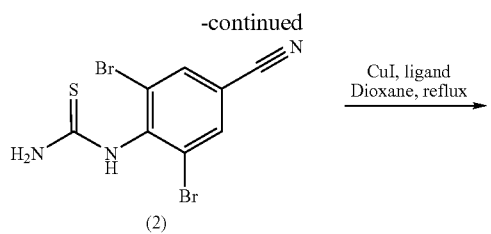

(2)

Scheme A5

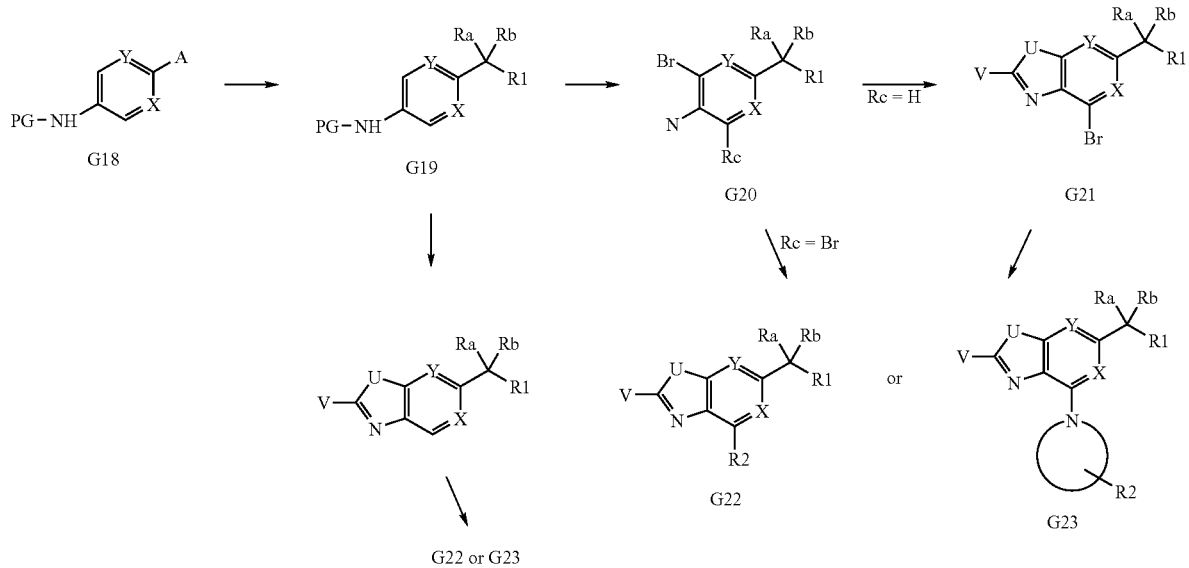

PG = Protectiung group or H

The diverse selection of substituents present in R1 could be formed by standard functional group transformations that are well know in the art. Some of these include formation of amide, sulfomanide, ureas, imidazolone, oxazolones, carbamates from the alkoxy-biaryl fragments bearing and appropriate amine, carboxylic acid, alcochols or phenol groups. When the R1 group contains an ortho-halo pyridine or pyrimidine for example, the nucleophilic displacement of the halo (or —OTf, ONf derived from pyridone) groups. Examples of the nucleophile include an amine (primary, sec. tert.; acyclic or cyclic including), alcohol or HN-containing heterocylic groups (for example, substituted imidazole or pyrazole). These displacement reactions could be carried out using alkali or tert. amine base; or could be mediated thru use of an organometallic reagent such as Pd, or Al reagent.

Scheme 1 provides an outline of the synthesis of example 1.

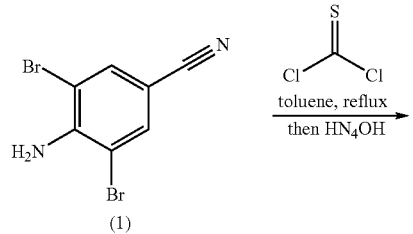

(1)

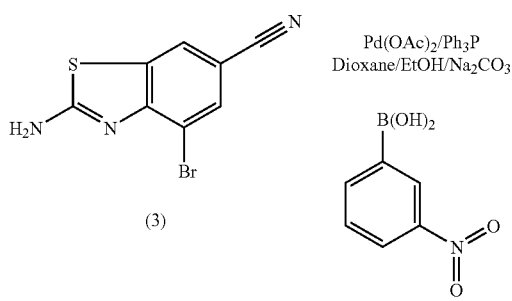

(3)

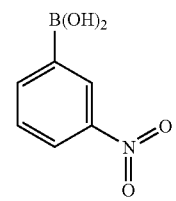

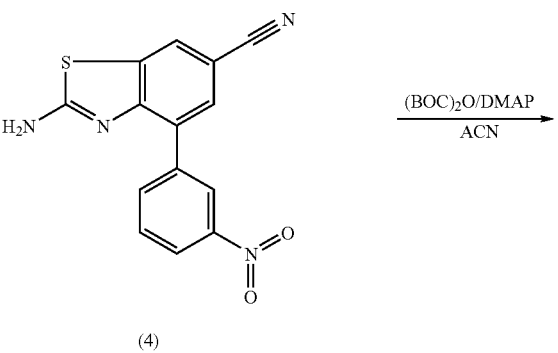

(4)

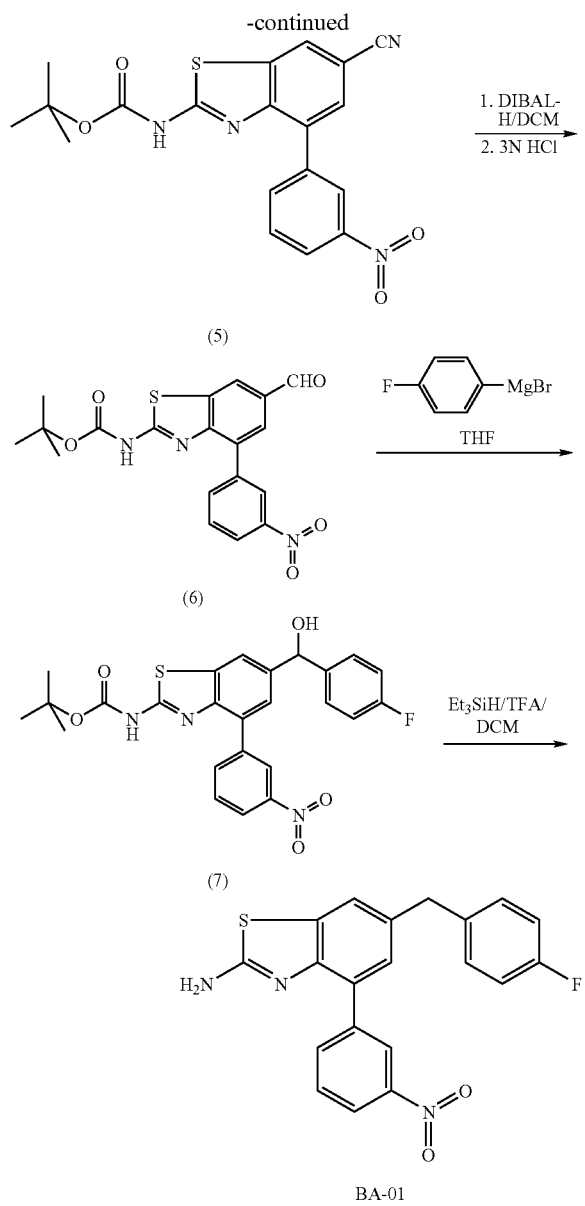

mL×3). The solid was dried in vacuo at room temperature overnight, to provide 1 g (quantitative yield) of the desired product (3). $^1$H-NMR-(400 MHz, CDCl$_3$)

2-amino-4-(3-nitro-phenyl)-benzothiazole-6-carbonitrile. (4). A mixture of compound (3) (750 mg, 3 mmol), 3-nitrophenyl-boronic acid (752 mg, 4.5 mmol), triphenylphosphine (470 mg, 1.8 mmol, 0.6 eq.), Pd(OAc)$_2$ (130 mg, 0.6 mmol, 0.2 eq.) in dioxane (30 mL), ethanol (9 mL) and (aqueous) 1N Na$_2$CO$_3$ (9 mL, 3 eq.) was stirred at under reflux overnight under Argon. The reaction mixture was diluted with water (100 mL) and extracted with ethyl acetate (3×100 mL). The combined organic phase was passed through a filtration funnel. Evaporation of solvent gave a residue, which was treated with dichloromethane (3×20 mL) to afford the desired product (4) 530 mg (45% yield). $^1$H-NMR-(400 MHz, DMSO-d6). MS (ESI+): 301.7 (M+1). LC-MS: 90%.

[6-cyano-4-(3-nitro-phenyl)-benzothiazol-2-yl]-carbamic acid tert-butyl ester (5) A reaction mixture of compound (4) (230 mg, 0.77 mmol), (Boc)$_2$O (220 mg, 1 mmol, 1.3 eq.) and DMAP (15 mg, 0.08 mmol, 0.1 eq.) in MeCN (10 mL) was stirred at room temperature for 48 h. The volatile material was removed under reduced pressure to give 300 mg (98% yield) of desired product (5) as yellow solid.

[6-formyl-4-(3-nitro-phenyl)-benzothiazol-2-yl]-carbamic acid tert-butyl ester. (6) To a solution of compound (5) (150 mg, 0.38 mmol) in dichloromethane (8 mL) was added DIBAL-H (1 mL, 1N in hexane) by a syringe at −60° C. After the addition was complete, the reaction mixture was allowed to warm to room temperature over 2 h. Then 1 mL of aqueous 3 N HCl was added and the mixture was stirred at room temperature for 20 min before additional 1 mL of aqueous 3 N HCl was added. After the resulting mixture was stirred for 30 min. dichloromethane (20 mL) was added followed by water (20 mL). The organic layer was separated and the aqueous layer was extracted with dichloromethane (3×15 mL). The combined organics was dried over Na$_2$SO$_4$. Evaporation of solvent under reduced pressure gave 120 mg (79% yield) of crude product (6). The product thus obtained was forward to the next step without any further purification.

[6-[(4-fluorophenyl)-hydroxymethyl]-4-(3-nitrophenyl)-benzothiazol-2-yl]-carbamic acid tert-butyl ester (7). To a solution of aldehyde (6) (120 mg, 0.3 mmol) in THF (4 mL) was added 4-fluorophenyl magnesium bromide (1 ml, 1N in THF) dropwise by a syringe at −78° C. The mixture was allowed to warm to room temperature and the reaction was monitored by TLC analysis. After the starting aldehyde was consumed, the reaction was quenched by addition of saturated NH$_4$Cl (aq) followed by aqueous 3 N HCl to bring the mixture to pH=3. The mixture was extracted with EtOAc (3×15 mL). The combined organics were dried over Na$_2$SO$_4$ and removal of solvent gave a residue, which was purified by chromatography on silica gel using hexanes/dichloromethane (1:2) followed by dichloromethane as eluent to give 65 mg (44% yield) of product (7).

6-(4-fluorobenzyl)-4-(3-nitrophenyl)-benzothiazol-2-yl amine. BA-01. A solution of compound (7) (32.5 mg, 0.066 mmol) was treated with Et$_3$SiH (500 uL, 3 mmol, 47 eq.). The mixture was stirred at room temperature for 130 min. until starting material XM-17 was consumed. The volatile material was removed under reduced pressure. The residue was washed with sodium bicarbonate solution, extracted with EtOAc (3×15 mL), dried. Evaporation gave a residue, which was purified chromatography on silica gel using dichloromethane/hexanes (1:1, 2:1, 3:1, 4:1, 20 mL each) followed by dichloromethane as eluent to give 21 mg of product, which

BA-01

(2,6-dibromo-4-cyano-phenyl)-thiourea (2). To a suspension of 4-amino-3,5-dibromobenzonitrile (11 g, 40 mmol) in toluene (80 ml) was added thiophosgene (5.06 g, 44 mmol, 1.1 eq.). The reaction mixture was stirred under reflux for 16 h. After cooling to RT, the volatile material was removed in-vacuo, residue was suspended in dioxane (80 mL) and treated with ammonium (27 w/w %, 9.85 g) with stirring at room temperature After for 30 min., dioxane was removed in-vacuo. The solid obtained was washed with ether (50 mL), water (50 mL) and ether (50 mL), dried in vacuo to provide 9.6 g (70% yield) of the title compound (2). $^1$H-NMR-(400 MHz, CDCl$_3$).

2-amino-4-bromo-benzothiazole-6-carbonitrile (3). A reaction mixture of (2) compound (1.3 g, 3.66 mmol), CuI (70 mg, 0.366 mmol, 0.1 eq.), 1,10-phenanthroline (70 mg, 0.366 mmol), and Cs$_2$CO$_3$ (1.8 g, 5.5 mmol, 1.5 eq.) in dioxane (20 mL) was stirred under reflux for 2 h under Ar. After cooling to room temperature, water (100 mL) was added; solid was filtered, washed with water (100 mL×3) followed by ether (50 contained impurities. The product thus obtained was triturated with hexanes to give 7.6 mg of desired product. BA-01. 1H NMR. LCMS: 99%.

In similar fashion the following schemes provide outlines of the syntheses as applied to examples.

BA-02

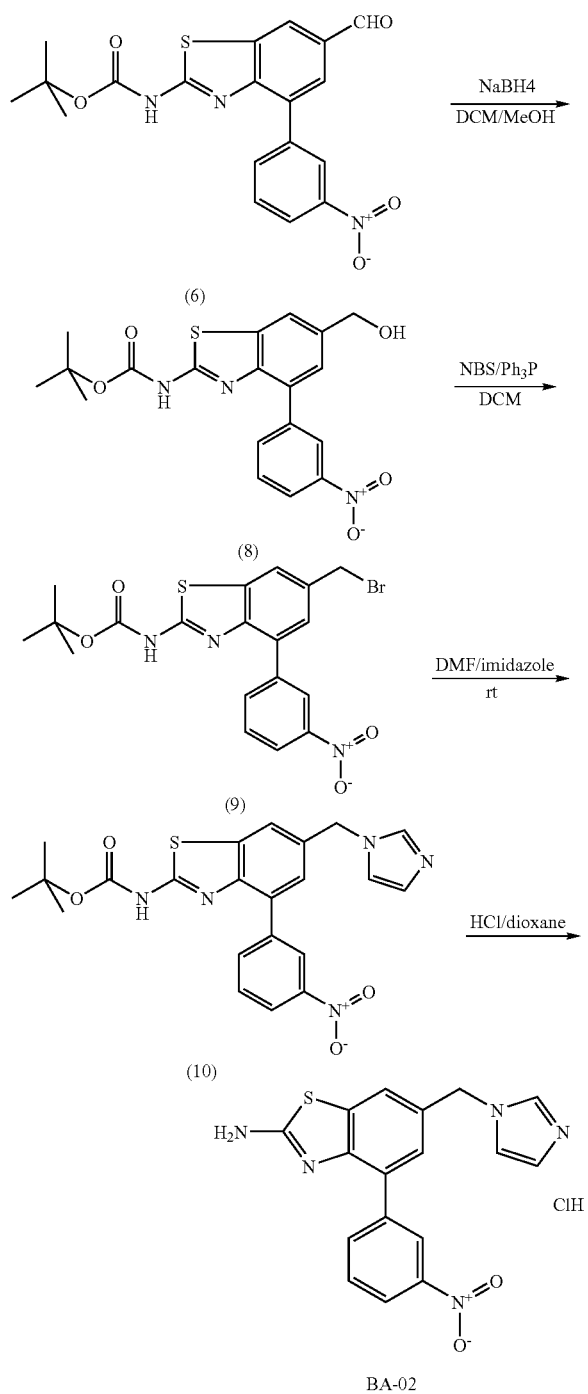

[6-Hydroxymethyl-4-(3-nitro-phenyl)-benzothiazol-2-yl]-carbamic acid tert-butyl ester. (8) To a solution of aldehyde (6) (2 g, 4.3 mmol, 1 eq) in a mixture of DCM (20 ml) and MeOH (10 ml) was added $NaBH_4$ (760 mg, 20 mmol, 5 eq.) portion-wise at 0° C. The mixture was stirred at 0 C~rt until starting material was consumed. The mixture was added sat. $NH_4Cl$ aq. (200 ml) and extracted with EtOAc (20 ml×3). The combined organic layers were dried over MgSO4. Removal of solvent under reduced pressure gave a residue, which was purified by chromatography on silica gel using DCM followed by DCM/MeOH with a ratio of 100:1 as eluent to give 500 mg of alcohol (8) in 29% yield.

[6-Bromomethyl-4-(3-nitro-phenyl)-benzothiazol-2-yl]-carbamic acid tert-butyl ester. (9). To a solution of (8) (500 mg, 1.25 mmol, 1 eq.) in DCM (12 ml) was added $Ph_3P$ (340 mg, 1.25 mmol, 1 eq.). After the mixture was stirred at rt for 20 min., NBS (230 mg, 1.25 mmol, 1 eq.) was added in one portion. The mixture was stirred at rt until (8) was consumed. The volatile material was removed under reduced pressure to afford a residue, which was purified by chromatography on silica gel using hexane/DCM (1:1 then 1:1.5) as eluent to give 126 mg of desired bromide (9) in 22% yield.

[6-imidazol-1-ylmethyl-4-(3-nitro-phenyl)-benzothiazol-2-yl]-carbamic acid tert-butyl ester. (10) To a 20 mL vial which contained (9) (46 mg, 0.13 mmol) in DMF (5 mL) was added imidazole (200 mg, excess) at 0° C. The reaction mixture was allowed to warm to rt and stir at rt for 16 h. The mixture was poured onto 30 mL ice-water which was extracted with ethyl acetate (3×20 mL), washed with water (2×20 mL), brine (20 mL) and dried over Na2SO4. After removal of solvent, the residue was purified by silica gel column chromatography with ethyl acetate/Hexane as eluent to give 28 mg of product (10) in 60% yield. $^1$H-NMR (400 MHz, $CDCl_3$)

6-imidazol-1-ylmethyl-4-(3-nitro-phenyl)-benzothiazol-2-ylamine HCl salt. BA-02. To a 20 mL vial which contained (10) (28 mg, 0.07 mmol) was added HCl (4 N in dioxane, 1 mL) at rt. The mixture was allowed to stir at it for 16 h. Diethyl ether (20 mL) was added and the solid which formed was filtered out, washed with diethyl ether (20 mL), dried to yield 23 mg (70%) of the title product BA-02. $^1$H-NMR (400 MHz, DMSO)

BA-03

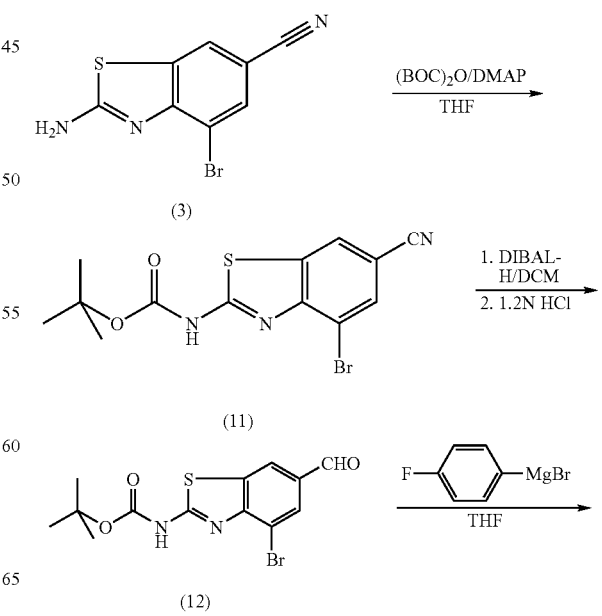

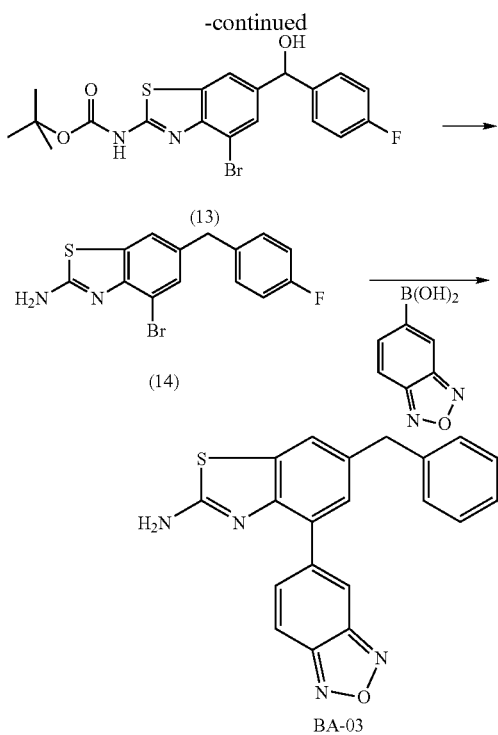

BA-03

(4-bromo-6-cyano-benzothiazol-2-yl)-carbamic acid tert-butyl ester (11). A reaction mixture of compound (3) (25 g, 100 mmol), (Boc)$_2$O (26.8 g, 123 mmol, 1.23 eq.) and DMAP (352 mg, 2.9 mmol, 0.03 eq.) in THF (260 mL) was stirred at room temperature over night. 5 g of additional of (Boc)$_2$O and 350 mg of DMAP was added and the resulting mixture was stirred for 48 h. The volatile material was removed under reduced pressure and the residue was purified by chromatography on silica gel (300 g, regular) using Hex/DCM (2:1 then 1:1) as eluent to give the product (24 g), which was further triturated with hexane to give the desired product (11) (20 g, 56% yield). as light yellow solid. $^1$H-NMR (400 MHz, CDCl$_3$)

(4-bromo-6-formyl-benzothiazol-2-yl)-carbamic acid tert-butyl ester. (12). To a solution of compound (11) (10 g, 28 mmol) in dichloromethane (200 mL) was added DIBAL-H (84 mL, 1N in hexane, 3 eq.) dropwise using a addition funnel keeping the temperature around 0° C. After the addition was complete, the reaction mixture was stirred at room temperature over night. The reaction mixture was poured into 1.2 N HCl (200 ml) with stirring. The yellow precipitate was collected by filtration and washed with water (3.65 g of de-Boc product was obtained). The mother liquid was separated and dried over Na$_2$SO$_4$. Removal of solvent gave the crude desired product (12) (4.5 g, 45% yield). The compound thus obtained was used next step without any further purification. 1H-NMR (400 MHz, DMSO-d6) MS (ESI+): 301.7 (M+1)

{4-bromo-6-[(4-fluoro-phenyl)-hydroxy-methyl]-benzothiazol-2-yl}-carbamic acid tert-butyl ester. (13). To a solution of the aldehyde (12) (4.5 g, 10 mmol) in anhydrous THF (200 mL) was added dropwise a solution of 4-fluorophenyl magnesium bromide in THF (30 ml, 1N) at −50° C. After the addition was complete, the resulting mixture was allowed to warm to room temperature over night. Then saturated NH$_4$Cl aq. was added. The mixture was extracted with EtOAc (3×20 ml). The combined organic layers were dried over Na$_2$SO$_4$. Removal of solvent gave a residue, which was purified by chromatography on silica gel (100 g, regular) using DCM/hexane (1:2 to 3:1) followed by DCM as eluents to give the recovered starting aldehyde (12) (1.7 g) and the desired product (13) (0.82 g, 25% yield).

4-bromo-6-(4-fluorobenzyl)-benzothiazol-2-yl amine. (14). To a solution of compound (13) (205 mg, 0.45 mmol) in TFA (3 ml) was added Et$_3$SiH (1 mL, 6.25 mmol, 14 eq.) in one portion. The mixture was stirred at room temperature over night. The volatile material was removed under reduced pressure. The residue was triturated with DCM/hexane (1:5). After drying, the desired product (14) was obtained as light yellow solid (145 mg, 96% yield).

4-Benzol[1,2,5]oxadiazol-5-yl-6-(4-fluoro-benzyl)-benzothiazol-2-yl amine. BA-03. A mixture of compound (14) (118 mg, 0.35 mmol), the boronic acid (86 mg, 0.52 mmol, 1.5 eq.), triphenylphosphine (70 mg, 0.26 mmol, 0.6 eq.), Pd(OAc)$_2$ (20 mg, 0.09 mmol, 0.2 eq.) in dioxane (4 mL), and (aqueous) 1N Na$_2$CO$_3$ (1 mL, 3 eq.) was stirred under reflux overnight under Ar. After cooling to room temperature, The volatile material was removed under reduced pressure to give a residue, which was purified by chromatography on silica gel using DCM/hexane (1:1) followed by DCM as eluent to afford the product (20 mg), which was further triturated with DCM/hexane (1:1) to give the desired product BA-03 (13.5 mg, 10% yield). 1H-NMR (400 MHz, DMSO-d6) MS (ESI+): 301.7 (M+1) LC-MS: 96.8%.

BA-04

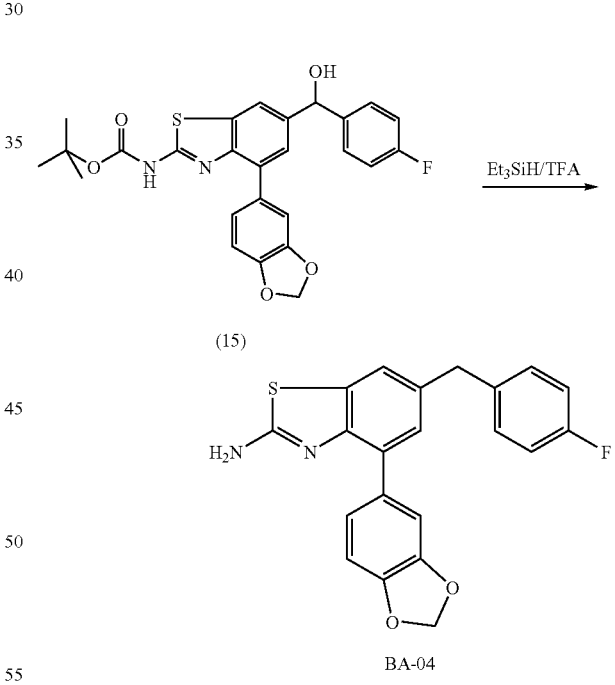

BA-04

4-Benzo[1,3]dioxol-5-yl-6-(4-fluoro-benzyl)-benzothiazol-2-ylamine. BA-04. To a mixture of compound (15) (100 mg, 0.2 mmol) in TFA (2 ml) was added Et$_3$SiH (0.5 ml, 15 eq.) in one portion by a syringe. The mixture was stirred at room temperature over night. The volatile material was removed under reduced pressure. The residue was washed with hexane and then purified by chromatography on silica gel using dichloromethane followed by dichloromethane/methanol (200:1) as eluent to give the desired product, which was triturated with hexane/dichloromethane (10:1) to give the desired product BA-04 (31 mg, 41% yield). 1H-NMR (400 MHz, DMSO-d6) MS (ESI+): (M+1) LC-MS: 99%.

BA-05

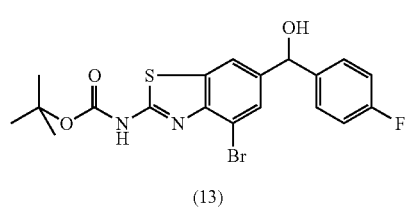

(13)

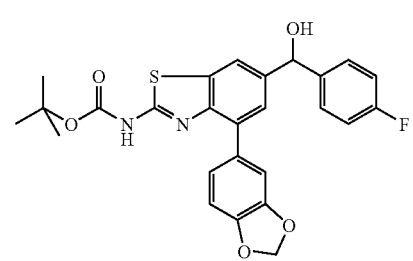

(15)

BA-05

[4-Benzo[1,3]dioxol-5-yl-6-[(4-fluoro-phenyl)-hydroxy-ethyl]-benzothiazol-2-yl]-carbamic acid tert-butylester. (15). A mixture of compound (13) (316 mg, 0.7 mmol), the boronic acid (175 mg, 1.05 mmol, 1.5 eq.), triphenylphosphine (120 mg, 0.42 mmol, 0.6 eq.), Pd(OAc)₂ (40 mg, 0.14 mmol, 0.2 eq.) in dioxane (9 mL), and (aqueous) 1N Na₂CO₃ (3 mL, 3 eq.) was stirred under reflux overnight under Ar. After cooling to room temperature, The volatile material was removed under reduced pressure to give a residue, which was purified by chromatography on silica gel using hexane/dichloromethane (from 2:1 to 1:5) followed by DCM as eluent to afford the product (15) (236 mg, 68% yield).

(2-Amino-4-benzo[1,3]dioxol-5-yl-benzothiazol-6-yl)-(4-fluoro-phenyl)-methanol. BA-05. Compound (15) (70 mg, 0.14 mmol) in dichloromethane (1 ml) was added TFA (0.6 ml). The mixture was stirred at room temperature over night. The volatile material was removed under reduced pressure. The residue was purified by chromatography on silica gel using dichloromethane followed by dichloromethane/methanol (100:1) as eluent to give the desired product BA-05 (18.5 mg, 34% yield) as gray solid. 1H-NMR (400 MHz, DMSO-d6) MS (ESI+): (M+1) LC-MS: 95%.

BA-06

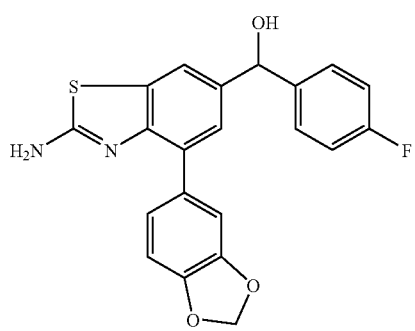

(17)

BA-06

{4-Bromo-6-[hydroxy-(2-methyl-2H-pyrazol-3-yl)-methyl]-benzothiazol-2-yl}-carbamic acid tert-butyl ester. (16). To a solution of 1-methylpyrazole (1.13 g, 13.8 mmol) in THF (20 ml) at −78° C. was added n-BuLi (2.5 N in hexane, 4 ml) dropwise by a syringe. The resulting mixture was stirred at −78° C.~rt over 1.5 h. The solution was stored at a refrigerator for further use. To a solution of aldehyde (12) (357 mg, 1 mmol) in THF (10 ml) was added dropwise above prepared lithium reagent (8 ml, 3.2 mmol, 1.6 eq.) by a syringe at −58° C. with stirring. After the addition was complete, the mixture was allowed to warm to room temperature over 2 h. The mixture was added to aqueous NH₄Cl solution and extracted with ethyl acetate. The organic layers were separated and dried over MgSO4. Removal of solvent gave a residue, which was purified by chromatography on silica gel using DCM/MeOH (100:1) as eluent to give the desired product (16) (416 mg, 95% yield).

{4-Benzo[1,3]dioxol-5-yl-6-[hydroxy-(2-methyl-2H-pyrazol-3-yl)-methyl]-benzothiazol-2-yl}-carbamic acid tert-butyl ester. (17). A mixture of (16) (206 mg, 0.47 mmol), boronic acid (120 mg, 0.705 mmol, 1.5 eq.), Pd(OAc)₂ (21 mg, 0.098 mmol, 0.2 eq.), PPh₃ (75 mg, 0.282 mmol, 0.6 eq.)

in 1N Na$_2$CO$_3$ (2 ml) and dioxane (6 ml) was stirred at 100° C. (oil bath) under Ar over night. After cooling to room temperature, the volatile material was removed and the residue was partitioned between ethyl acetate and water. The EA layer was separated and passed through a plug of MgSO$_4$. Solvent was removed to give crude product (17) (260 mg, 115% yield). No further purification was done.

(2-Amino-4-benzo[1,3]dioxol-5-yl-benzothiazol-6-yl)-(2-methyl-2H-pyrazol-3-yl)-methanol. BA-06. To a solution of compound (17) (260 mg, 0.47 mmol) in TFA (1 ml) was added Et$_3$SiH (1 ml, 6 mmol, 30 eq.) in one portion by a syringe. The mixture was stirred at room temperature over night. The volatile material was removed under reduced pressure. The residue was washed with hexane and then purified by chromatography on silica gel using dichloromethane/methanol (100:1) as eluent to give the desired product BA-06 (43 mg, 25% yield). 1H-NMR (400 MHz, DMSO-d6); MS (ESI+): (M+1), LC-MS: 97%.

BA-07

6-(4-Fluoro-benzyl)-4-(3-trifluoromethyl-phenyl)-benzothiazol-2-ylamine. BA-07. To a solution of compound (18) (91 mg, 0.17 mmol) in TFA (0.5 ml) was added Et$_3$SiH (0.5 ml). The mixture was stirred at room temperature over night. The volatile material was removed under reduced pressure. The residue was triturated with hexane. The solid was filtered and washed with hexane. After dried, 60 mg of desired product was obtained. the product thus obtained was passed through a plug of silica gel using dichloromethane/methanol (100:1) as eluent to afford the desired product BA-07 (50 mg, 73% yield). 1H-NMR (400 MHz, DMSO-d6); MS (ESI+): (M+1), LC-MS: 100%.

BA-08

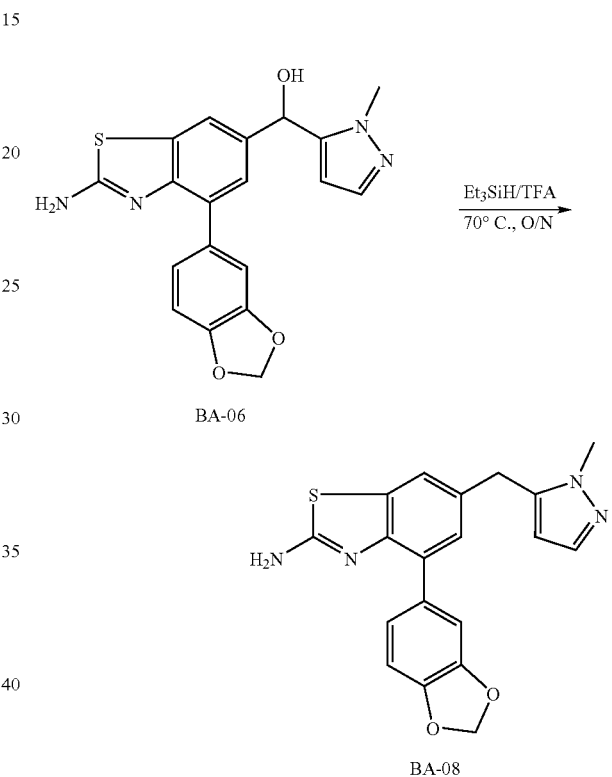

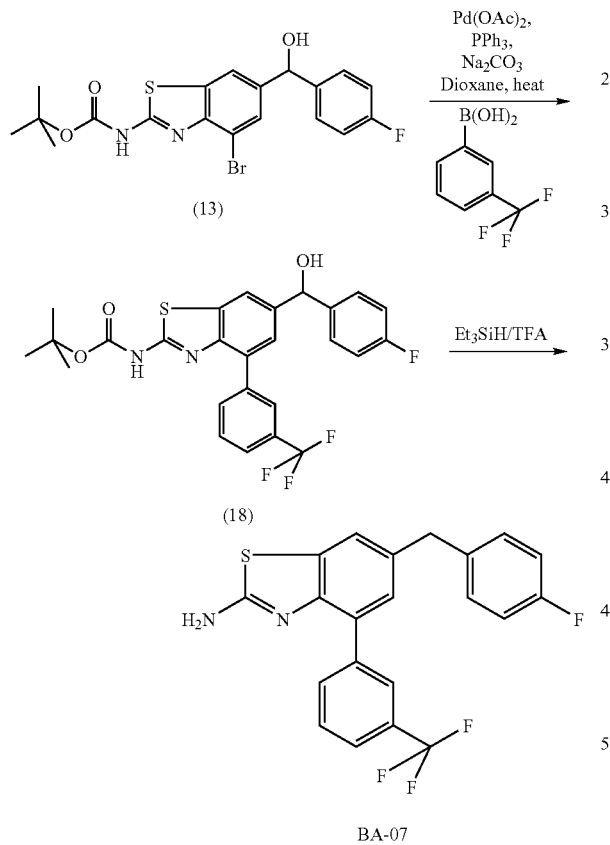

4-Benzo[1,3]dioxol-5-yl-6-(2-methyl-2H-pyrazol-3-ylmethyl)-benzothiazol-2-ylamine. BA-08. Compound BA-06 (20 mg, 0.05 mmol) was treated with a mixture of TFA (ml) and Et$_3$SiH (1 ml) at 70° C. with stirring over night. After cooling to room temperature, the volatile material was removed under reduced pressure to give a residue, which was purified by chromatography on silica gel using dichloromethane/methanol with a ratio of 100:1 as eluent to give the desired product BA-08 (15 mg, 76% yield). 1H-NMR (400 MHz, DMSO-d6) MS (ESI+): (M+1) LC-MS: 93%.

[6-[(4-Fluoro-phenyl)-hydroxy-methyl]-4-(3-trifluoromethyl-phenyl)-benzothiazol-2-yl]-carbamic acid tert-butyl ester. (18) A mixture of compound (13) (170 mg, 0.375 mmol), the boronic acid (110 mg, 0.563 mmol, 1.5 eq.), triphenylphosphine (60 mg, 0.225 mmol, 0.6 eq.), Pd(OAc)$_2$ (20 mg, 0.075 mmol, 0.2 eq.) in dioxane (6 mL), and (aqueous) 1N Na$_2$CO$_3$ (2 mL, 3 eq.) was stirred under reflux overnight under Ar. After cooling to room temperature, The volatile material was removed under reduced pressure to give a residue, which was purified by chromatography on silica gel using dichloromethane/methanol with a ratio of 100:1 as eluent to afford the product (18) (136 mg, 70% yield).

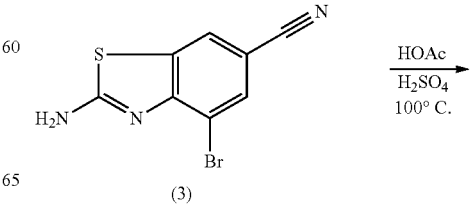

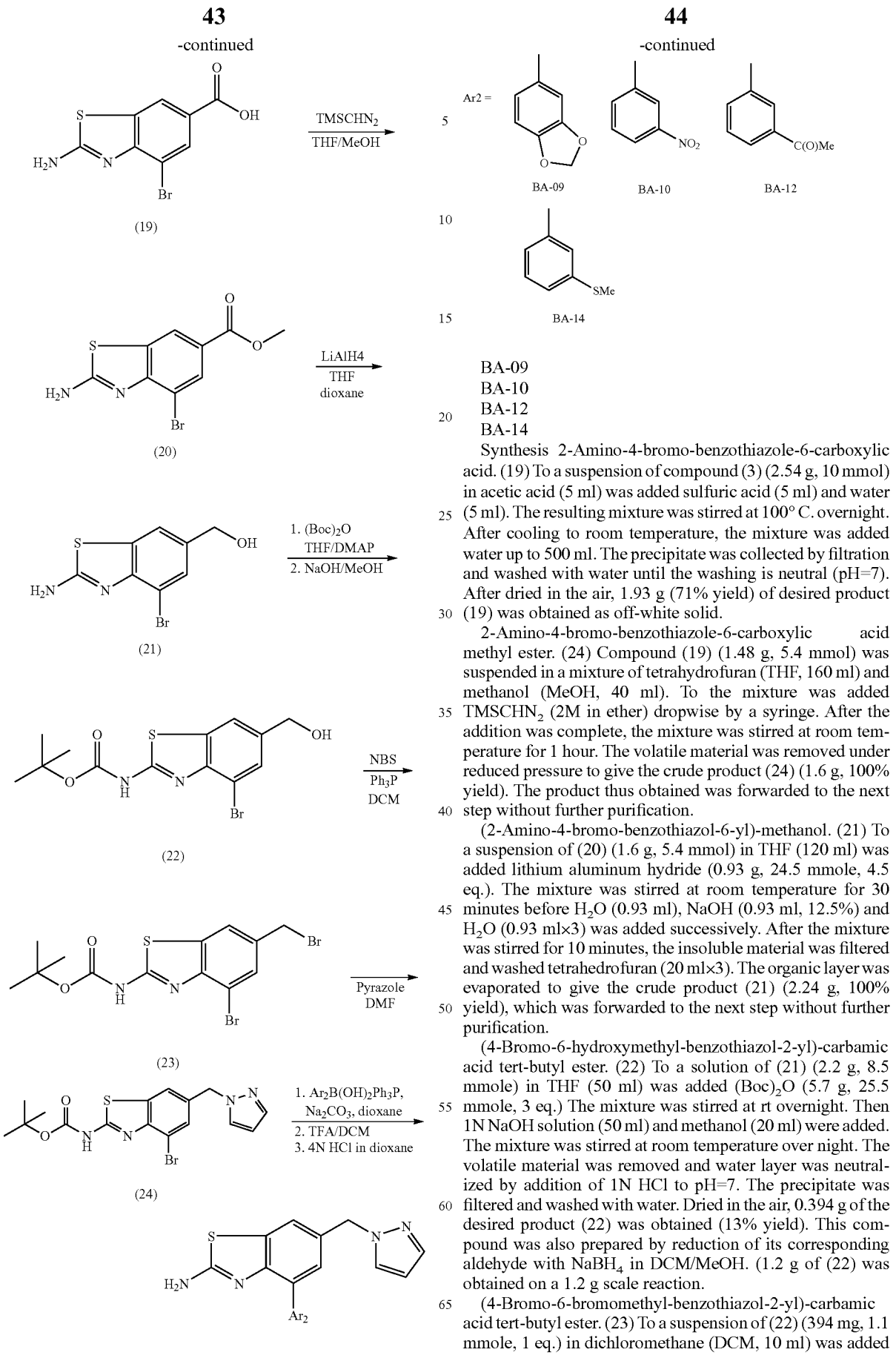

Synthesis 2-Amino-4-bromo-benzothiazole-6-carboxylic acid. (19) To a suspension of compound (3) (2.54 g, 10 mmol) in acetic acid (5 ml) was added sulfuric acid (5 ml) and water (5 ml). The resulting mixture was stirred at 100° C. overnight. After cooling to room temperature, the mixture was added water up to 500 ml. The precipitate was collected by filtration and washed with water until the washing is neutral (pH=7). After dried in the air, 1.93 g (71% yield) of desired product (19) was obtained as off-white solid.

2-Amino-4-bromo-benzothiazole-6-carboxylic acid methyl ester. (24) Compound (19) (1.48 g, 5.4 mmol) was suspended in a mixture of tetrahydrofuran (THF, 160 ml) and methanol (MeOH, 40 ml). To the mixture was added TMSCHN$_2$ (2M in ether) dropwise by a syringe. After the addition was complete, the mixture was stirred at room temperature for 1 hour. The volatile material was removed under reduced pressure to give the crude product (24) (1.6 g, 100% yield). The product thus obtained was forwarded to the next step without further purification.

(2-Amino-4-bromo-benzothiazol-6-yl)-methanol. (21) To a suspension of (20) (1.6 g, 5.4 mmol) in THF (120 ml) was added lithium aluminum hydride (0.93 g, 24.5 mmole, 4.5 eq.). The mixture was stirred at room temperature for 30 minutes before H$_2$O (0.93 ml), NaOH (0.93 ml, 12.5%) and H$_2$O (0.93 ml×3) was added successively. After the mixture was stirred for 10 minutes, the insoluble material was filtered and washed tetrahedrofuran (20 ml×3). The organic layer was evaporated to give the crude product (21) (2.24 g, 100% yield), which was forwarded to the next step without further purification.

(4-Bromo-6-hydroxymethyl-benzothiazol-2-yl)-carbamic acid tert-butyl ester. (22) To a solution of (21) (2.2 g, 8.5 mmole) in THF (50 ml) was added (Boc)$_2$O (5.7 g, 25.5 mmole, 3 eq.) The mixture was stirred at rt overnight. Then 1N NaOH solution (50 ml) and methanol (20 ml) were added. The mixture was stirred at room temperature over night. The volatile material was removed and water layer was neutralized by addition of 1N HCl to pH=7. The precipitate was filtered and washed with water. Dried in the air, 0.394 g of the desired product (22) was obtained (13% yield). This compound was also prepared by reduction of its corresponding aldehyde with NaBH$_4$ in DCM/MeOH. (1.2 g of (22) was obtained on a 1.2 g scale reaction.

(4-Bromo-6-bromomethyl-benzothiazol-2-yl)-carbamic acid tert-butyl ester. (23) To a suspension of (22) (394 mg, 1.1 mmole, 1 eq.) in dichloromethane (DCM, 10 ml) was added triphenylphosphine (390 mg, 1.1 mmole, 1 eq.) followed by NBS (200 mg, 1.1 mmole, 1.0 eq.) in one portion. The mixture was stirred 0° C. for 2 hours. The volatile material was removed and the residue was purified by chromatography on silica gel using DCM/Methanol (200:1) as eluent to give 200 mg of desired product (23) (43% yield) along with 100 mg of recovered starting (22) (25%). In a 1.2 scale reaction under the same condition described above, 936 mg of desired product (23) was isolated in 67% yield.

(4-Bromo-6-pyrazol-1-ylmethyl-benzothiazol-2-yl)-carbamic acid tert-butyl ester. (24) To a solution of (23) (1.5 g, 3.6 mmole, 1 eq.) in DMF (8 ml) was added pyrazole (1.5 g, 21 mmole, 6 eq.). The resulting mixture was stirred at room temperature until SM was consumed. The mixture was poured into water and the precipitate was filtered and washed with water. The product was dried under $N_2$ flow over night, the solid was purified by chromatography on silica gel using DCM as eluent to give 925 mg of product (24) in 63% yield.

General procedure A: Suzuki coupling of (24) with boronic acids: Examples BA-09, BA-10, BA-12 and BA-14.

A mixture of compound (24) (1 eq.), boronic acid (1.5 eq.), triphenylphosphine (0.6 eq.), Pd(OAc)$_2$ (0.2 eq.) in dioxane (6× mL), and (aqueous) 1N Na$_2$CO$_3$ (X mL, 3 eq.) was stirred under Ar at 80° C. overnight. The reaction mixture was diluted with water and extracted with ethyl acetate. The combined organic phase was passed through a filtration funnel. Evaporation of solvent gave a residue, which was purified by chromatography on silica gel using DCM/MeOH (100:1) as eluent to give desired coupling product. Removal of Boc group was effected by treatment of Suzuki coupling product with TFA/DCM (1:1). Volatile material was removed and the residue was treated with 2N HCl in ether to give target compounds, Examples 003, 011, 012 and 014 as HCl salt.

BA-09. 4-Benzo[1,3]dioxol-5-yl-6-pyrazol-1-ylmethyl-benzothiazol-2-ylamine Started with 70 mg of (24), 34.7 mg of BA-09 was obtained. LC-MS: 97.6%.

BA-10. 4-(3-Nitro-phenyl)-6-pyrazol-1-ylmethyl-benzothiazol-2-ylamine. Started with 90 mg of (24), 35 mg of BA-10 was obtained. LC-MS: 93%.

BA-12. 1-[3-(2-Amino-6-pyrazol-1-ylmethyl-benzothiazol-4-yl)-phenyl]-ethanone Started with 120 mg of (24), 93.7 mg of BA-12 was obtained. LC-MS: 94%.

BA-14. 4-(3-Methylsulfanyl-phenyl)-6-pyrazol-1-ylmethyl-benzothiazol-2-ylamine Started with 120 mg of (24), 60 mg of BA-14 was obtained. LC-MS: 99%.

BA-11

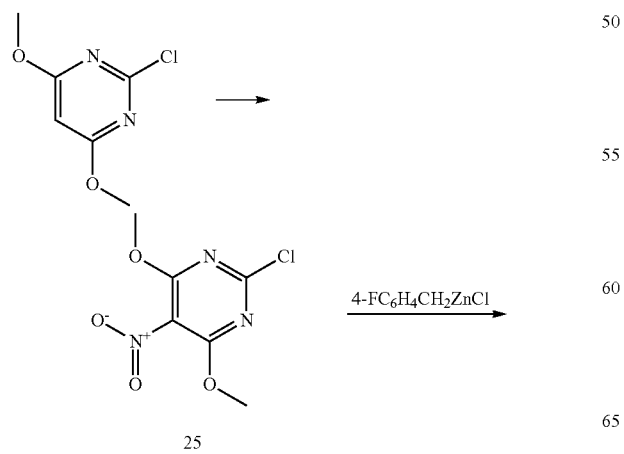

25

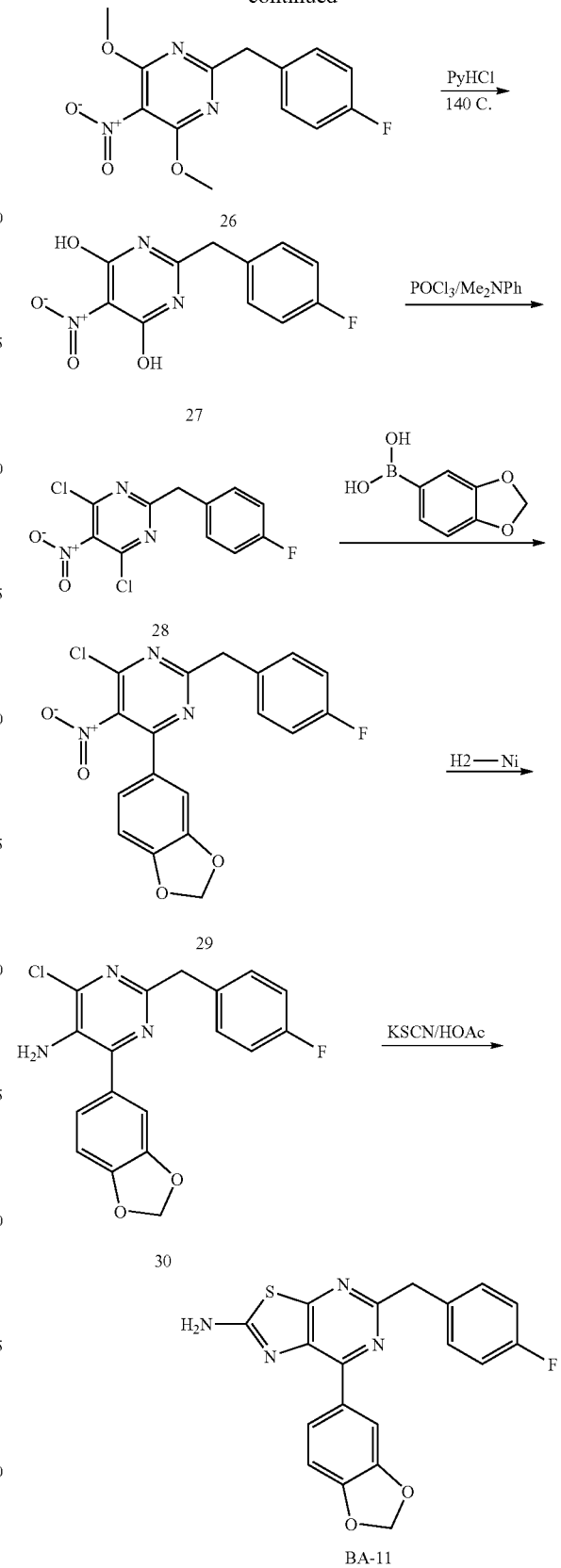

2-Chloro-4,6-dimethoxy-5-nitro-pyrimidine. (25) To a suspended tetramethyl-ammonium nitrate (11.2 g, 39.5 mmol) in methylene chloride (100 mL) was added triflic anhydride (5.4 g, 39.5 mmol), and stirred at room temperature for 2 hour. After the resultant was cooled to −78° C., a solution of 2-chloro-4,6-dimethoxypyrimidine (5.0 g, 36.0 mmol) in methylene chloride (50 mL) was added at −78° C., and continued to stirred at room temperature for 24 hours. The reaction was diluted with brine, extracted with ethyl acetate, washed with brine, dried over $Na_2SO_4$, concentrated to yield 2-chloro-4,6-dimethoxy-5-nitro-pyrimidine (25) (6.0 g, 76%). 1HNMR (DMSO-d6)

2-(4-Fluoro-benzyl)-4,6-dimethoxy-5-nitro-pyrimidine. (26) A solution of compound (25) (1.2 g, 5.5 mmol), 4-fluorobenzylzinc chloride (13.1 mL, 0.5 M in THF, 6.6 mmol), tetrakis(triphenylphosphine)palladium (0.13 g, 0.1 mmol) in THF (50 mL) was heated to reflux for 3 hours under nitrogen. After it cooled to room temperature, the THF was removed in vacuo. The residue was diluted with ethyl acetate, washed with water and brine, dried over $Na_2SO_4$. After concentrated, the residue was purified by a column chromatography on silica gel eluting with 5% ethyl acetate in hexane to yield 2-(4-fluoro-benzyl)-4,6-dimethoxy-5-nitro-pyrimidine (26) (1.1 g, 63%). 1H NMR ($CDCl_3$)

2-(4-Fluoro-benzyl)-5-nitro-pyrimidine-4,6-diol. (27) A mixture of compound (26) (1.0 g, 3.4 mmol) and pyridine hydrochloride (3.9 g, 34 mmol) was heated to 140 C for 1 hour. After it cooled to room temperature, the resultant was diluted with water. The product was collected on a filter and dried in vacuo. 2-(4-Fluoro-benzyl)-5-nitro-pyrimidine-4,6-diol (27) was obtained in a yield of 62% (1.1 g). 1H NMR (DMSO-$d_6$)

4,6-Dichloro-2-(4-fluoro-benzyl)-5-nitro-pyrimidine. (28) To a mixture of compound (27) (0.7 g, 2.6 mmol) in phosphorus oxylchloride (3 mL) was added N,N-dimethylaniline (0.42 g, 3.4 mmol), and heated refluxed for 2 hours. After it cooled to room temperature, the reaction resultant was poured into ice-water and stirred for 5 minutes. The mixture was extracted with ethyl acetate, washed brine, dried over $Na_2SO_4$, concentrated to yield (28) (0.5 g, 62%). 1 HNMR ($CDCl_3$)

4-Benzo[1,3]dioxol-5-yl-6-chloro-2-(4-fluorobenzyl)-5-nitro-pyrimidine. (29) A solution of compound (28) (0.1 g, 3.3 mmol), 3,4-methylenedioxyphenyl-boronic acid (49 mg, 0.29 mmol), sodium carbonate (0.11 g, 0.1 mmol) and tetrakis(triphenyl-phosphine)palladium (0.13 g, 0.1 mmol) in Ttoluene/water (1:1, 4 mL) was heated to reflux for 3 hours under nitrogen. After it cooled to room temperature, the THF was removed in vacuo. The residue was diluted with ethyl acetate, washed with water and brine, dried over $Na_2SO_4$. After concentrated, the residue was purified by a column chromatography on silica gel eluting with 5% ethyl acetate in hexane to yield (29) (0.12 g, 90%). 1HNMR ($CDCl_3$)

4-Benzo[1,3]dioxol-5-yl-6-chloro-2-(4-fluoro-benzyl)-pyrimidin-5-ylamine. (30) A mixture of compound (29) (0.12 g, 0.31 mmol) in ethanol (5 mL) was added Raney nickel (0.05 g), and hydrogenated under 50 Psi for 2 hours. After the catalyst was filtered off, the solution was concentrated to yield (30) (0.1 g, 90%). 1HNMR ($CDCl_3$)

7-Benzo[1,3]dioxol-5-yl-5-(4-fluorobenzyl)-thiazolo[5,4-d]pyrimidin-2-ylamine. BA-11 To a solution of compound (30) (0.1 g, 0.28 mmol) in acetic acid (1 mL) was added potassium thioocynate (27 mg, 0.29 mmol). The mixture was heated at 60° C. for 16 hours. After it cooled to room temperature, the reaction mixture was diluted with water, extracted with ethyl acetate, washed with water and brine, dried over $Na_2SO_4$. After concentrated, the residue was purified by a column chromatography on silica gel eluting with 20% ethyl acetate in hexane to yield BA-11 (33 mg, 30%). 1HNMR (DMSO-$d_6$). LC/MS: 99%

BA-13

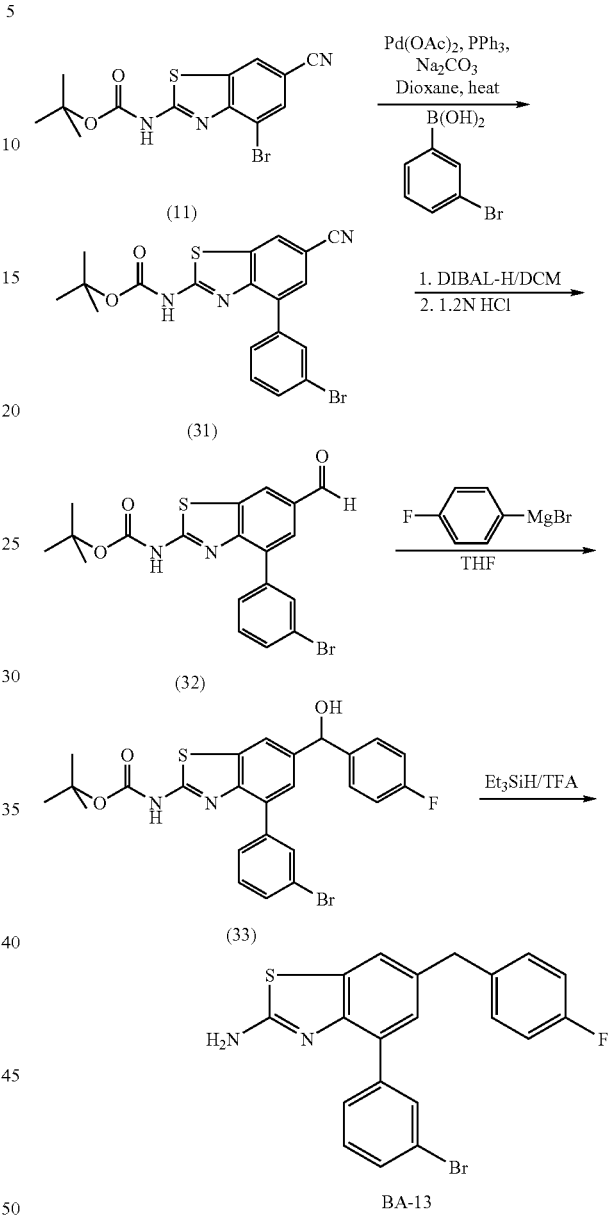

(4-bromo-6-cyano-benzothiazol-2-yl)-carbamic acid tert-butyl ester. (11) See BA-03.

[4-(3-Bromo-phenyl)-6-cyano-benzothiazol-2-yl]-carbamic acid tert-butyl ester. (31) A reaction mixture of compound (11) (1.23 g, 3 mmole, 3 eq.), the boronic acid (200 mg, 1 mmol, 1 eq.), triphenylphosphine (80 mg, 0.3 mmol, 0.3 eq.), Pd(OAc)$_2$ (22 mg, 0.1 mmol, 0.1 eq.) in dioxane (20 mL), and (aqueous) 1N $Na_2CO_3$ (6 mL, 6 eq.) was stirred under reflux overnight under Ar. Only very small amount of less polar product was formed. 0.2 eq of additional of Pd(OAc)$_2$ (44 mg) and 0.6 eq. of Ph$_3$P (160 mg) were added. The resulting mixture was stirred at 85° C. for 6 hours. After cooling to room temperature, The volatile material was removed under reduced pressure to give a residue, which was purified by chromatography on silica gel using DCM/hexane (3:1) as eluent to afford the product (31) (262 mg, 61% yield) along with (11) (560 mg). $^1$H-NMR (400 MHz, CDCl$_3$).

[4-(3-Bromo-phenyl)-6-formyl-benzothiazol-2-yl]-carbamic acid tert-butyl ester (32) To a solution of compound (31) (242 mg, 0.56 mmol, 1 eq.) in dichloromethane (10 mL) was added DIBAL-H (2 mL, 1N in hexane, 3 eq.) dropwise by a syringe at −78° C. After the addition was complete, the reaction mixture was stirred at room temperature over night. The reaction mixture was poured into 1 N HCl (5 ml) with stirring at 0° C. The mixture was extracted with DCM. DCM layer was separated and dried over MgSO$_4$. Removal of solvent gave a residue, which was purified by chromatography on silica gel using DCM/hex as eluent to give desired product (32) (54.8 mg, 23% yield). 1H-NMR (400 MHz, DMSO-d6). MS (ESI+): 301.7 (M+1)

[4-(3-Bromo-phenyl)-6-[(4-fluoro-phenyl)-hydroxy-methyl]-benzothiazol-2-yl]-carbamic acid tert-butyl ester. (33) To a solution of the aldehyde (32) (55 mg, 0.13 mmol, 1 eq.) in anhydrous THF (4 mL) was added dropwise a solution of 4-fluorophenyl magnesium bromide in THF (0.8 ml, 1N, 3 eq.) at −78° C. After the addition was complete, the resulting mixture was allowed to warm to room temperature over night. Then saturated NH$_4$Cl aq. was added. The mixture was extracted with EtOAc (3×5 ml). The combined organic layers were dried over Na$_2$SO$_4$. Removal of solvent gave a residue, which was purified by chromatography on silica gel using DCM/MeOH (200:1) to give the desired product (33) (24 mg, 35% yield).

4-(3-bromophenyl)-6-(4-fluorobenzyl)-1,3-benzothiazol-2-amine. BA-13. Compound (33) (24 mg, 0.045 mmol) was treated with Et$_3$SiH (0.8 mL, 3 mmol, 100 eq.) in TFA (0.8 ml). The mixture was stirred at room temperature for 130 min. until starting material XM-45 was consumed. The volatile material was removed under reduced pressure. The residue was washed with sodium bicarbonate solution, extracted with EtOAc (3×15 mL), dried. Evaporation gave a residue, which was purified by chromatography on prep. TLC plate using dichloromethane/hexanes (1:1) as developing system to give 20 mg of XM-46, which was passed through a plug of silica gel using DCM/hexane (1:1) followed by dichloromethane as eluent to give BA-13 (12 mg, 65% yield). 1H NMR. LCMS: 99%.

BA-15

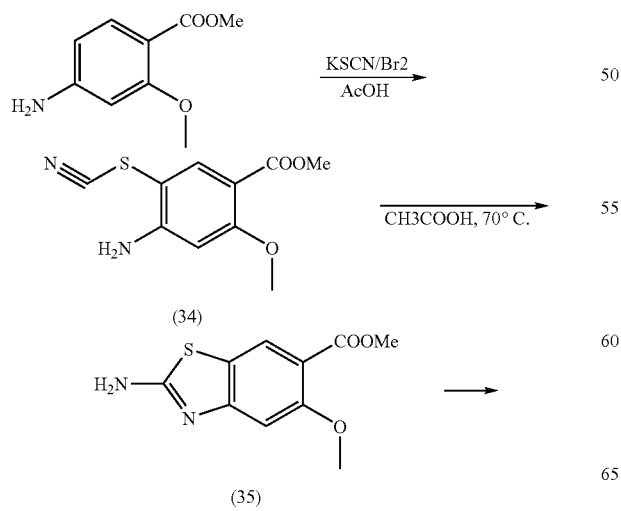

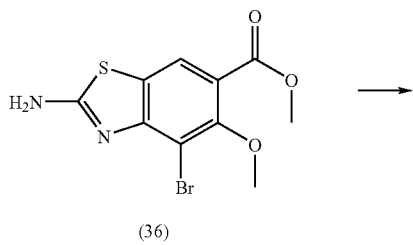

(36)

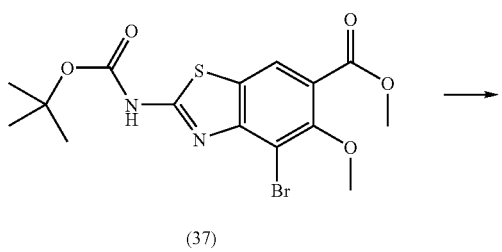

(37)

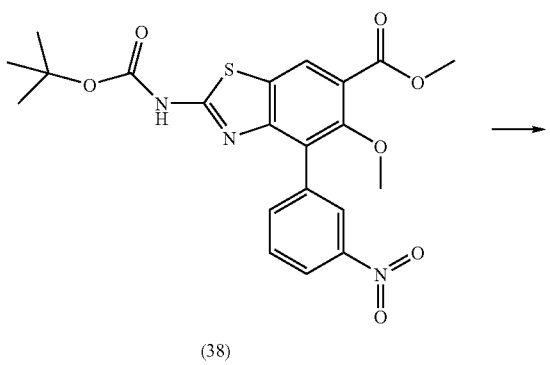

(38)

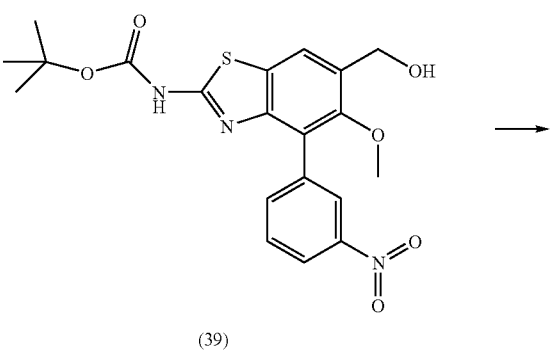

(39)

(40)

-continued

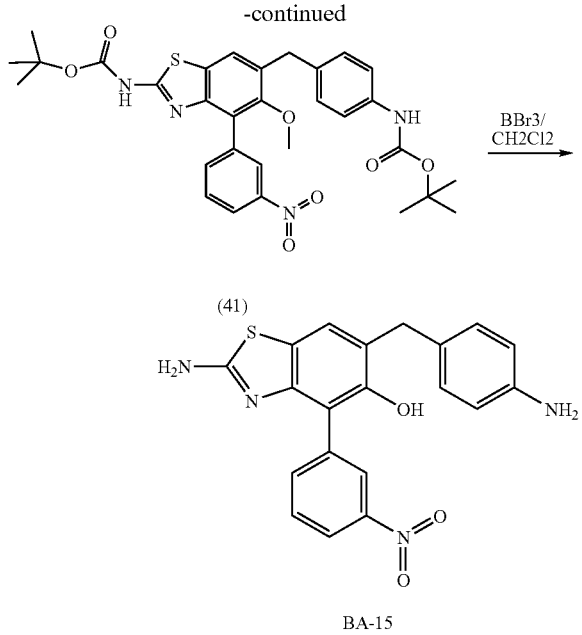

BA-15

2-Amino-5-methoxy-benzothiazole-6-carboxylic acid methyl ester. (35) To a suspension of methyl-4-amino-2-methoxybenzoate (3 g, 16.55 mmole), potassium thiocyanate (6.45 g, 66.23 mmole) in 30 ml acetic acid was added bromine at room temperature (2.65 g, 16.55 mmole). During the bromine addition suspension became solution, and then a precipitate formed. The reaction mixture was stirred at room temperature, overnight. A sample (1 ml) was taken and concentrated, submitted for H NMR. This showed the intermediate (34). The suspension was then heated at 60° C., overnight. The suspension was concentrated, the solid was taken into a mixture of 50% saturated NaHCO3 sol./water (50 ml) and stirred for 30 minutes. The suspension was filtered, the solid was washed with water and dried to afford (35) 3.2 g (82% yield). $^1$H-NMR-(400 MHz, DMSO)

2-Amino-4-bromo-5-methoxy-benzothiazole-6-carboxylic acid methyl ester. (36) A suspension of (35) (1.1 g, 4.62 mmole) in 15 ml acetic acid was heated at 70° C., when a solution of bromine (1.3 g, 8.08 mmole) in 5 ml acetic acid was added. The suspension became solution during bromine addition, then a solid precipitated out. The reaction mixture was heated at 70° C. for 4 hours. The mixture was concentrated to dryness, the residue was taken into 50 ml mixture of 1:1=saturated NaHCO3/water, stirred for one hour, the suspension was filtered, solid was washed with water, dried to give 1.4 g product (36). $^1$H-NMR-(400 MHz, DMSO)

4-Bromo-2-tert-butoxycarbonylamino-5-methoxy-benzothiazole-6-carboxylic acid methyl ester. (37). To a suspension of (36) (1.3 g, 4.1 mmole), DMAP (500 mg, 4.1 mmloe) in 40 ml methylene chloride, was added at room temperature (Boc)$_2$O (1.075 g, 4.92 mmole). The reaction mixture was stirred at rt overnight. Mixture was concentrated down, diluted with 100 ml ethyl acetate and washed with water, 10% HCl solution, water and brine, dried over sodium sulfate, filtered, concentrated to give 1.5 g brown solid. Trituration with a mixture of 5% methanol/ether afforded 1.3 g (37). $^1$H-NMR-(400 MHz, DMSO)

2-tert-Butoxycarbonylamino-5-methoxy-4-(3-nitro-phenyl)-benzothiazole-6-carboxylic acid methyl ester. (38) A suspension of (37) (1.3 g, 3.11 mmole), sodium carbonate (990 mg, 9.33 mmole), 3-nitrophenyl boronic acid (778 mg, 4.665 mmole) in 50 ml dry dioxane was degassed for 10 min using argon, then palladium acetate (140 mg, 0.622 mmole) and triphenyl phosphine (490 mg, 1.86 mmole) were added and the mixture was heated at 95° C. for 24 hours. The reaction mixture was cooled to room temperature, diluted with 50 ml water and extracted with ethylacetate (3×60 ml). Combined organic layers were washed with water, brine, dried over sodium sulfate, filtered and concentrated. The residue was purified by column chromatography using 10% to 15% ethyl acetate in hexane to obtain 330 mg product (38) and 452 mg unreacted (37). $^1$H-NMR-(400 MHz, CDCl$_3$)

[6-Hydroxymethyl-5-methoxy-4-(3-nitro-phenyl)-benzothiazol-2-yl]-carbamic acid tert-butyl ester. (39). To a solution of (38) (326 mg, 0.71 mmole) in 8 ml dry THF was added at 0° C. 1.1 ml lithium borohydride (2M solution in THF). The reaction mixture was stirred at room temperature overnight. The reaction mixture was cooled to 0° C. and quenched with 0.5% HCl solution to a pH=6, then extracted with ethyl acetate (3×20 ml). Combined organic layers were washed with water, brine, dried over sodium sulfate, filtrated and concentrated to give the crude, which was purified by column chromatography using 20% to 30% ethylacetate/hexane. 180 mg (39) was obtained. $^1$H-NMR-(400 MHz, CDCl$_3$)

[6-(Diethoxy-phosphoryloxymethyl)-5-methoxy-4-(3-nitro-phenyl)-benzothiazol-2-yl]-carbamic acid tert-butyl ester. (40). To a solution of (39) (140 mg, 0.325 mmole) in 2 ml dry THF were added triethyl amine (50 mg, 0.48 mmole), DMAP (4 mg, 0.01 eq.) and diethylchlorophosphate (58 mg, 0.325 mmole) The resulting suspension was stirred at room temperature, overnight. Mixture was concentrated down, diluted with 5 ml water, then 5% HCl solution was added to pH=6 and extracted with ethyl acetate 3×5 ml. Combined organic layers were washed with brine, dried over sodium sulfate, filtered and concentrated. The crude was purified using preparative TLC and 10% acetone/methylene chloride to afford 110 mg product, (40). $^1$H-NMR-(400 MHz, CDCl$_3$)

[6-(4-tert-Butoxycarbonylamino-benzyl)-5-methoxy-4-(3-nitro-phenyl)-benzothiazol-2-yl]-carbamic acid tert-butyl ester. (41). A suspension of (40) (110 mg, 0.194 mmole), potassium phosphate (46 mg, 0.194 mmole), boronic acid (51 mg, 0.213 mmole) in 1.5 ml dry toluene was degassed for 10 min using argon, then palladium acetate (4.5 mg, 0.1 eq.) and triphenyl phosphine (20 mg, 0.2 eq.) were added and the mixture was heated at 90° C. for 7 hours. The reaction mixture was cooled to room temperature, diluted with 2 ml water and extracted with ethylacetate (3×5 ml). Combined organic layers were washed with water, brine, dried over sodium sulfate, filtered and concentrated. The residue was purified by prep TLC using 4% MeOH/methylene chloride to obtain 55 mg product (41). $^1$H-NMR-(400 MHz, CDCl$_3$)

2-Amino-6-(4-amino-benzyl)-4-(3-nitro-phenyl)-benzothiazol-5-ol. BA-015. To a solution of (41) (50 mg, 0.082 mmole) in 1 ml dry methylene chloride was added at 0° C. BBr3, 1 M solution in methylene chloride (0.2 ml, 2 eq.). The reaction mixture was let it stirred at RT for 24 hrs. Mixture was concentrated, diluted with 5 ml MeOH, concentrated, then 2 ml of water was added to the residue, neutralized with 30% ammonium hydroxide, extracted with ethylacetate (3×5 ml). Combined organic layers were washed with water, dried over sodium sulfate, concentrated to give 40 mg crude. Purification by preparative TLC gave 13 mg of the desired product, BA-15. $^1$H-NMR-(400 MHz, CDCl$_3$). LCMS (APCI+): 393 (M+1), 85%.

BA-16

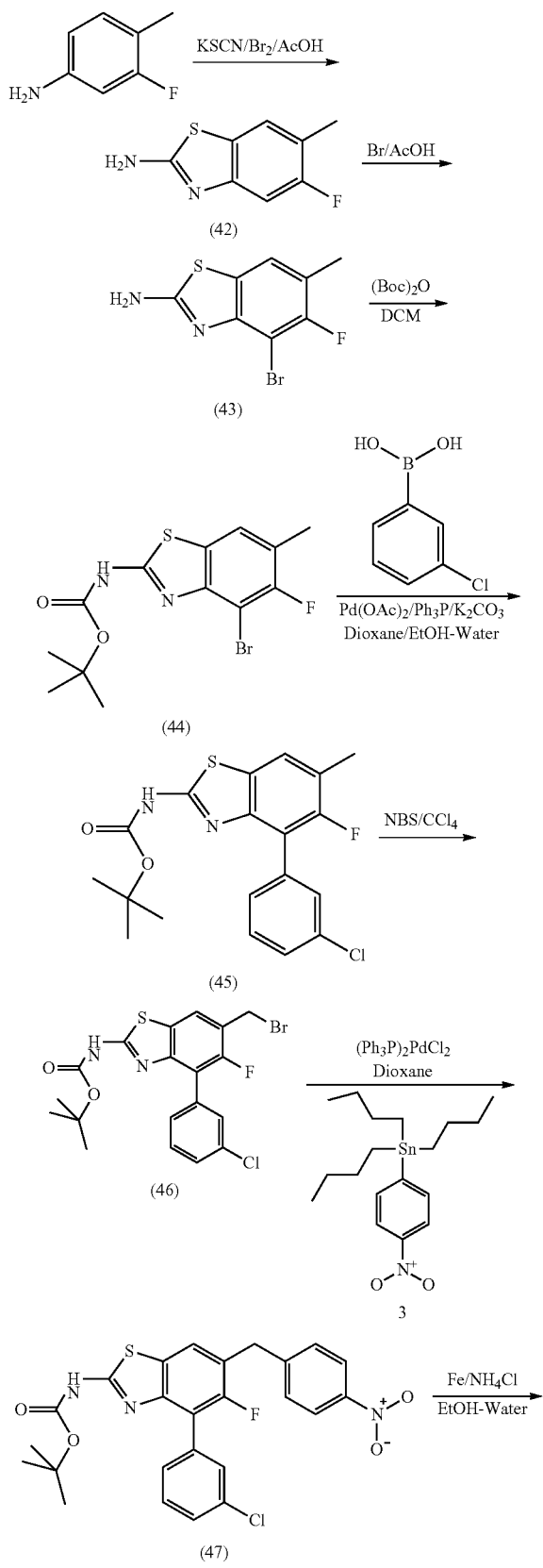

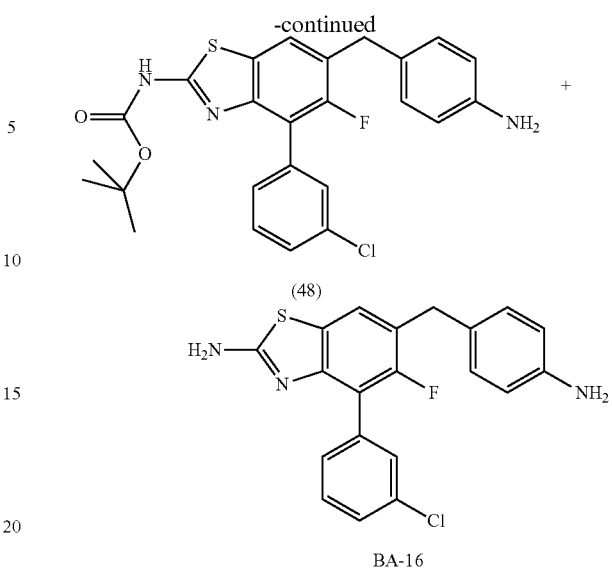

5-fluoro-6-methyl-benzothiazol-2-ylamine. (42). To a stirred solution of 3-fluoro-4-methyl-phenylamine (10.0 g, 79.9 mmol) and potassium thiocyanide (31.06 g, 319.62 mmol) in acetic acid (130 mL) was added a solution of bromine (12.77 g, 79.9 mmol) in acetic acid (20 mL) over 20 min. The reaction mixture was stirred at room temperature for 20 h, poured on to crushed ice-water (800 mL). Ammonium hydroxide solution (28%) was added to pH 8, stirred for 2 h. Filtered, washed with water, dried to afford (42) 14.27 g (98%) as light yellow solid.

4-bromo-5-fluoro-6-methyl-benzothiazol-2-ylamine. (43). To a heated (80° C.) and stirred solution of (42) (10.0 g, 54.88 mmol) in acetic acid (210 mL) was added a solution of bromine (17.54 g, 109.76 mmol) in acetic acid (40 mL) over 30 min. The reaction mixture was stirred at 80° C. for 20 h, cooled to room temperature than poured on to crushed ice-water (400 mL). Ammonium hydroxide solution (28%) was added to pH 8, stirred for 2 h. Filtered, washed with water, dried to afford (43) 12.08 g (84%) as light orange-brown solid.

(4-bromo-5-fluoro-6-methyl-benzothiazol-2-yl)-carbamic acid tert-butyl ester. (44) To a stirred solution of (43) (3.0 g, 11.49 mmol) and di-tert-butyl dicarbonate (2.5 g, 11.49 mmol) in dichloromethane (350 mL) was added DMAP (0.2 g, 1.64 mmol). The reaction was stirred at room temperature for 20 h, than concentrated. The residue was purified by silica gel column chromatography using 1:1 dichloromethane in hexanes to afford (44) 3.45 g (73%) as off-white solid.

[4-(3-chloro-phenyl)-5-fluoro-6-methyl-benzothiazol-2-yl]-carbamic acid tert-butyl ester. (45) To a mixture of (44) (3.3 g, 9.14 mmol), 3-chlorophenylboronic acid (2) (2.14 g, 13.7 mmol), PPh$_3$ (1.17 g, 4.48 mmol), K$_2$CO$_3$ (0.49 g, 3.56 mmol) and Pd(OAc)$_2$ (0.25 g, 1.1 mmol) was added dioxane (90 mL), and EtOH—H$_2$O (1:1, 45 mL). Ar gas was bubbled through the stirred reaction for 15 min. The reaction was stirred at 80° C. under Ar for 20 h. The reaction was cooled to room temperature, concentrated and H$_2$O (60 mL) and dichloromethane (80 mL) were added. The layers were separated and the aqueous was extracted with dichloromethane (2×40 mL). The combined organic extracts were dried with Na$_2$SO$_4$, filtered, and concentrated. The residue was purified by silica gel column chromatography using 1:1 dichloromethane-hexanes to afford (45) 2.8 g (78%) as off-white solid.

[6-bromomethyl-4-(3-chloro-phenyl)-5-fluoro-benzothiazol-2-yl]-carbamic acid tert-butyl ester. (46) To a mixture of (45) (1.0 g, 2.54 mmol) and NBS (0.5 g, 2.8 mmol) in CCl₄ (50 mL) was added benzoylperoxide (0.1 g, 0.41 mmol). The reaction was stirred at 80° C. under N₂ for 18 h. The reaction was cooled to room temperature and concentrated. The residue was dissolved in mixture of dichloromethane and hexanes (1:1, 8 mL) and purified by silica gel column chromatography using 1:1 dichloromethane hexanes to afford (46) 0.63 g (53%) as a light brown solid.

[4-(3-chloro-phenyl)-5-fluoro-6-(4-nitro-benzyl)-benzothiazol-2-yl]-carbamic acid tert-butyl ester. (47) To a mixture of (46) (0.3 g, 0.64 mmol) and tributyl-(4-nitro-phenyl)-stannane (3) (0.39 g, 0.95 mmol) in dioxane (10 mL) was added bis-triphenylphosphine palladium dichloride (0.02 g, 0.03 mmol). Ar gas was bubbled through the stirred reaction for 2 min. The reaction was stirred at 80° C. under Ar for 10 h. The reaction was cooled to room temperature, concentrated. The residue was purified by silica gel column chromatography using 1:1 dichloromethane-hexanes to afford (47) 0.21 g (64%) as light yellow solid.

6-(4-amino-benzyl)-4-(3-chloro-phenyl)-5-fluoro-benzothiazol-2-ylamine hydrochloride.

BA-16. To a mixture of (47) (0.19 g, 0.36 mmol), Fe (0.08 g, 1.44 mmol) and ammonium chloride (0.12 g, 2.16 mmol) in ethanol (10 mL) was added water (3.3 mL). The reaction was stirred at 80° C. for 16 h. The reaction mixture was cooled to room temperature, filtered over Celite, concentrated. The residue was purified by prep TLC using 40% ethyl acetate in hexanes afforded 0.48 g (28%) of (48) as off-white solid (less polar compound Rf 0.45) and 0.085 g (62%) of BA-16 as off-white solid (polar compound Rf 0.21). 1H NMR-(400 MHz, CDCl₃); Yes MS (APCI+): 384.0 (M+1), LC-MS: >99%. To BA-16 (0.02 g, 0.05 mmol) in ether (1.0 mL) was added 2M HCl in ether (0.5 mL). The reaction mixture was stirred for 1 h. The ether layer was decanted, triturated with ether (2×2 mL), dried to afford 0.017 g (78%) BA-16, HCl salt, as light yellow solid. ¹H NMR-(400 MHz, CDCl₃); Yes, MS (APCI+): 384.0 (M+1), LC-MS: 79%.

BA-18,

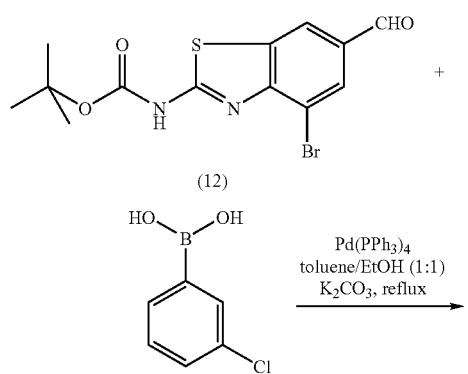

-continued

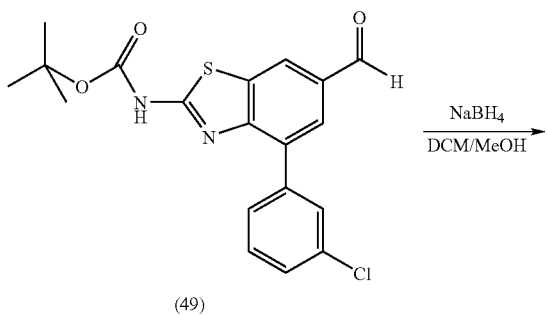

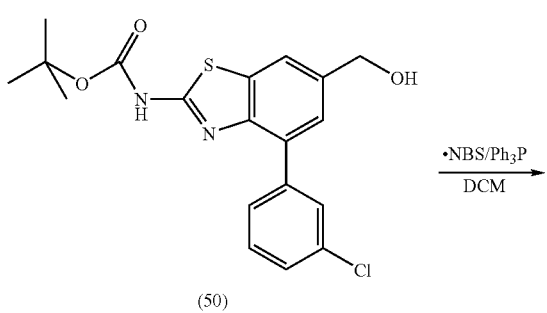

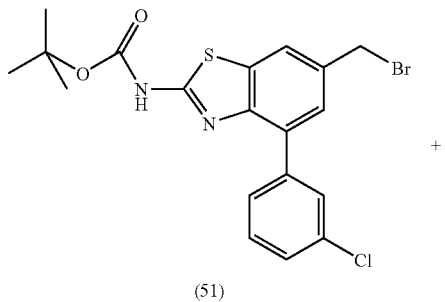

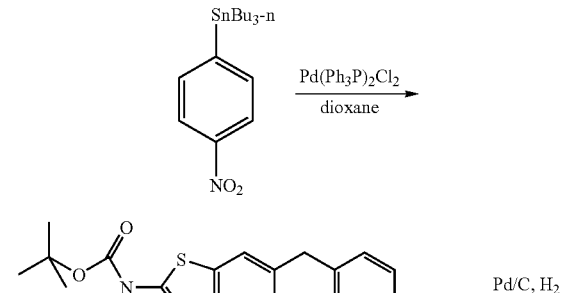

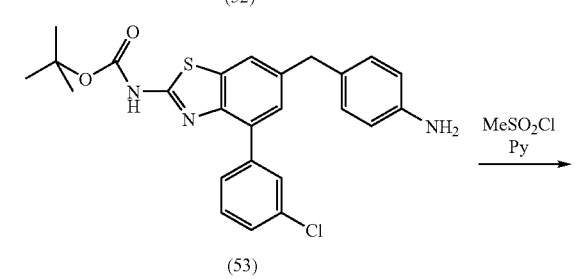

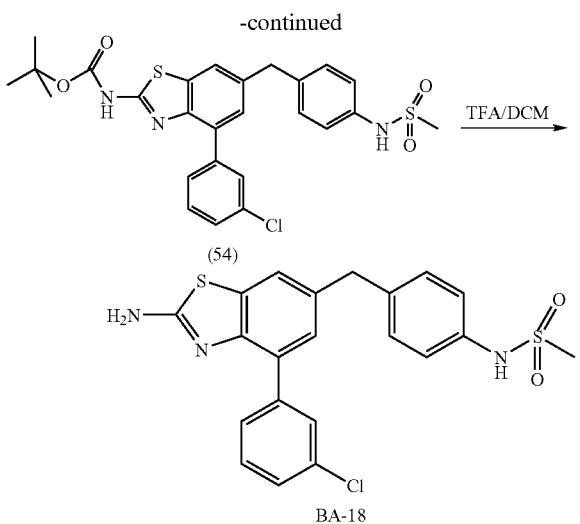

[4-(3-Chloro-phenyl)-6-formyl-benzothiazol-2-yl]-carbamic acid tert-butyl ester. (49). To a mixture of boronic acid (800 mg, 5 mmol, 1.1 eq.), palladium catalyst (500 mg, 0.43 mmol, 0.1 eq.), $K_2CO_3$ (4.7 g, 35 mmol, 8 eq.) and (12) (1.54 g, 4.3 mmol, 1 eq.) was added toluene (30 ml) and EtOH (30 ml). The mixture was stirred at 95 C under Ar overnight. After cooling to room temperature, water was added. The mixture was extracted with EtOAc (25 ml×3). The organic layers were dried over $MgSO_4$. Removal of solvent under reduced pressure gave a residue, which was purified by chromatography on silica gel using hexane/DCM (from 1.5:1 to 1:2) as eluent to afford (49) 960 mg in 57% yield. $^1$H-NMR (400 MHz, $CDCl_3$)

[4-(3-Chloro-phenyl)-6-hydroxymethyl-benzothiazol-2-yl]-carbamic acid tert-butyl ester. (50). To a solution of compound (49) (540 mg, 1.38 mmol) in dichloromethane (8 mL) and MeOH (6 ml) was added sodium borohydride (80 mg, 2.1 mmol, 1.5 eq.) in one portion at 0 C. The mixture was stirred at 0 C~rt for 1 hr. Then water was added followed by 1N HCl aq. to bring the mixture to pH=3. Solid was filtered and washed with water. After dried in the air, 475 mg of product (50) was obtained in 88% yield. 1H-NMR (400 MHz).

[6-Bromomethyl-4-(3-chloro-phenyl)-benzothiazol-2-yl]-carbamic acid tert-butyl ester. (51) To a suspension of alcohol (50) (360 mg, 0.92 mmol, 1 eq.) in DCM (12 mL) was added $Ph_3P$ (340 mg, 1.3 mmol, 1.4 eq.). The mixture was stirred at rt for 5 min. and then cooled to 0 C. NBS (230 mg, 1.3 mmol, 1.4 eq.) was added in one portion. The resulting mixture was stirred at rt for 1 hr. The volatile material was removed under reduced pressure and the residue was purified by chromatography on silica gel using DCM/hexane (1:2) as eluent to give product (51) 305 mg in 73% yield.

[4-(3-Chloro-phenyl)-6-(4-nitro-benzyl)-benzothiazol-2-yl]-carbamic acid tert-butyl ester. (52). To a mixture of compound (51) (200 mg, 0.44 mmol), tributyl-(4-nitro-phenyl)-stannane (363 mg, 0.88 mmol, 2 eq.), and palladium catalyst (Pd(Ph3P)$_2$C12, 70 mg, 0.1 mmol, 0.2 eq.) was added dioxane (8 ml). The resulting mixture was refluxed under Ar for 4 hrs. After cooling to rt, the volatile material was removed under reduced pressure to afford a residue, which was purified by chromatography on silica gel using DCM/hexane (1:1.5) as eluent to give 82 mg of compound (52) in 38% yield.

[6-(4-Amino-benzyl)-4-(3-chloro-phenyl)-benzothiazol-2-yl]-carbamic acid tert-butyl ester. (53). A mixture of compound (52) (82 mg, 0.165 mmol), Pd/C (105 mg) in EtOAc (5 ml) was stirred under one atmosphere of $H_2$ for 1 hr. The reaction mixture was passed through a plug of celite, washed with EtOAc. The organics was evaporated under reduced pressure to give 76 mg of compound (53) in quantitative yield.

[4-(3-Chloro-phenyl)-6-(4-methanesulfonylamino-benzyl)-benzothiazol-2-yl]-carbamic acid tert-butyl ester. (54). To a solution of compound (53) (76 mg, 0.163 mmol, 1 eq.) in pyridine (1 ml) was added $MeSO_2Cl$ (0.014 ml, 0.17 mmol, 1.05 eq.) by a syringe at 0 C. The resulting mixture was stirred at 0 C~rt for 1 hr. Then the mixture was poured into water and extracted with EtOAc. The EtOAc layer was washed with 1N HCl aq. and dried over $MgSO_4$. Removal of solvent gave a residue, which was purified by chromatography on silica gel using DCM/hexane (1:1) as eluent to afford 83 mg of (54) in 94% yield.

N-{4-[2-Amino-4-(3-chloro-phenyl)-benzothiazol-6-ylmethyl]-phenyl}-methanesulfonamide. BA-18. To a solution of (54) (84 mg, 0.153 mmol) in DCM (1 ml) was added TFA (1 ml). After the mixture was stirred at rt for 1 hr, the volatile material was removed under reduced pressure to give a residue, which was purified by chromatography on silica gel using EtOAc/hexane with a ratio of 1:1.5 follow by 1:1 as eluent to give 62 mg of desired product, which was further triturated with a mixture of DCM (1 ml) and hexane (7 ml) to give 59 mg of product BA-18 in 87% yield. LCMS: 100%. 1H NMR.

BA-19.

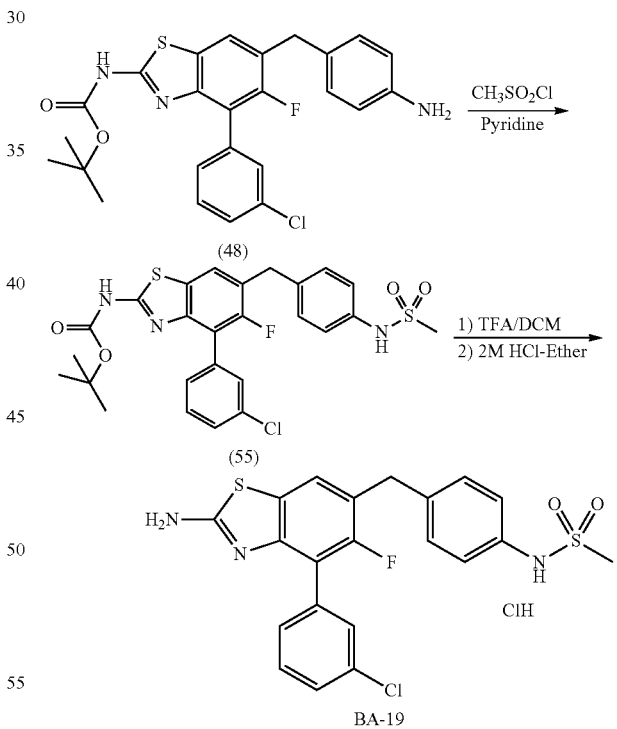

N-{4-[2-amino-4-(3-chloro-phenyl)-5-fluoro-benzothiazol-6-ylmethyl]-phenyl}-methanesulfonamide hydrochloride. BA-19. To (48) (0.044 g, 0.09 mmol) in pyridine (1.5 mL) was added methanesulfonyl chloride (0.31 g, 0.27 mmol). The reaction mixture was stirred for 1 h, concentrated. Water (20 mL) and ether (20 mL) were added. The organic layer was separated and the aqueous was extracted with ether (2×20 mL). The combined organic extracts were dried with Na2SO4, filtered, and concentrated to afford 0.05 g (98%) of (55) as off-white solid To a solution of (55) (0.05 g, 0.09 mmol) in dichloromethane (1 mL) was added trifluoroacetic acid (1 mL). The reaction mixture was stirred for 1.5 h, concentrated. Water (2 mL) and sat. Na₂HCO₃ (3 mL) were added, extracted with ether (2×20 mL). The combined organic extracts were dried with Na₂SO₄, filtered, and concentrated. The residue was suspended in ether (1 mL) and dioxane (1 mL), 2M HCl in ether (0.5 mL) was added. The reaction mixture was stirred for 1 h. The ether layer was decanted, triturated with ether (2×2 mL), dried to afford 0.03 g (70%) of BA-19 as off-white solid. ¹H NMR-(400 MHz, CDCl₃); MS (APCI+): (M+1) LC-MS: >98%.

BA-20

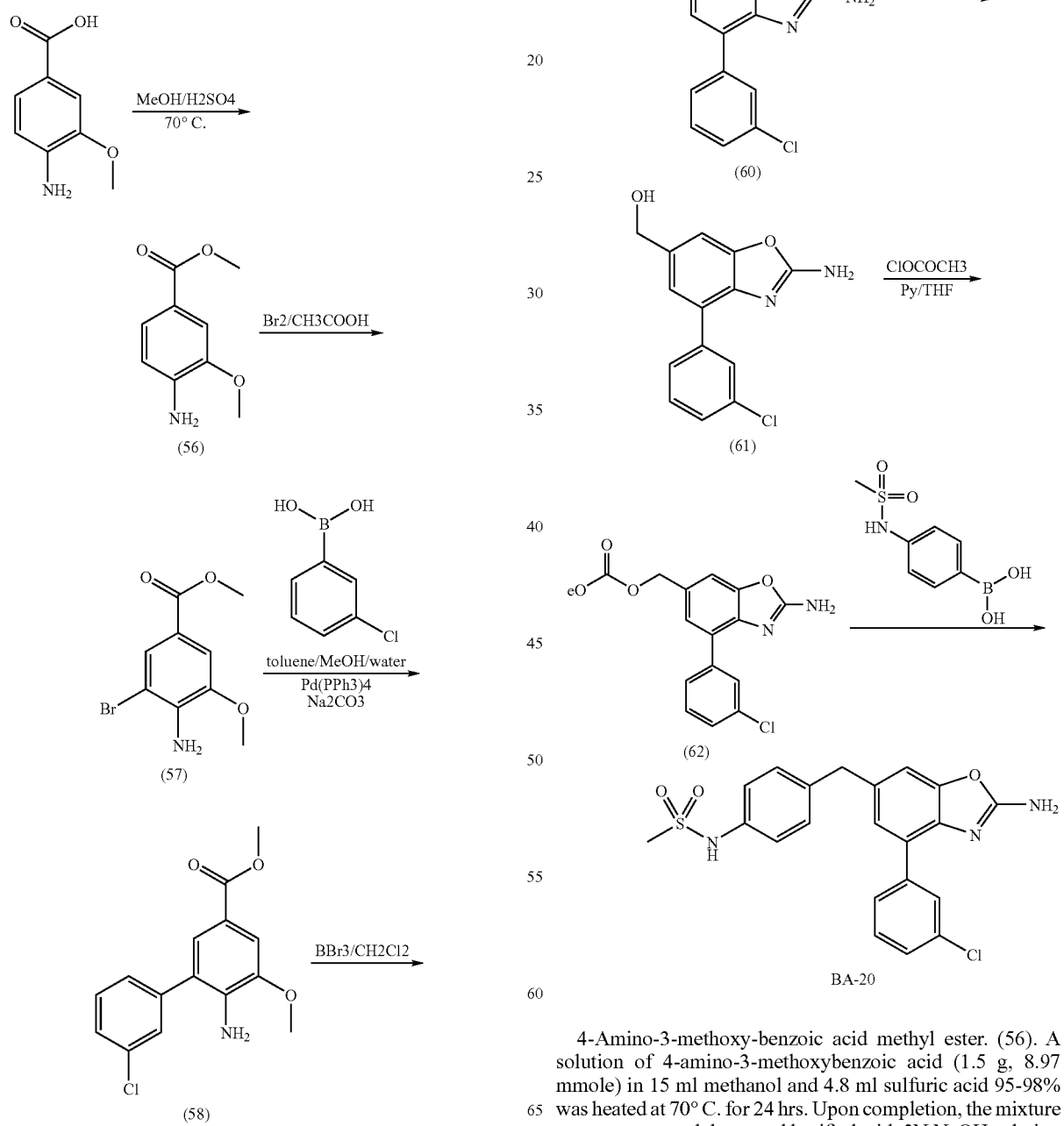

4-Amino-3-methoxy-benzoic acid methyl ester. (56). A solution of 4-amino-3-methoxybenzoic acid (1.5 g, 8.97 mmole) in 15 ml methanol and 4.8 ml sulfuric acid 95-98% was heated at 70° C. for 24 hrs. Upon completion, the mixture was concentrated down and basified with 2N NaOH solution to pH=8. A solid precipitated out. The suspension was filtered off, solid was washed with water, dried to afford 1.62 g tan solid (56), 100% yield. $^1$H-NMR (400 MHz, DMSO)

4-Amino-3-bromo-5-methoxy-benzoic acid methyl ester. (57) To a solution of (56) (1.6 g, 8.83 mmole) in 15 ml methanol was added slowly at room temperature a solution of bromine (0.45 ml, 8.83 mmole) in 4 mL acetic acid. The reaction mixture was stirred at room temperature for 7 hrs. The reaction mixture was concentrated down to a solid residue. The residue was taken in 50 mL saturated solution of NaHCO3 and extracted 3×100 mL ethyl acetate. Combined organic layers were washed with water, brine, dried over Na2SO4, filtered and concentrated to give 2.1 g brown solid (57), 95.1% yield. $^1$H-NMR (400 MHz, DMSO)

6-Amino-3'-chloro-5-methoxy-biphenyl-3-carboxylic acid methyl ester. (58). A suspension of (57) (2.14 g, 8.26 mmole), 3-chlorophenylboronic acid (1.95 g, 12.39 mmole), sodium carbonate (2.63 g, 24.78 mmole) in a mixture of solvents: 70 mL toluene, 12 mL ethanol and 30 mL water was degassed for 10 min before the catalyst addition. After the catalyst Pd(PPh$_3$)$_4$ (960 mg, 0.826 mmole) was added, the reaction mixture was refluxed for 7 hrs. The reaction mixture was concentrated down, diluted with water and extracted with ethylacetate. Combined organic layers were washed with water, brine, dried over Na2SO4, filtered and concentrated to give 3.8 g crude. Purification by column chromatography using a mixture of methylene chloride/hexane=1:1 gave 2.12 g product (58), 88.3% yield. $^1$H-NMR (400 MHz, DMSO)

6-Amino-3'-chloro-5-hydroxy-biphenyl-3-carboxylic acid methyl ester. (59). To a solution of (58) (2.12 g, 7.27 mmole) in 75 mL anhydrous methylene chloride was added at −70° C. neat BBr3 (2.22 mL, 21.81 mmole). The reaction mixture was slowly warmed up to room temperature and stirred for 5 hrs. Mixture was cooled to 0° C. and diluted by slowly addition of 100 mL of methanol. The mixture was stirred at room temperature, overnight, then concentrated down, diluted with 50 ml water and neutralized to pH=6 by addition of 30% ammonium hydroxide. The mixture was extracted with ethylacetate. Combined organic layers were washed with water, brine, dried over Na$_2$SO$_4$, filtered and concentrated to give 2.1 g crude product (59), quantitative yield, pure enough to use it next. $^1$H-NMR (400 MHz, DMSO)

2-Amino-4-(3-chloro-phenyl)-benzooxazole-6-carboxylic acid methyl ester. (60). To a solution of cyanogen bromide (920 mg, 8.7 mmole) in a mixture of methanol/water=7:3 (12 mL) was added a solution of (59) (2.1 g, 7.56 mmole) in 12 mL methanol. The reaction mixture was stirred at room temperature for 24 hrs. More cyanogen bromide (100 mg) was added and mixture stirred for one more day. The mixture was concentrated down, diluted with 15 mL 2N NaOH solution, stirred for 20 minutes, and filtered off. The solid was washed with water, trituration with 5% MeOH/ether gave 1.45 g light pink solid (60), 57% yield. $^1$H-NMR (400 MHz, DMSO)

[2-Amino-4-(3-chloro-phenyl)-benzooxazol-6-yl]-methanol. (61). To a solution of (60) (260 mg, 0.86 mmole) in 10 mL anhydrous THF at 0° C. was added LiBH$_4$ (2M in THF, 1.75 ml, 4 eq.). The reaction mixture was stirred at room temperature for 3 days. The reaction was quenched with 5 ml saturated solution of NH$_4$Cl, diluted with 5 mL water and extracted with 2×20 mL ethylacetate. Combined organic layers were washed with water, brine, dried over Na$_2$SO$_4$, filtered and concentrated to give 200 mg crude. Trituration with ether/hexane=1:1 gave 140 mg off white solid (61), 59% yield. $^1$H-NMR (400 MHz, DMSO)

Carbonic acid 2-amino-4-(3-chloro-phenyl)-benzooxazol-6-ylmethyl ester methyl ester. (62) To a solution of (61) (140 mg, 0.51 mmole), pyridine (0.103 ml, 2.5 eq.) in 2 mL anhydrous THF at 0° C. was added methylchloroformate (102 mg, 1.071 mmole). The reaction mixture was stirred at room temperature for 24 hrs. The reaction was diluted with 1.5 mL water and extracted 3× with methylene chloride. Combined organic layers were washed with water, brine, dried over Na$_2$SO$_4$, filtered and concentrated to give 196 mg crude (62). This was pure enough for next step. $^1$H-NMR (400 MHz, DMSO)

N-{4-[2-Amino-4-(3-chloro-phenyl)-benzooxazol-6-yl-methyl]-phenyl}-methanesulfonamide. BA-20. To a solution of (62) (190 mg, 0.48 mmole), 3-chlorophenyl boronic acid (157 mg, 0.73 mmole), K$_2$CO$_3$ (153 mg, 1.1 mmole), [Pd(n$^3$-C$_3$H$_5$)Cl]$_2$ (9 mg, 0.024 mmole), 1,5-bis(diphenylphosphino) pentane (22 mg, 0.048 mmole) in 1.5 mL anhydrous DMF was heated at 80° C. for 24 hrs. The reaction was diluted with 5 mL water and extracted 3× with ethyl acetate. Combined organic layers were washed with water, brine, dried over Na$_2$SO$_4$, filtered and concentrated to give 200 mg crude. Purification by silicagel prep plate gave 10 mg white solid BA-20. $^1$H-NMR (400 MHz, DMSO)

BA-21

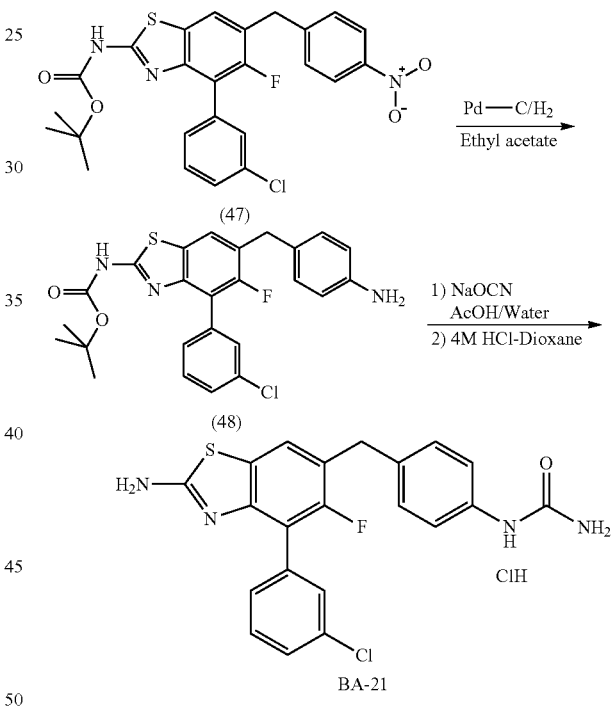

[6-(4-amino-benzyl)-4-(3-chloro-phenyl)-5-fluoro-benzothiazol-2-yl]-carbamic acid tert-butyl ester. (47). To (47) (0.11 g, 0.21 mmol) in ethyl acetate (3.0 mL) was added Pd—C (0.16 g, 10%, 50% wet). The reaction mixture was stirred under H$_2$ atmosphere for 5 h, filtered over Celite, concentrated to afford 0.09 g (95%) of (48) as light brown solid.

{4-[2-amino-4-(3-chloro-phenyl)-5-fluoro-benzothiazol-6-ylmethyl]-phenyl}-urea hydrochloride. BA-21. To (48) (0.1 g, 0.19 mmol) in acetic acid-water (1:2, 1 mL) was added sodium cyanate (0.05 g, 0.77 mmol). The reaction mixture was stirred for 72 h at room temperature. Water (4 mL) was added, basified with 28% NH$_4$OH solution to pH8, extracted with ethyl acetate (3×6 mL). The combined organic extracts were dried with Na$_2$SO$_4$, filtered, and concentrated. The residue was triturated with 1:1 dichloromethane-hexanes (2×2 mL), than treated with 4M hydrochloric acid in dioxane at 80° C. for 40 min. The reaction was concentrated, triturated with ether (2×2 mL), dried to afford BA-21 0.03 g (33%) as light grayish-brown solid. ¹H NMR-(400 MHz, CDCl₃). MS (APCI+): 427.0 (M+1), LC-MS:84%.

BA-22, and
BA-24

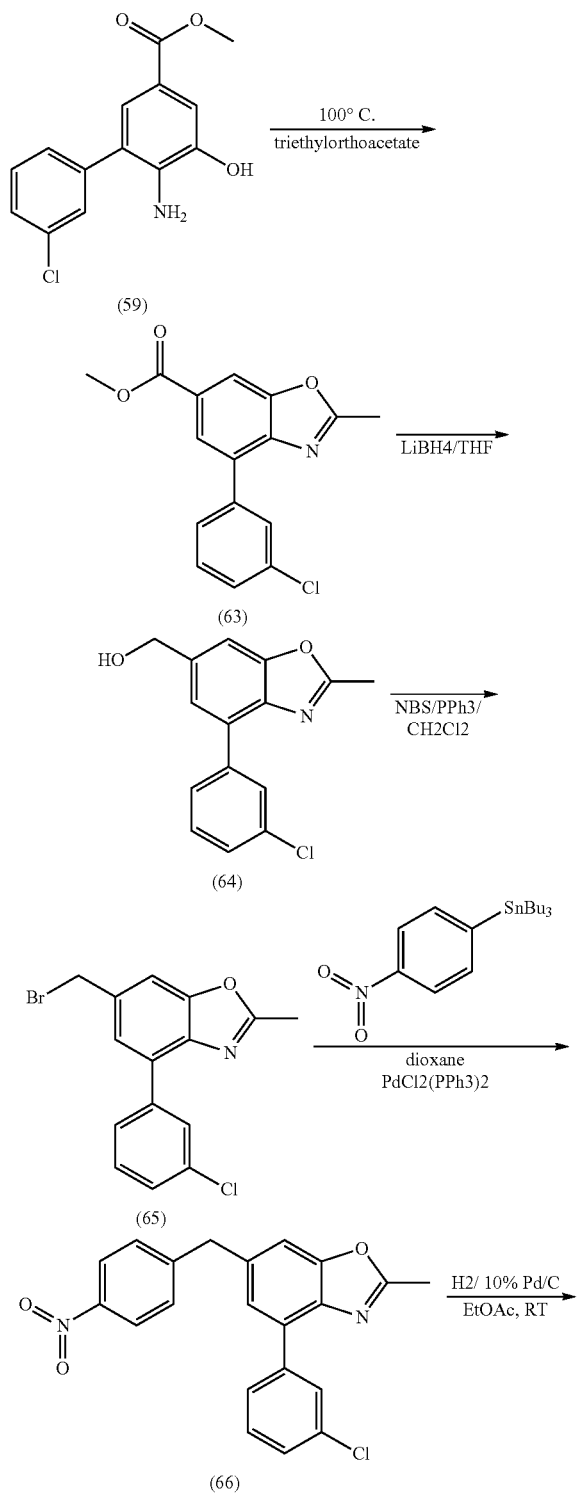

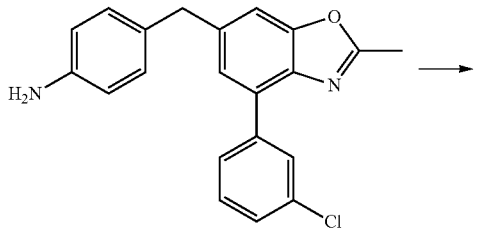

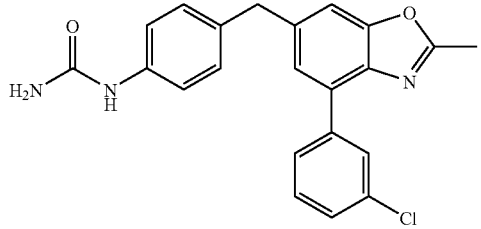

methyl 4-(3-chlorophenyl)-2-methyl-1,3-benzoxazole-6-carboxylate. (63). A solution of (59) (150 mg, 0.54 mmole) in 1 mL triethylorthoformate was heated at 100° C. for 4 hours. The reaction mixture was cooled to room temperature, diluted with water and extracted with ethylacetate. Combined organic layers were washed with brine, dried over Na₂SO₄, concentrated to give 160 mg crude. After trituration with 50% ether in hexane 130 mg (63) was obtained. ¹H-NMR (400 MHz, DMSO)

[4-(3-chlorophenyl)-2-methyl-1,3-benzoxazol-6-yl] methanol. (64). To a solution of (63) (125 mg, 0.414 mmole) in 5 mL anhydrous THF at 0° C. was added LiBH₄ (2M in THF, 0.62 ml, 3 eq.). The reaction mixture was stirred at room temperature for 3 days. The reaction was quenched with 5N HCl, diluted with water and extracted with 3×10 mL ethylacetate. Combined organic layers were washed with water, brine, dried over Na₂SO₄, filtered and concentrated to give 130 mg crude. Purification by silicagel prep TLC afforded 98 mg (64). ¹H-NMR (400 MHz, DMSO)

6-(bromomethyl)-4-(3-chlorophenyl)-2-methyl-1,3-benzoxazole. (65). To a solution of (64) (90 mg, 0.33 mmole), triphenylphosphine (87 mg, 0.33 mmole) was added at 0° C. NBS (59 mg, 0.33 mmole). The reaction mixture was stirred at room temperature, overnight. The mixture was concentrated and purified by column chromatography using 50% methylene chloride in hexane to give 55 mg (65). ¹H-NMR (400 MHz, DMSO)

4-(3-chlorophenyl)-2-methyl-6-(4-nitrobenzyl)-1,3-benzoxazole. (66). To a solution of (65) (50 mg, 0.148 mmole), 3-nitrophenyl tributyl stannane (91 mg, 0.22 mmole), bis (triphenyl phosphine)dichloride (11 mg, 10%) in 2 mL anhydrous dioxane was heated at 90° C. for 24 hrs. The reaction was cooled to RT, diluted with 2 mL methylene chloride and purified by silicagel prep plate and gave 40 mg (66) yellow solid. ¹H-NMR (400 MHz, DMSO)

4-{[4-(3-chlorophenyl)-2-methyl-1,3-benzoxazol-6-yl] methyl}aniline. BA-22. A suspension of (66) (40 mg, 0.102 mmole), 10% Pd/C (12 mg, 10%) in 3 mL ethylacetate was stirred under H₂ (1 atm) for 5 hours. Mixture was diluted with ethylacetate and filtered off. After solvent evaporation 40 mg crude was obtained. Purification by silicagel prep TLC afforded 30 mg product BA-22.
¹H-NMR (400 MHz, DMSO). HPLC 97%

N-(4-{[4-(3-chlorophenyl)-2-methyl-1,3-benzoxazol-6-yl]methyl}phenyl)urea. BA-24. A suspension of BA-22 (20 mg, 0.057 mmole), sodium cyanate (15 mg, 0.23 mmole) in a mixture of acetic acid/water=1:2 (2 mL) was stirred at room temperature for 3 days. Mixture was concentrated down, diluted with water and extracted several times with ethylacetate. Combined organic layers were washed with brine, dried over Na₂SO₄, filtered and concentrated. Crude was purified by silicagel prep TLC to afford 11 mg BA-24. ¹H-NMR (400 MHz, DMSO). 2.63 (s, 3H), 4.028 (s, 2H), 5.78 (s, 2H), 7.155 (d, J=8.8 Hz, 2H), 7.29 (d, J=8.8 Hz, 2H), 7.44-7.47 (m, 1H), 7.51-7.55 (m, 3H), 7.93 (d, J=8 Hz, 1H), 8.08 (dd, J=4 Hz, 2 Hz, 8.41 (s, 1H).

BA-23

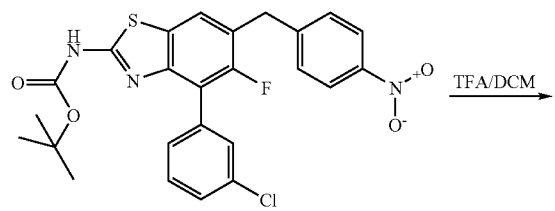

4-(3-chloro-phenyl)-5-fluoro-6-(4-nitro-benzyl)-benzothiazol-2-ylamine. (67). To a solution of (47) (0.05 g, 0.09 mmol) in dichloromethane (1 mL) was added trifluoroacetic acid (1 mL). The reaction mixture was stirred for 1.5 h, concentrated. Water (2 mL) was added, basified with 28% NH₄OH solution to pH8, extracted with dichloromethane (2×3 mL). The combined organic extracts were dried with Na₂SO₄, filtered, and concentrated to afford 0.035 g (97%) of (67) as yellow solid.

4-(3-chloro-phenyl)-5-fluoro-6-(4-nitro-benzyl)-benzothiazole. (68). To a cooled (−8° C.) solution of (67) (0.035 g, 0.08 mmol) in phosphoric acid (0.8 mL, 85% wt solution) was added a solution of sodium nitrite (0.035 g, 0.51 mmol) in water (0.1 mL) over 5 min. The reaction mixture was stirred for 5 min at −4° C., than hypophosphorous acid (0.6 mL) was added, warmed to room temperature. Water (5 mL) was added, basified with Na₂CO₃ solution to pH8, extracted with dichloromethane (2×20 mL). The combined organic extracts were dried with Na₂SO₄, filtered, and concentrated. The residue was purified by prep TLC using dichloromethane to afford 0.018 g (53%) of (68) as light yellowish-brown solid.

4-[4-(3-chloro-phenyl)-5-fluoro-benzothiazol-6-ylmethyl]-phenylamine hydrochloride. BA-23. To (68) (0.018 g, 0.045 mmol) in ethyl acetate (2.5 mL) was added Pd—C (0.08 g, 10%, 50% wet). The reaction mixture was stirred under H₂ atmosphere for 5 h, filtered over Celite, concentrated. The residue was dissolved in ether (0.5 mL), than 2M HCl in ether (0.5 mL) was added. The reaction mixture was stirred for 1 h. The ether layer was decanted, triturated with ether (2×1 mL), dried to afford 0.007 g (38%) of BA-23 as off-white solid. ¹H NMR-(400 MHz, CDCl₃); MS (APCI+): 369.0 (M+1), LC-MS: 92%.

BA-26

BA-27

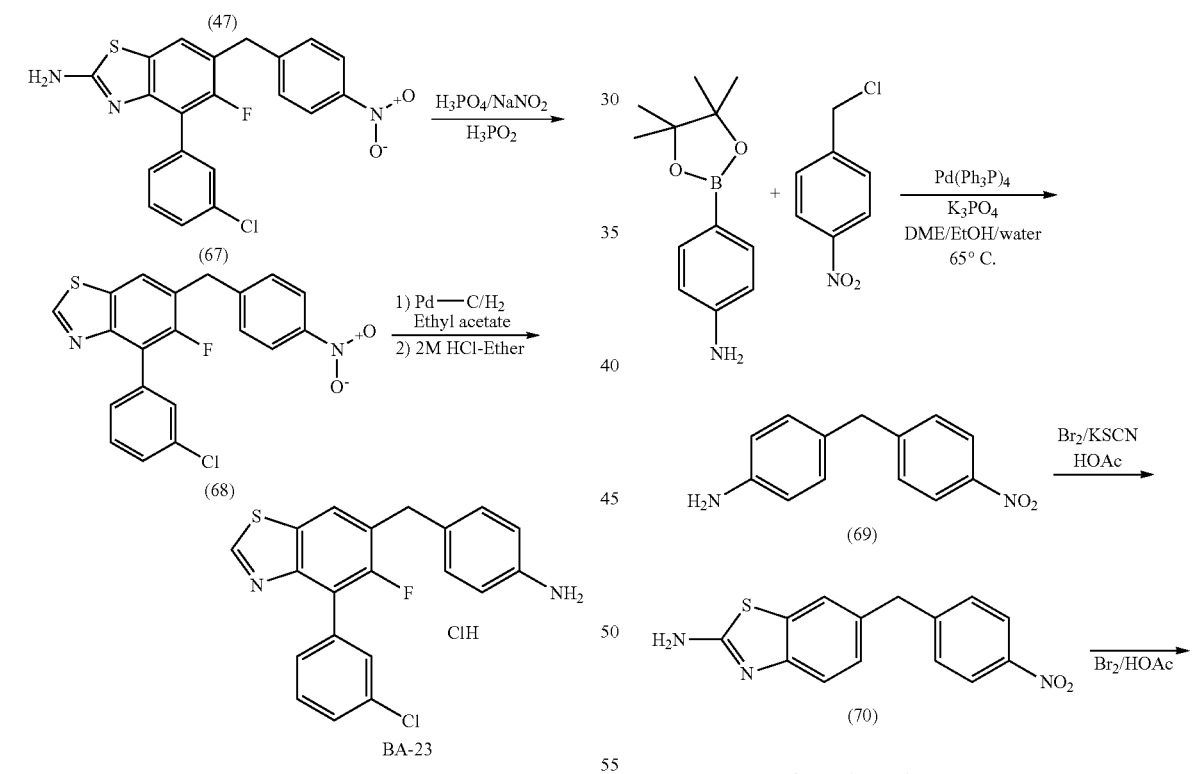

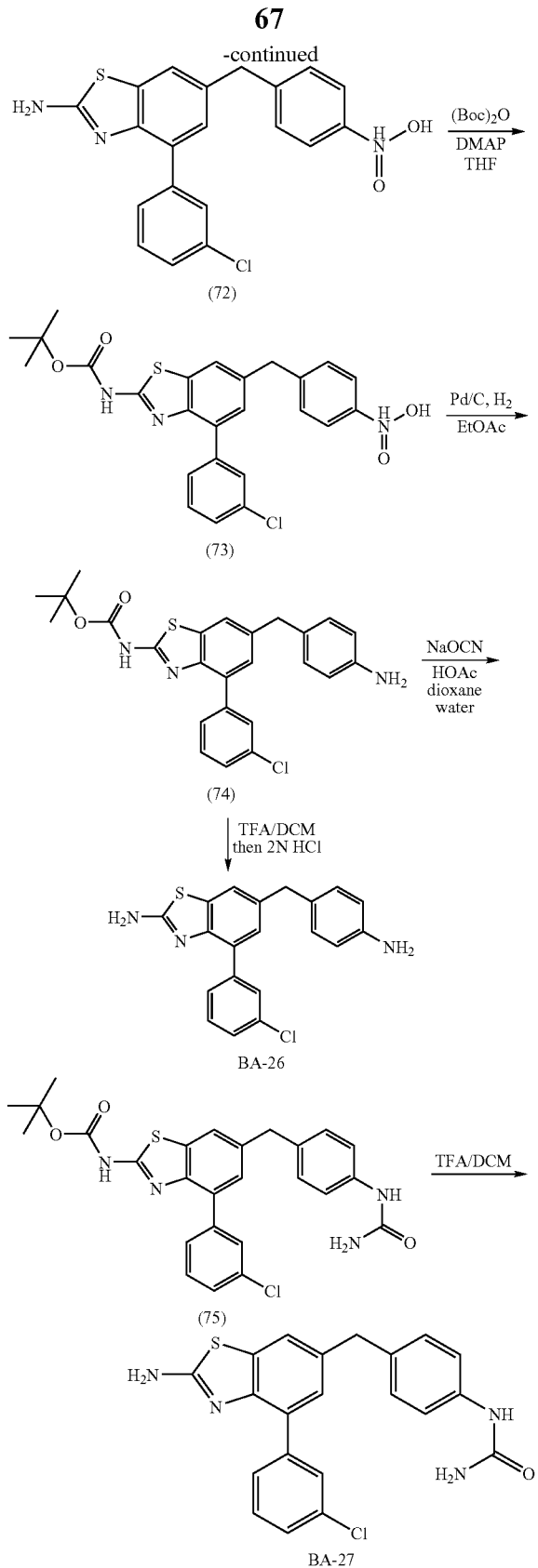

22.8 mmol, 1.14 eq.), Pd(PPh$_3$)$_4$ (2.31 g, 2.2 mmol, 0.1 eq.) K$_3$PO$_4$ (8.5 g, 45 mmol, 2 eq.) in DME (100 mL), EtOH (30 ml) and water (30 ml) was stirred at 65 C for 3 hours. After cooling to room temperature, the volatile material was removed under reduced pressure to give a residue, which was partitioned between EtOAc and water. Organic layer was separated and dried. Solvent was removed and the crude product was purified by chromatography on silica gel using DCM/hexane (1:1) as eluent to afford the product (69) (1.4 g, 30% yield).

6-(4-Nitro-benzyl)-benzothiazol-2-ylamine. (70). To a reaction mixture of compound (69) (0.7 g, 3.1 mmole), KSCN (600 mg, 6.2 mmol, 2 eq.) in acetic acid (10 ml) was added bromine dropwise by a syringe at 0° C. with stirring. After the addition was complete, the resulting mixture was stirred at room temperature until starting material was consumed (monitored by TLC). The mixture was diluted with water. The solid was collected by filtration and washed with water and dried under N2 flow to give the desired product (70) (526 mg, 60% yield). $^1$H-NMR (400 MHz, CDCl$_3$)

4-Bromo-6-(4-nitro-benzyl)-benzothiazol-2-ylamine. (71). Compound (70) (906 mg, 3 mmol) was suspended in acetic acid (10 mL) and bromine was added dropwise by a syringe at room temperature. After the addition was complete, the reaction mixture was stirred at room temperature over night. The reaction mixture was poured into water and the solid was collected by filtration and dried. 870 mg of (71) was obtained in 79% yield.

4-(3-Chloro-phenyl)-6-(4-nitro-benzyl)-benzothiazol-2-ylamine. (72). A reaction mixture of compound (71) (435 mg, 1.2 mmole), the boronic acid (230 mg, 1.44 mmol, 1.2 eq.), Pd(PPh$_3$)$_4$ (140 mg, 0.71 mmol, 0.1 eq.) in dioxane (4 mL), and 2N Na$_2$CO$_3$ aqueous solution (2.5 mL, 6 eq.) was stirred under reflux overnight under Ar. After cooling to room temperature, the volatile material was removed under reduced pressure to give a residue, which was partitioned between water (15 mL) and ethyl acetate (15 mL). The organic layer was separated. The aqueous layer was extracted with ethyl acetate (10 ml×3). The combined organic layers were dried and evaporation of solvent gave a residue, which was purified by chromatography on silica gel using DCM/hexane (1:1) as eluent to afford the product (72) (488 mg, 73% yield).

[4-(3-Chloro-phenyl)-6-(4-nitro-benzyl)-benzothiazol-2-yl]-carbamic acid tert-butyl ester. (73). Compound (72) (379 mg, 0.95 mmol) was dissolved in THF (5 mL). (Boc)$_2$O (230 mg, 1.1 mmol, 1.1 eq.) was added followed by DMAP (12 mg, 0.1 mmol, 0.1 eq.). The mixture was stirred at room temperature overnight. Then 0.5 additional eq. of (Boc)$_2$O was added. After the resulting mixture was stirred for 4 hours, the volatile material was removed under reduced pressure. The residue was purified by chromatography on silica gel using dichloromethane/hexanes (1:1) as eluent to give 281 mg of (73), which contains bis-Boc product.

[6-(4-Amino-benzyl)-4-(3-chloro-phenyl)-benzothiazol-2-yl]-carbamic acid tert-butyl ester. (74). Compound (73) containing Bis-Boc protected counterpart (211 mg, 0.95 mmol) was dissolved in ethyl acetate (10 mL). Pd/C (300 mg, 10%, wet) was added and the mixture was stirred under H$_2$ (1 atm) for 3 h. The catalyst was filtered and washed with ethyl acetate (10 mL×3). Removal of solvent under reduced pressure gave 200 mg of desired (74) in quantitative yield.

6-(4-Amino-benzyl)-4-(3-chloro-phenyl)-benzothiazol-2-ylamine. BA-26. Compound (74) (30 mg, 0.06 mmol) was dissolved in dichloromethane (1 mL). Trifluoroacetic acid (1 mL) was added. The mixture was stirred at rt for 1 hr. The volatile material was removed and the residue was partitioned between ethyl acetate (EA) and sodium bicarbonate. The EA 4-(4-Nitro-benzyl)-phenylamine. (69). A reaction mixture of 4-nitrobenzyl chloride (2.44 g, 20 mmole, 1 eq.), 4-(4,4,5,5-tetramethyl-[1,3,2]dioxaborolan-2-yl)-phenylamine (5 g, layer was separated and dried over MgSO4. Removal of solvent gave a residue, which was treated with 2N HCl in ether. The precipitate was collected by filtration. 20 mg of desired product BA-26 was obtained as HCl salt, which is a white solid (83% yield). LCMS: 97.8%. $^1$H-NMR (400 MHz, DMSO-$d_6$)

[4-(3-Chloro-phenyl)-6-(4-ureido-benzyl)-benzothiazol-2-yl]-carbamic acid tert-butyl ester (75). A mixture of compound (74) (33 mg, 0.06 mmol), NaOCN (36 mg, 0.13 mmol, 2 eq.) in HOAc (0.2 mL) and water (0.2 mL) was stirred at rt overnight. Then the mixture was diluted with addition of water. Solid was collected by filtration and purified by Prep TLC plate using DCM/MeOH (30:1) as developing system to give 18 mg of product (75) in 59% yield.

{4-[2-Amino-4-(3-chloro-phenyl)-benzothiazol-6-ylmethyl]-phenyl}-urea. BA-27. Compound (75) (18 mg, 0.036 mmol) was dissolved in dichloromethane (1 mL). Trifluoroacetic acid (1 mL) was added. The mixture was stirred at rt for 1 hr. The volatile material was removed and the residue was partitioned between ethyl acetate (EA) and sodium bicarbonate. The EA layer was separated and dried over MgSO$_4$. Removal of solvent gave a residue, which was treated with 2N HCl in ether. The precipitate was collected by filtration. 20 mg of desired product BA-27 was obtained as HCl salt, which is a white solid (100% yield). LCMS: 97.6%. $^1$H-NMR (400 MHz, DMSO-d6)

BA-25,

BA-28

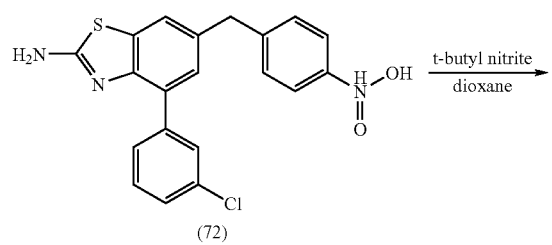

(72)

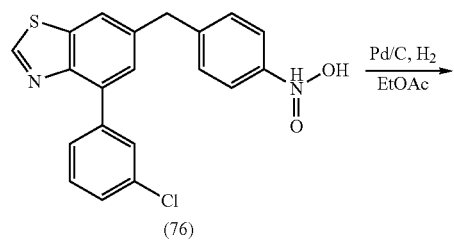

(76)

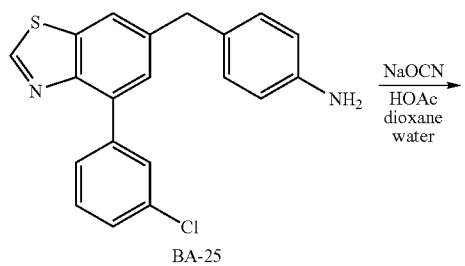

BA-25

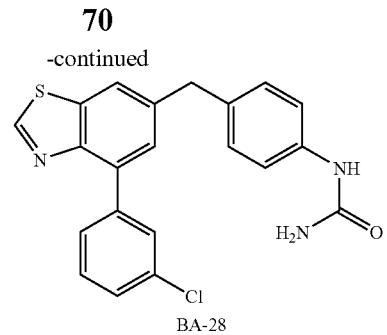

BA-28

4-(3-Chloro-phenyl)-6-(4-nitro-benzyl)-benzothiazole. (76). Compound (72) (109 mg, 0.27 mmol) was dissolved in dioxane (1 mL). To the solution was added t-butyl nitrite (60 mg, 0.55 mmol, 2 eq.) The mixture was stirred at 60 C for 30 min. After cooling to room temperature, the volatile material was removed under reduced pressure. The residue was purified by chromatography on silica gel using dichloromethane/hexane (1:1 then 1.5:1) as eluent to give 40 mg of (76) in 39% yield.

4-[4-(3-Chloro-phenyl)-benzothiazol-6-ylmethyl]-phenylamine. BA-25. Compound (76) (40 mg, 0.1 mmol) was dissolved in ethyl acetate (5 mL). Pd/C (100 mg, 10%, wet) was added and the mixture was stirred under H$_2$ (1 atm) for 2 h (the reaction was not complete). The catalyst was filtered and washed with ethyl acetate (5 mL×3). Removal of solvent under reduced pressure gave a residue, which was purified by chromatography on silica gel using DCM/Hexane (1:1) as eluent to give 10 mg of desired BA-25 (31% yield). The product was converted to its HCl salt by treatment with 2N HCl in ether. LCMS: 98%. $^1$H NMR {4-[4-(3-Chloro-phenyl)-benzothiazol-6-ylmethyl]-phenyl}-urea. BA-28. A mixture of compound BA-25 (8 mg, 0.02 mmol, HCl salt), NaOCN (10 mg, 0.15 mmol, 7 eq.) in HOAc (0.1 mL) and water (0.1 mL) was stirred at rt overnight. Then the mixture was diluted with addition of water. Solid was collected by filtration and purified by Prep TLC plate using DCM/MeOH (30:1) as developing system to give 3.6 mg of product BA-28 in 40% yield. $^1$H-NMR (400 MHz, DMSO-$d_6$).

BA-29

BA-30

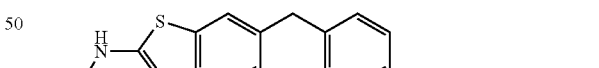

(48)

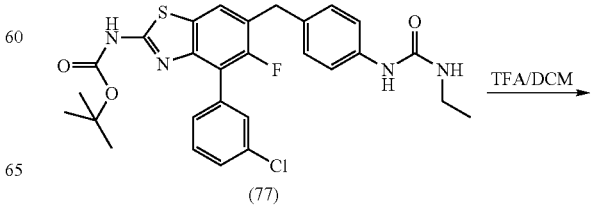

(77)

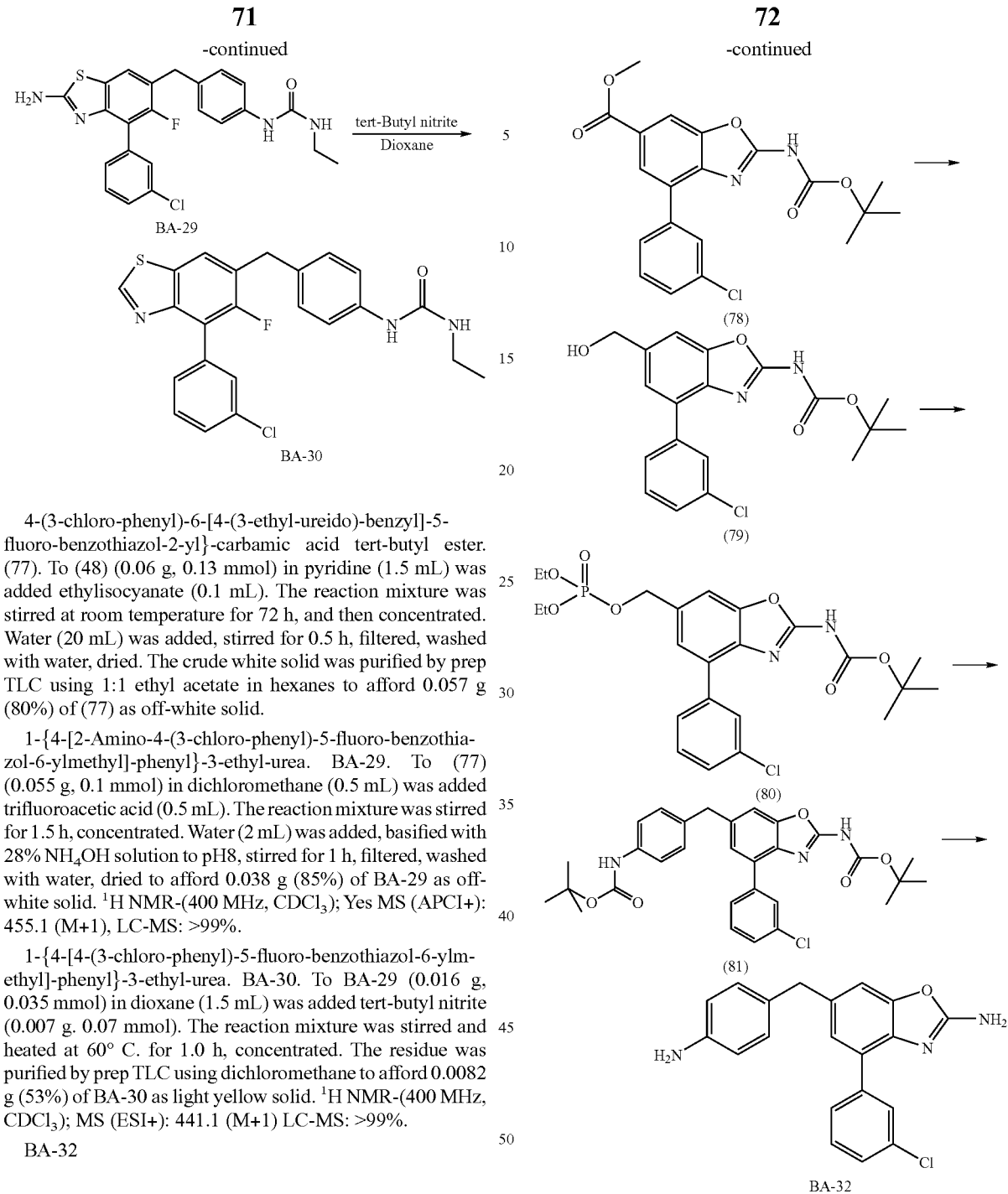

4-(3-chloro-phenyl)-6-[4-(3-ethyl-ureido)-benzyl]-5-fluoro-benzothiazol-2-yl}-carbamic acid tert-butyl ester. (77). To (48) (0.06 g, 0.13 mmol) in pyridine (1.5 mL) was added ethylisocyanate (0.1 mL). The reaction mixture was stirred at room temperature for 72 h, and then concentrated. Water (20 mL) was added, stirred for 0.5 h, filtered, washed with water, dried. The crude white solid was purified by prep TLC using 1:1 ethyl acetate in hexanes to afford 0.057 g (80%) of (77) as off-white solid.

1-{4-[2-Amino-4-(3-chloro-phenyl)-5-fluoro-benzothiazol-6-ylmethyl]-phenyl}-3-ethyl-urea. BA-29. To (77) (0.055 g, 0.1 mmol) in dichloromethane (0.5 mL) was added trifluoroacetic acid (0.5 mL). The reaction mixture was stirred for 1.5 h, concentrated. Water (2 mL) was added, basified with 28% NH₄OH solution to pH8, stirred for 1 h, filtered, washed with water, dried to afford 0.038 g (85%) of BA-29 as off-white solid. $^1$H NMR-(400 MHz, CDCl$_3$); Yes MS (APCI+): 455.1 (M+1), LC-MS: >99%.

1-{4-[4-(3-chloro-phenyl)-5-fluoro-benzothiazol-6-ylmethyl]-phenyl}-3-ethyl-urea. BA-30. To BA-29 (0.016 g, 0.035 mmol) in dioxane (1.5 mL) was added tert-butyl nitrite (0.007 g. 0.07 mmol). The reaction mixture was stirred and heated at 60° C. for 1.0 h, concentrated. The residue was purified by prep TLC using dichloromethane to afford 0.0082 g (53%) of BA-30 as light yellow solid. $^1$H NMR-(400 MHz, CDCl$_3$); MS (ESI+): 441.1 (M+1) LC-MS: >99%.

BA-32

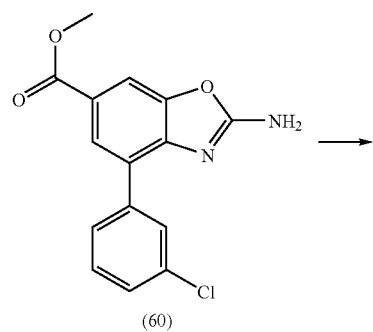

methyl 2-[(tert-butoxycarbonyl)amino]-4-(3-chlorophenyl)-1,3-benzoxazole-6-carboxylate. (78) To a suspension of (60) (1.43 g, 4.72 mmole) in 35 mL methylene chloride were added DMAP (60 mg, 10%) and BOC anhydride (1.08 g, 4.956 mmole). The reaction mixture was stirred at RT, for 24 hours. TLC shows 40% conversion. More DMAP (500 mg) and BOC anhydride (250 mg) were added and reaction mixture was stirred for one more day. Suspension was filtered off, solid was washed with methylene chloride. 695 mg of starting material was recovered. The filtrate was concentrated and purified by silicagel column chromatography using 20% to 50% ethylacetate/hexane to afford 755 mg product (78). $^1$H-NMR (400 MHz, DMSO)

tert-Butyl 4-(3-chlorophenyl)-6-(hydroxymethyl)-1,3-benzoxazol-2-ylcarbamate. (79). To a solution of (78) (560 mg, 1.39 mmole) in 15 mL anhydrous THF at 0° C. was added LiBH$_4$ (2M in THF, 2 mL, 3 eq.). The reaction mixture was stirred at room temperature for 3 days. TLC shows 40% conversion. More LiBH$_4$ (2 mL) was added and reaction mixture stirred at RT for one more day. The reaction was quenched with saturated solution of NH$_4$Cl, diluted with 5 mL water and extracted with ethylacetate. Combined organic layers were washed with water, brine, dried over Na$_2$SO$_4$, filtered and concentrated to give 790 mg crude. Purification by silicagel column chromatography gave 400 mg product (79) and 110 mg starting material (78). $^1$H-NMR (400 MHz, DMSO)

[4-(3-Chloro-phenyl)-6-(diethoxy-phosphoryloxymethyl)-benzooxazol-2-yl]-carbamic acid tert-butyl ester. (80). To a solution of (79) (100 mg, 0.266 mmole), TEA (0.055 mll, 1.5 eq.) and DMAP (4 mg, 10%) in 1 mL anhydrous THF at 0° C. was added diethylchlorophosphate (46 mg, 0.266 mmole). The reaction mixture was stirred at room temperature for 3 days. The reaction was diluted with 5% HCl and extracted 3× with ethyl acetate. Combined organic layers were washed with water, brine, dried over Na2SO4, filtered and concentrated to give 200 mg crude (80). This was used for next step. $^1$H-NMR (400 MHz, DMSO)

[6-(4-tert-Butoxycarbonylamino-benzyl)-4-(3-chlorophenyl)-benzooxazol-2-yl]-carbamic acid tert-butyl ester. (81). A suspension of (80) (200 mg, 0.39 mmole), potassium phosphate (91 mg, 0.429 mmole), boronic acid (102 mg, 0.429 mmole) in 4 mL dry toluene was degassed for 10 min using argon, then palladium acetate (5 mg, 5% eq.) and triphenyl phosphine (21 mg, 20% eq.) were added and the mixture was heated at 90° C. for 5 hours. The reaction mixture was cooled to room temperature, diluted with water and extracted with ethylacetate. Combined organic layers were washed with water, brine, dried over sodium sulfate, filtered and concentrated. The residue was purified by prep TLC using 5% MeOH/methylene chloride to obtain 120 mg product (81). $^1$H-NMR (400 MHz, CDCl$_3$)

6-(4-aminobenzyl)-4-(3-chlorophenyl)-1,3-benzoxazol-2-amine. BA-32. To a solution of (81) (100 mg, 0.22 mmole) in 1.5 mL methylene chloride was added 0.55 mL HCl 4N in dioxane. Solution became suspension and this was stirred at RT overnight. The mixture was diluted with diethylether and filtered off. The solid was triturated with ether and after filtration gave 35 mg BA-32 as HCl salt. $^1$H-NMR (400 MHz, DMSO). LCMS (APCI+): 350 (M+1), 87%.

BA-33

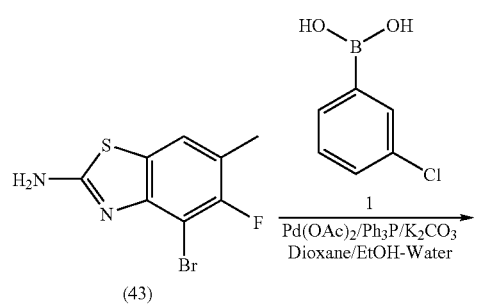

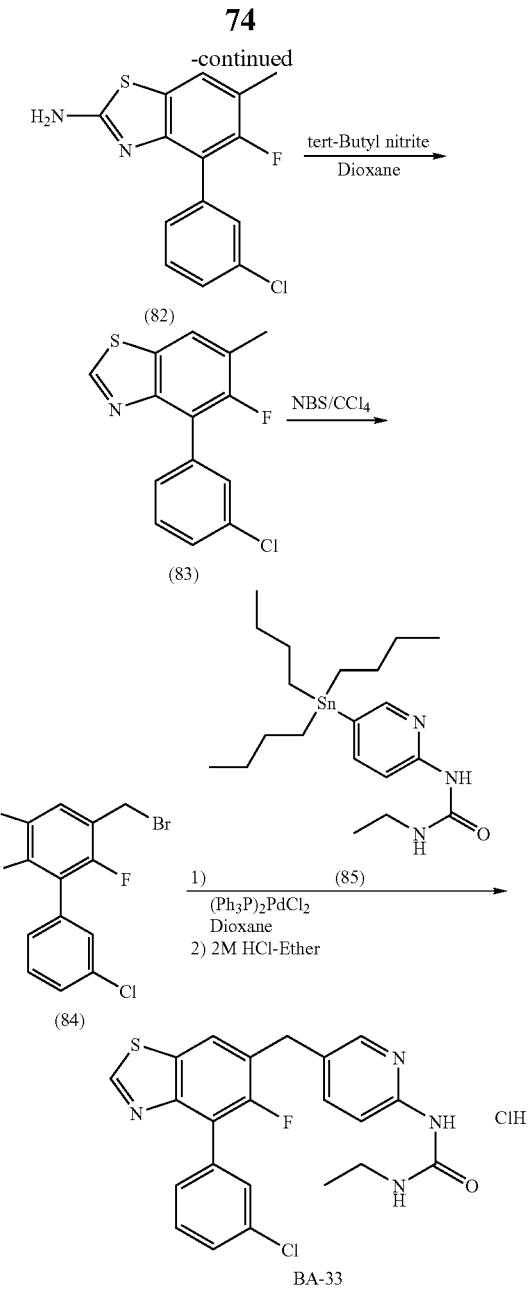

4-(3-chloro-phenyl)-5-fluoro-6-methyl-benzothiazol-2-ylamine. (82) To (43) (0.4 g, 1.53 mmol), 3-chlorophenylboronic acid (1) (0.29 g, 1.84 mmol), PPh$_3$ (0.2 g, 0.79 mmol), K$_2$CO$_3$ (0.08 g, 0.6 mmol) and Pd(OAc)$_2$ (0.04 g, 0.181 mmol) was added dioxane (8 mL), and EtOH—H$_2$O (1:1, 4 mL). Ar gas was bubbled through the stirred reaction for 15 min. The reaction was stirred at 180° C. for 15 minutes using microwave oven (Biotage Intiator II). Three more runs (0.5 g scale MR-49, total 1.9 g) were done under similar conditions. The reaction mixtures from all four runs were concentrated. Water (80 mL) and dichloromethane (80 mL) were added. The organic layer was separated and the aqueous layer was extracted with dichloromethane (2×40 mL). The combined organic extracts were dried with Na$_2$SO$_4$, filtered, and concentrated. The residue was purified by silica gel column chromatography using 30% ethyl acetate-hexanes to afford 1.18 g (55%) of (82) as a viscous liquid.

4-(3-chloro-phenyl)-5-fluoro-6-methyl benzothiazole (83) To (82) (0.986 g, 3.35 mmol) in dioxane (40 mL) was added tert-butyl nitrite (0.52 g. 5.02 mmol). The reaction mixture was stirred and heated at 60° C. for 1.0 h, concentrated. The residue was purified by silica gel column chromatography using 1:1 dichloromethane-hexanes to afford 0.57 g (61%) of (83) as light orange solid.

6-bromomethyl-4-(3-chloro-phenyl)-5-fluoro-benzothiazole. (84). To (83) (0.57 g, 2.05 mmol) and NBS (0.37 g, 2.05 mmol) in CCl$_4$ (30 mL) was added benzoylperoxide (0.01 g, 0.04 mmol). The reaction was stirred at 80° C. under N$_2$ for 18 h. The reaction was cooled to room temperature and concentrated. The residue was dissolved in mixture of dichloromethane and hexanes (1:1, 8 mL) and purified by silica gel column chromatography using 10% ethyl acetate-hexanes to afford 0.44 g (49%) of (84) as a light yellow solid.

1-[5-[4-(3-chloro-phenyl)-5-fluoro-benzothiazol-6-ylmethyl]-pyridin-2-yl]-3-ethyl-urea hydrochloride. BA-33.

Step-1. 5-tributylstannanyl-pyridin-2-yl)-urea. (85) To 5-iodo-pyridin-2-ylamine (0.5 g, 2.27 mmol) in pyridine (2.5 mL) was added ethylisocyanate (0.24 g, 3.4 mmol)). The reaction mixture was stirred at room temperature for 72 h, concentrated. Water (40 mL) was added, stirred for 0.5 h, filtered, washed with water, dried to afford 0.61 g (92%) of 1-ethyl-3-(5-iodo-pyridin-2-yl)-urea, MR-66, as white solid. To MR-66 (0.5 g, 1.72 mmol) and bis-tributyltin (5.6 g, 9.64 mmol) in dioxane (25 mL) was added bis-triphenylphosphine palladium dichloride (0.28 g, 0.4 nmol). Ar gas was bubbled through the stirred reaction for 5 min. The reaction was stirred at 90° C. under Ar for 20 h. The reaction was cooled to room temperature, concentrated. The residue was purified by silica gel column chromatography using 30% ethyl acetate in hexanes to afford 0.41 g (53%) of (85) as viscous liquid.

Step-2. BA-33. To (84) (0.065 g, 0.18 mmol) and (85) (0.08 g, 0.22 mmol) in dimethoxyethane (2 mL) was added bis-triphenylphosphine palladium dichloride (0.006 g, 0.009 mmol). Ar gas was bubbled through the stirred reaction for 2 min. The reaction was stirred at 120° C. for 15 minutes using microwave oven (Biotage Intiator 11). The reaction was cooled to room temperature, concentrated. The residue was purified by silica gel column chromatography using 30% ethyl acetate in hexanes dichloromethane-hexanes afforded 0.042 g of light orange solid. The solid was suspended in ether (1.5 mL), than 2M HCl in ether (0.7 mL) was added. The reaction mixture was stirred for 1 h. The ether layer was decanted, triturated with ether (2×1 mL), dried to afford 0.022 g (25%) of BA-33 as yellow solid. $^1$H NMR-(400 MHz, CDCl$_3$); MS (APCI+): 441.00 (M+1), LC-MS: 97%.

BA-38

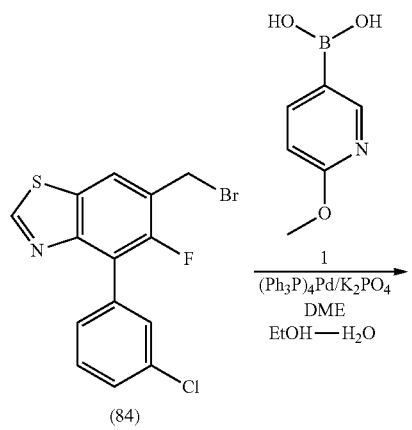

4-(3-chloro-phenyl)-5-fluoro-6-(6-methoxy-pyridin-3-yl-methyl)-benzothiazole hydrochloride. (BA-38). To (84) (0.06 g, 0.17 mmol), 2-methoxy-5-pyridineboronic acid (1) (0.04 g, 0.25 mmol), (PPh$_3$)$_4$Pd (0.02 g, 0.017 mmol) and K$_2$PO$_4$ (0.07 g, 0.034 mmol) was added DME (1.5 mL), and EtOH— H$_2$O (1:1, 0.5 mL). Ar gas was bubbled through the stirred reaction for 5 min. The reaction was stirred at 150° C. for 15 minutes using microwave oven (Biotage Initiator II). The reaction was cooled to room temperature, concentrated. The residue was purified by silica gel column chromatography using dichloromethane to afford 0.036 g (56%) of the target compound (BA-38, free-base) as viscous liquid. To the free-base (0.034 g, 0.088 mmol) in ether (2.0 mL) was added 2M HCl in ether (0.5 mL). The reaction mixture was stirred for 1 h. The ether layer was decanted, triturated with ether (2×2 mL), dried to afford 0.035 g (94%) of BA-38, HCl salt, as off-white solid. $^1$H NMR-(400 MHz, CDCl$_3$); MS (APCI+): 385.0 (M+1), LC-MS: 96%.

BA-39

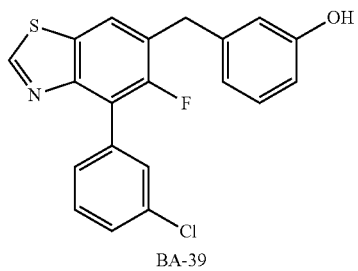

BA-39

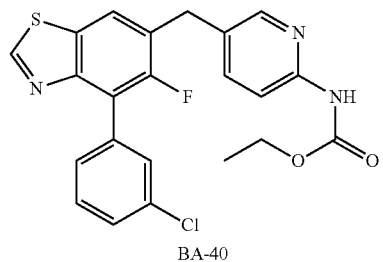

BA-40

3-[4-(3-chloro-phenyl)-5-fluoro-benzothiazol-6-ylmethyl]-phenol. BA-39. To (84) (0.08 g, 0.22 mmol), 3-hydroxyphenylboronic acid (1) (0.046 g, 0.34 mmol), (PPh$_3$)$_4$Pd (0.026 g, 0.02 mmol) and K$_2$PO$_4$ (0.095 g, 0.045 mmol) was added DME (3 mL), and EtOH—H$_2$O (1:1, 1.0 mL). Ar gas was bubbled through the stirred reaction for 5 min. The reaction was stirred at 160° C. for 20 minutes using microwave oven (Biotage Intiator 11). The reaction was cooled to room temperature, concentrated. The residue was purified by silica gel column chromatography using dichloromethane to afford 0.056 g (68%) of BA-39 as viscous liquid. $^1$H NMR-(400 MHz, CDCl$_3$); MS (APCI+): 371.1 (M+1), LC-MS: >99%.

BA-40

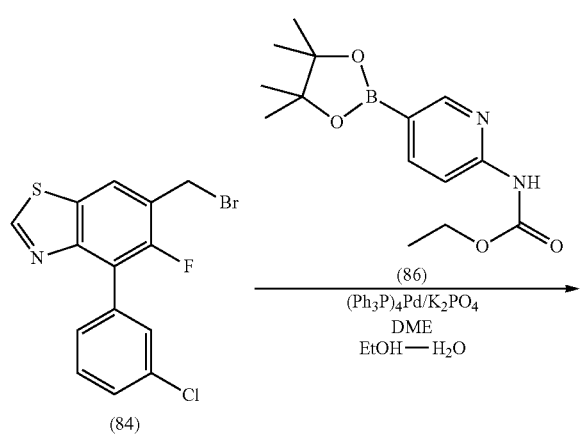

{5-[4-(3-chloro-phenyl)-5-fluoro-benzothiazol-6-ylmethyl]-pyridin-2-yl}-carbamic acid ethyl ester, BA-40. Step-1 (86). To 5-(4,4,5,5-tetramethyl-[1,3,2]dioxaborolan-2-yl)-pyridin-2-ylamine (0.2 g, 0.91 mmol) in pyridine (2.5 mL) was added ethyl chloroformate (0.15 g, 1.36 mmol)). The reaction mixture was stirred at room temperature for 18 h, concentrated. Water (1.0 mL) and saturated NaHCO$_3$ solution (1.0 mL) was added, stirred for 1.0 h, filtered, washed with water, dried to afford 0.16 g (60%) of (86), as white solid.

BA-40: To (84) (0.08 g, 0.22 mmol), MR-75 (0.1 g, 0.34 mmol), (PPh$_3$)$_4$Pd (0.026 g, 0.02 mmol) and K$_2$PO$_4$ (0.095 g, 0.45 mmol) was added DME (3.0 mL), and EtOH—H$_2$O (1:1, 1.0 mL). Ar gas was bubbled through the stirred reaction for 5 min. The reaction was stirred at 160° C. for 20 minutes using microwave oven (Biotage Initiator 11). The reaction was cooled to room temperature, concentrated. The residue was purified by silica gel column chromatography using dichloromethane followed by triturating with methanol to afford 0.03 g (30%) of BA-40 as off-white solid. $^1$H NMR-(400 MHz, CDCl$_3$); MS (APCI+): 442.0 (M+1), LC-MS: 86%.

Followed the same procedure as for BA-40 using (84).

Scheme. piperazine analogs

BA-31
BA-43
BA-44
BA-45
BA-46
BA-47
BA-48
BA-49
BA-50

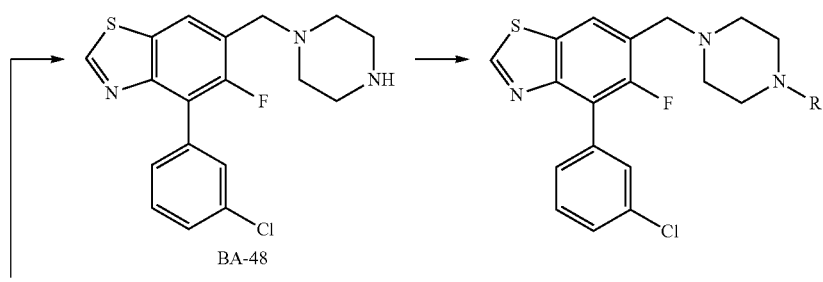

BA-48

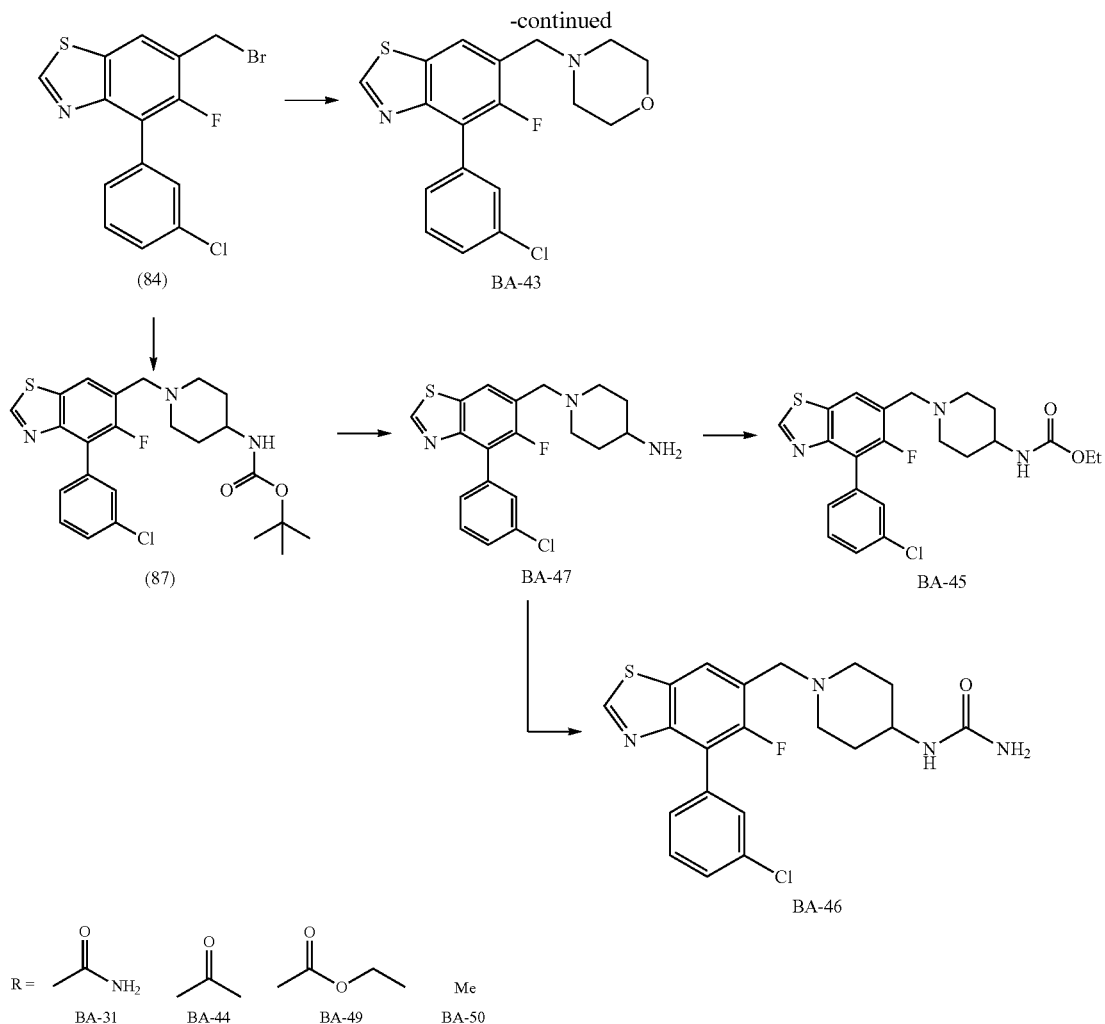

BA-48

4-(3-Chloro-phenyl)-5-fluoro-6-piperazin-1-ylmethyl-benzothiazole. BA-48. To a solution of piperazine (821 mg, 9.53 mmol, 10 eq.) in 15 mL anh. THF, at room temperature was added a solution of (84) (340 mg, 0.953 mmol) in 5 mL anh. THF. The reaction mixture was stirred at room temperature for 2 hours. The mixture was concentrated down, diluted with water, and filtrated to give solid crude. This was triturated with 5 mL ether, and after filtration and drying afforded 280 mg (81.4%) of BA-48 as a white solid. $^1$H-NMR-(400 MHz, DMSO). LCMS (APCI+): 362 (M+1), 99%.

BA-49

4-[4-(3-Chloro-phenyl)-5-fluoro-benzothiazol-6-ylmethyl]-piperazine-1-carboxylic acid ethyl ester. BA-49 To a solution of BA-48 980 mg, 0.22 mmole) in 1.5 mL anh. THF was added at room temperature pyridine (35 mg, 36 µL, 2 eq.). This mixture was cooled to 0° C. and ethylchloroformate (48 mg, 0.44 mmole) was added. Reaction mixture was stirred at room temperature for 24 hrs. Mixture was concentrated, diluted with water and extracted 3 times with methylene chloride. Combined organic layers were washed with brine, dried over $Na_2SO_4$, filtered and concentrated to give about 100 mg crude. Purification by silicagel prep plate provided 80 mg (84.21%) of BA-49 as white foam. $^1$H-NMR-(400 MHz, DMSO). LCMS (APCI+): 434 (M+1), 100%.

BA-31

4-[4-(3-Chloro-phenyl)-5-fluoro-benzothiazol-6-ylmethyl]-piperazine-1-carboxylic acid amide. BA-31. To a solution of BA-48 (70 mg, 0.2 mmole) in 1.5 mL methylene chloride was added at 0° C. trimethyl silyl isocyanate (46 mg, 0.4 mmole). The reaction mixture was stirred at room temperature for 24 hrs. Mixture was quenched by slowly addition of saturated sol. of $NaHCO_3$ and extracted 3 times with methylene chloride. Combined organic layers were washed with brine, dried over $Na_2SO_4$, filtered and concentrated to give about 100 mg crude. Purification by silica gel preparative plate provided 20 mg (25.6%) of BA-31 as a white solid, 25. $^1$H-NMR-(400 MHz, DMSO). LCMS (APCI+): 405 (M+1), 92%.

BA-43

4-(3-Chloro-phenyl)-5-fluoro-6-morpholin-4-ylmethyl-benzothiazole. BA-43. To a solution of BA-48 (45 mg, 0.126 mmol) in 1.5 mL methylene chloride was added diisopropyl ethylamine (25 mg, 0.19 mmol) and morpholine (12 mg, 0.138 mmole). The reaction mixture was stirred at room temperature for 24 hrs. Mixture was concentrated down, redissolved in ethyl acetate and washed with water. Organic layer was washed with water, brine, dried over $Na_2SO_4$, filtered and concentrated to give about 50 mg solid BA-43. $^1$H-NMR-(400 MHz, $CDCl_3$). LCMS (APCI+): 363 (M+1), 97%.

BA-44

1-{4-[4-(3-Chloro-phenyl)-5-fluoro-benzothiazol-6-ylmethyl]-piperazin-1-yl}-ethanone. BA-44.

To a solution of BA-48 (80 mg, 0.22 mmole) in 1.5 mL methylene chloride was added at 0° C. pyridine (26 mg, 0.33 mmole) followed by addition of acetyl chloride (26 mg, 0.33 mmole). The reaction mixture was stirred at room temperature for 3 hrs. Mixture was diluted with water and extracted 3 times with methylene chloride. Combined organic layers were washed with brine, dried over Na$_2$SO$_4$, filtered and concentrated to give about 80 mg crude. Purification by silicagel prep plate using 5% methanol/methylene chloride provided 40 mg (45%) of BA-44. $^1$H-NMR-(400 MHz, DMSO). LCMS (APCI+): 405 (M+1), 100%.

BA-50

4-(3-Chloro-phenyl)-5-fluoro-6-(4-methyl-piperazin-1-ylmethyl)-benzothiazole. BA-50. A small vial containing BA-48 (60 mg, 0.165 mmole), 0.1 mL formic acid and 0.1 mL formaldehyde was sealed and heated 40 minutes @ 160° C. using microwave Biotage Initiator. The reaction mixture was basified to pH=8 using saturated solution of NaHCO$_3$ and extracted 3 times with methylene chloride. Combined organic layers were washed with brine, dried over Na$_2$SO$_4$, filtered and concentrated to give about 60 mg crude. Purification by silicagel prep plate using 5% methanol/methylene chloride provided 50 mg (79%) of BA-50. $^1$H-NMR-(400 MHz, CDCl$_3$). LCMS (APCI+): 376 (M+1), 92.5%.

BA-47

Step-1: [1-[4-(3-Chloro-phenyl)-5-fluoro-benzothiazol-6-ylmethyl]-piperidin-4-yl]-carbamic acid tert-butyl ester. (87). To a solution of (84) (114 mg, 0.32 mmole) in 3 ml methylene chloride was added diisopropyl ethylamine (62 mg, 0.48 mmole) and 4(N-BOC amino) piperidine (68 mg, 0.32 mmole). The reaction mixture was stirred at room temperature for 24 hrs. Mixture was concentrated down to afford 200 mg foamy crude, (87). $^1$H-NMR-(400 MHz, CDCl3)

Step-2: [1-[4-(3-Chloro-phenyl)-5-fluoro-benzothiazol-6-ylmethyl]-piperidin-4-yl]-carbamic acid tert-butyl ester. BA-47.

To a solution of (87) (195 mg, 0.41 mmole) in 2 mL methylene chloride was added at 0° C. 1.1 mL of HCl 4N in dioxane. The reaction mixture was stirred at room temperature for 8 hrs. Mixture was concentrated down and solid residue was triturated with 5 mL ether to give 190 mg the desired product, BA-47, as HCl salt. A small amount was converted to free base using saturated NaHCO$_3$. $^1$H-NMR-(400 MHz, CDCl$_3$). LCMS (APCI+): 376 (M+1), 100%.

BA-45

{1-[4-(3-Chloro-phenyl)-5-fluoro-benzothiazol-6-ylmethyl]-piperidin-4-yl}-carbamic acid ethyl ester. BA-45. To a solution of BA-47 (100 mg, 0.25 mmol) in 1.5 mL anhydrous THF was added pyridine (60 mg, 0.75 mmol) and at 0° C. ethylchloroformate (60 mg, 0.5 mmol). The reaction mixture was stirred at room temperature for 24 hrs. Mixture was concentrated down, diluted with water and extracted 3 times with ethyl acetate. Combined organic layers were washed with brine, dried over Na$_2$SO$_4$, filtered and concentrated. Trituration of the crude with ether afforded 30 mg solid BA-45. $^1$H-NMR-(400 MHz, CDCl$_3$). LCMS (APCI+): 448 (M+1), 100%.

BA-46

[1-[4-(3-Chloro-phenyl)-5-fluoro-benzothiazol-6-ylmethyl]-piperidin-4-yl]-urea. BA-46.

To a solution of BA-47 (60 mg, 0.145 mmole) in 1.5 mL methylene chloride was added triethylamine (30 mg, 0.29 mmole) and at 0° C. trimethyl silyl isocyanate (50 mg, 0.435 mmole). The reaction mixture was stirred at room temperature for 24 hrs. Mixture was quenched by slowly addition of saturated sol. of NaHCO$_3$ and extracted 3 times with methylene chloride. Combined organic layers were washed with brine, dried over Na$_2$SO, filtered and concentrated. Purification by silicagel prep plate provided 15 mg product BA-46 as white solid. $^1$H-NMR-(400 MHz, CDCl$_3$). LCMS (APCI+): 419 (M+1), 100%.

BA-52

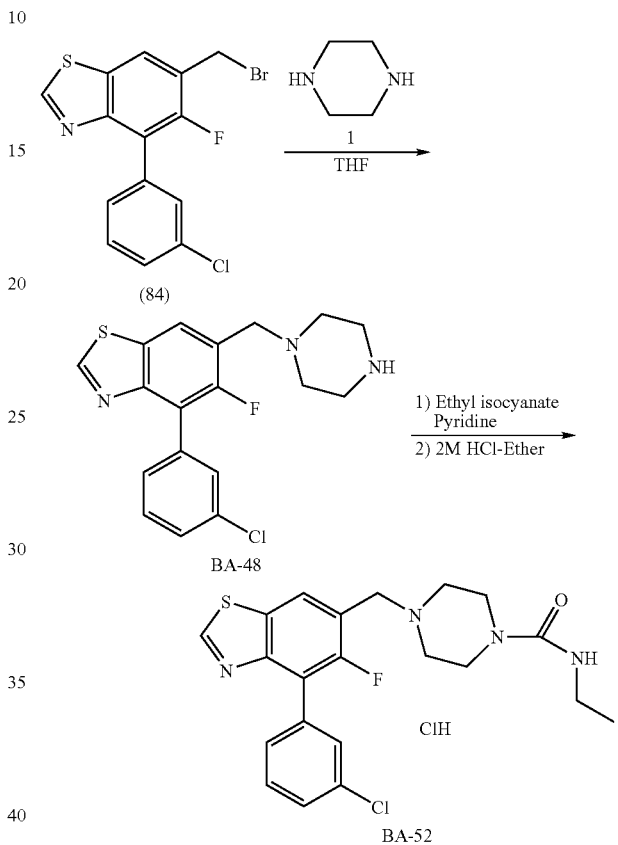

BA-52

4-(3-chloro-phenyl)-5-fluoro-6-piperazin-1-ylmethyl-benzothiazole: BA-48 To (84) (0.1 g, 0.28 mmol) in tetrahydrofuran (7.0 mL) was added a solution of piperazine (1) (0.24 g, 2.8 mmol) in tetrahydrofuran (1.0 mL) over 10 min. The reaction was stirred at room temperature for 18 h. The reaction mixture was concentrated, washed with saturated NaHCO$_3$ solution (2 mL), water (2×2 mL) than ether ((2×2 mL). The residue was dissolved in dichloromethane, dried (Na$_2$SO$_4$), filtered and concentrated to afford 0.086 g (85%) of BA-48 as light yellow solid. $^1$H NMR (400 MHz, CDCl$_3$).

4-[4-(3-chloro-phenyl)-5-fluoro-benzothiazol-6-ylmethyl]-piperazine-1-carboxylic acid ethylamide hydrochloride. BA-52.

To BA-48 (0.08 g, 0.22 mmol) in pyridine (1.5 mL) was added ethylisocyanate (0.05 mL). The reaction mixture was stirred at room temperature for 18 h, concentrated. Water (10 mL) was added, stirred for 0.5 h, filtered, washed with water (5 mL). The residue was dissolved in dichloromethane, dried (Na$_2$SO$_4$), filtered and concentrated. The crude yellow solid was purified by prep TLC using 5% methanol in dichloromethane to afford 0.06 g of light yellow solid. The light yellow solid was dissolved in ether (2.0 mL) was added 2M HCl in ether (1.0 mL). The reaction mixture was stirred for 2 h at room temperature, concentrate under N$_2$ flow, than dried under vacuum to afford 0.06 g (63%) of BA-52 as off-white solid. ¹H NMR (400 MHz, CDCl₃); MS (APCI+): 433.1 (M+1), LC-MS: 88%.

BA-51

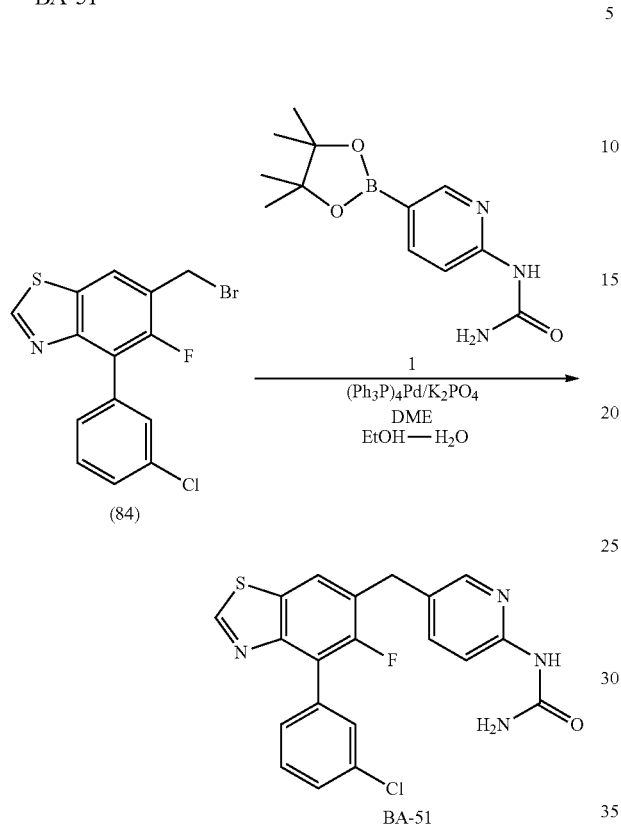

(84)

BA-51

(MR 77) Synthesis of {5-[4-(3-chloro-phenyl)-5-fluoro-benzothiazol-6-ylmethyl]-pyridin-2-yl}-carbamic acid ethyl ester: To benzyl bromide (84) (0.08 g, 0.22 mmol), [4-(4,4,5,5-tetramethyl-[1,3,2]dioxaborolan-2-yl)-phenyl]-urea (1) (0.07 g, 0.27 mmol), (PPh₃)₄Pd (0.026 g, 0.02 mmol) and K₂PO₄ (0.095 g, 0.45 mmol) was added DME (3.0 mL), and EtOH—H₂O (1:1, 1.5 mL). Ar gas was bubbled through the stirred reaction for 5 min. The reaction was stirred at 120° C. for 20 minutes using microwave oven (Biotage Intiator II). The reaction was cooled to room temperature, concentrated. The residue was purified by silica gel column chromatography using 5% methanol in dichloromethane followed by prep TLC using 5% methanol in dichloromethane to afford 0.015 g (16%) of BA-51 as light brown solid. 1H NMR (DMSO-d6, 400 MHz): 9.39 (s, 1 H), 8.45 (s, 1 H), 8.1 (d, J=7.2 Hz, 1 H), 7.66 (s, 1H), 7.5-7.59 (m, 4H), 7.32 (d, J=8.5 Hz, 2 H), 7.14 (d, J=8.5 Hz, 2 H), 5.77 (s, 2 H), 4.06 ppm (s, 2 H); MS (APCI+): 412.0 (M+1), LC-MS: 97%.

BA-53

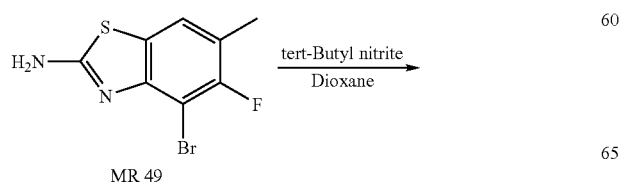

MR 49

-continued

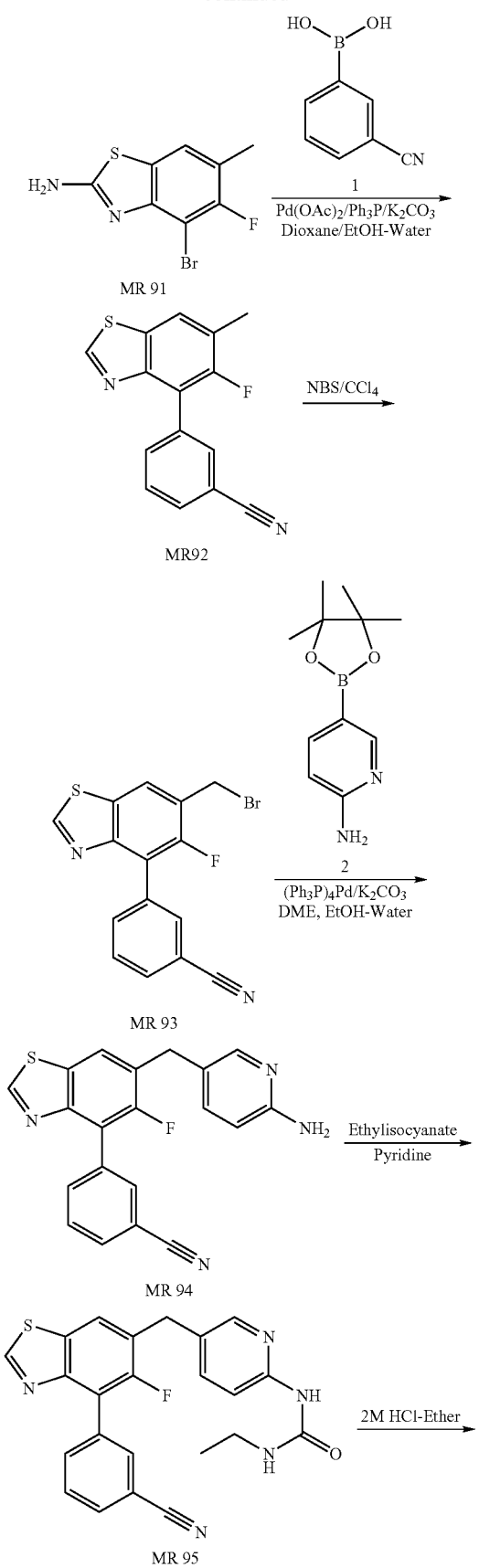

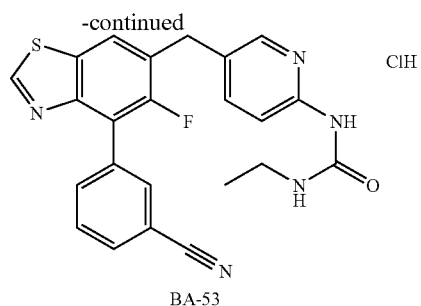

BA-53

(MR 91) Synthesis of 5-fluoro-6-methyl-benzothiazol-2-ylamine: To MR 49 (1.0 g, 3.83 mmol) in dioxane (30 mL) was added tert-butyl nitrite (0.59 g. 5.12 mmol). The reaction mixture was stirred and heated at 60° C. for 1.5 h, concentrated. The residue was purified by silica gel column chromatography using 1:1 dichloromethane-hexanes to afford 0.45 g (47%) of MR 91 as reddish orange solid.

(MR 92) Synthesis of 3-(5-fluoro-6-methyl-benzothiazol-4-yl)-benzonitrile: To MR 91 (0.44 g, 1.79 mmol), 3-cyanophenylboronic acid (1) (0.32 g, 2.15 mmol), PPh$_3$ (0.23 g, 0.89 mmol), K$_2$CO$_3$ (0.1 g, 0.72 mmol) and Pd(OAc)$_2$ (0.05 g, 0.21 mmol) was added dioxane (8 mL), and EtOH—H$_2$O (1:1, 4 mL). Ar gas was bubbled through the stirred reaction for 15 min. The reaction was stirred at 180° C. for 15 minutes using microwave oven (Biotage Intiator II). The reaction mixture was concentrated. Water (50 mL) and dichloromethane (50 mL) were added. The organic layer was separated and the aqueous layer was extracted with dichloromethane (2×40 mL). The combined organic extracts were dried with Na$_2$SO$_4$, filtered, and concentrated. The residue was purified by silica gel column chromatography using 1:1 dichloromethane-hexanes than 80% dichloromethane in to afford 0.39 g (81%) of MR 92 as off-white solid.

(MR 93) Synthesis of 3-(6-bromomethyl-5-fluoro-benzothiazol-4-yl)-benzonitrile: To MR 92 (0.39 g, 1.45 mmol) and NBS (0.27 g, 1.53 mmol) in CCl$_4$ (20 mL) was added benzoylperoxide (0.04 g, 0.14 mmol). The reaction was stirred at 80° C. under N$_2$ for 5 h. The reaction was cooled to room temperature and concentrated. The residue was dissolved in mixture of dichloromethane and hexanes (1:1, 8 mL) and purified by silica gel column chromatography using 20% ethyl acetate-hexanes to afford 0.21 g (41%) of MR 93 as white solid.

(MR 94) Synthesis of 3-[6-(6-amino-pyridin-3-ylmethyl)-5-fluorobenzothiazol-4-yl]-benzonitrile: To MR 93 (0.2 g, 0.58 mmol), 5-(4,4,5,5-Tetramethyl-[1,3,2]dioxaborolan-2-yl)-pyridin-2-ylamine (2) (0.15 g, 0.7 mmol), (PPh$_3$)$_4$Pd (0.07 g, 0.06 mmol) and K$_3$PO$_4$ (0.24 g, 1.15 mmol) was added DME (8.0 mL), and EtOH—H$_2$O (1:1, 4.0 mL). Ar gas was bubbled through the stirred reaction for 5 min. The reaction was stirred at 120° C. for 20 minutes using microwave oven (Biotage Intiator II). The reaction was cooled to room temperature, concentrated. The residue was purified by silica gel column chromatography using 5% methanol in dichloromethane followed by prep TLC using 6% methanol in dichloromethane to afford 0.08 g (39%) of MR 94 as off-white solid.

(MR 95) Synthesis of 1-{5-[4-(3-cyano-phenyl)-5-fluoro-benzothiazol-6-ylmethyl]-pyridin-2-yl}-3-ethyl-urea: To MR 94 (0.075 g, 0.21 mmol) in pyridine (1.5 mL) was added ethylisocyanate (0.044 mL). The reaction mixture was stirred at room temperature for 18 h, concentrated. Water (10 mL) was added, stirred for 0.5 h, filtered, washed with water (5 mL), ethyl acetate (2×5 mL), than ether (10 mL), dried to afford 0.036 g (40%) of MR 95 as white solid.

(MR 96). Synthesis of 1-{5-[4-(3-cyano-phenyl)-5-fluoro-benzothiazol-6-ylmethyl]-pyridin-2-yl}-3-ethyl-urea hydrochloride (BA-53): To MR 95 (0.032 g, 0.07 mmol) in ether (1.0 mL) was added 2M HCl in ether (0.2 mL, 0.4 mmol). The reaction mixture was stirred for 2 h at room temperature, concentrate under N$_2$ flow, than dried under vacuum to afford 0.036 g (98%) of MR 96 as off-white solid. 1H NMR (DMSO-d6, 400 MHz): 9.44 (s, 1 H), 8.16-8.2 (m, 2 H), 8.09 (s, 1 H), 7.92-7.98 (m, 3 H), 7.78-7.86 (m, 2 H), 7.7-7.76 (m, 2 H), 7.32 (d, J=9.2 Hz, 1 H), 4.15 (s, 2 H), 3.14-3.22 (m, 2 H), 1.08 ppm (t, J=7.2 Hz, 3 H); MS (APCI+): 432.0 (M+1), LC-MS: 92%.

BB-01

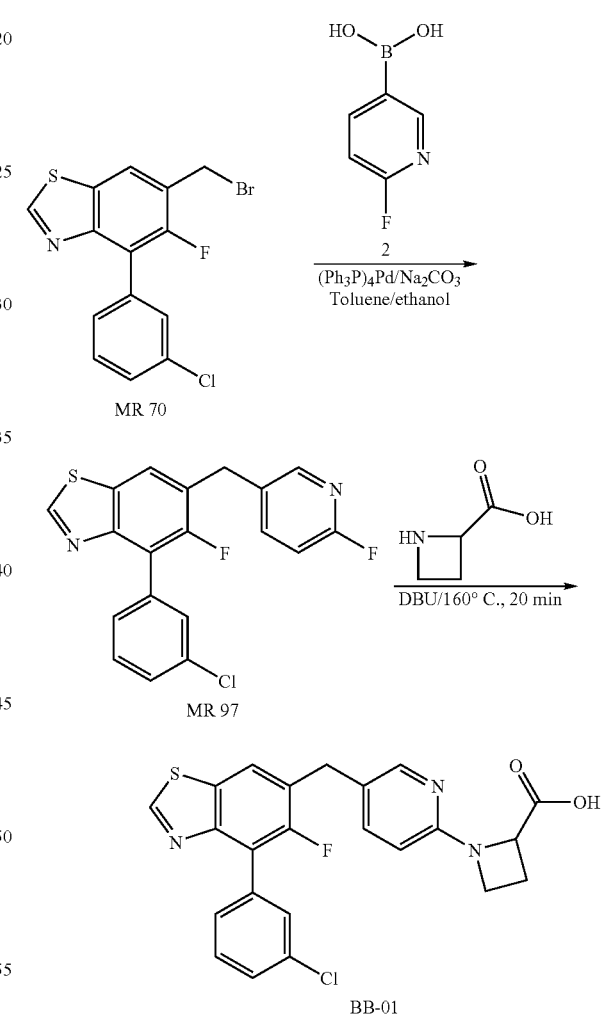

(MR 97) Synthesis of 4-(3-chloro-phenyl)-5-fluoro-6-(6-fluoro-pyridin-3-ylmethyl)-benzothiazole: To MR 70 (0.6 g, 1.68 mmol), 2-fluoro-5-pyridineboronic acid (2) (0.24 g, 1.68 mmol) and (PPh$_3$)$_4$Pd (0.1 g, 0.08 mmol) was added toluene (20.0 mL), and EtOH (5.0 mL). The reaction mixture stirred for 5 min, than Na2CO3 (2M soln, 1.7 mL, 3.36 mmol) was added. Ar gas was bubbled through the stirred reaction for 15 min. Then the reaction was stirred at 80° C. for 18 h. The reaction was cooled to room temperature, concentrated. The residue was diluted with water (40 mL), extracted with ethyl acetate (2×30 mL), washed with brine (30 mL), dried with Na₂SO₄, filtered, and concentrated. The residue was purified by silica gel column chromatography using dichloromethane to afford 0.48 g (76%) of MR 97 as off-white solid.

(MR 98). Synthesis of 1-{5-[4-(3-chloro-phenyl)-5-fluoro benzothiazol-6-ylmethyl]-pyridin-2-yl}-azetidine-2-carboxylic acid (BB-01): To MR 97 (0.07 g, 0.19 mmol) and D,L-azetidine-2-carboxylic acid (2) (0.06 g, 0.56 mmol) was added 1,8-diazabicyclo[5.4.0]undec-7-ene (DBU) (0.14 g, 0.94 mmol). The reaction mixture was stirred and heated at 160° C. for 20 min. Cooled to room temperature, diluted with dichloromethane (6 mL), washed with 0.5 N HCl (2×2 mL), dried with Na₂SO₄, filtered, and concentrated. The residue was purified by silica gel column chromatography using 5% methanol in dichloromethane to afford 0.022 g (23%) of BB-01 as light yellow solid. 1H NMR (DMSO-d6, 400 MHz): 9.35 (s, 1 H), 8.12 (d, J=7.2 Hz, 1 H), 8.05 (s, 1 H), 7.66 (s, 1 H), 7.45-7.59 (m, 4 H), 6.41 (d, J=8.4 Hz, 1 H), 4.58 (dd, J=8, 6.8 Hz, 1 H), 4.03 (s, 2 H), 3.72-3.8 (m, 2 H), 2.3-2.41 (m, 2 H); MS (APCI+): 454.1 (M+1), LC-MS: 99%.

BB-03

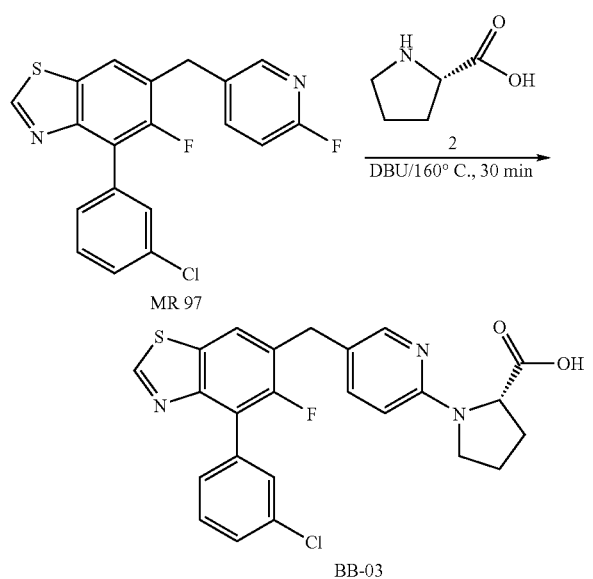

(MR 100). Synthesis of (S)-1-{5-[4-(3-chloro-phenyl)-5-fluoro-benzothiazol-6-ylmethyl]-pyridin-2-yl}-pyrrolidine-2-carboxylic acid (BB-03): To MR 97 (0.15 g, 0.4 mmol) and (S)-Pyrrolidine-2-carboxylic acid (2) (0.1 g, 0.8 mmol) was added 1,8-diazabicyclo[5.4.0]undec-7-ene (DBU) (0.31 g, 2.01 mmol). The reaction mixture was stirred and heated at 160° C. for 30 min. Cooled to room temperature, diluted with dichloromethane (10 mL), washed with 0.5 N HCl (2×4 mL), dried with Na₂SO₄, filtered, and concentrated to afford 0.18 g (94%) of BB-03 as light yellowish-brown solid. 1H NMR (DMSO-d6, 400 MHz): 9.42 (s, 1 H), 8.16 (d, J=6.8 Hz, 1 H), 8.0 (s, 1 H), 7.72-7.82 (br s, 1 H), 7.67 (s, 1 H), 7.5-7.59 (m, 4 H), 6.8-6.88 (br s, 1 H), 4.64 (br s, 1 H), 4.11 (s, 2 H), 3.4-3.65 (m, 2 H), 1.88-2.3 (m, 4 H); MS (APCI+): 468.1 (M+1), LC-MS: 99%

BA-54

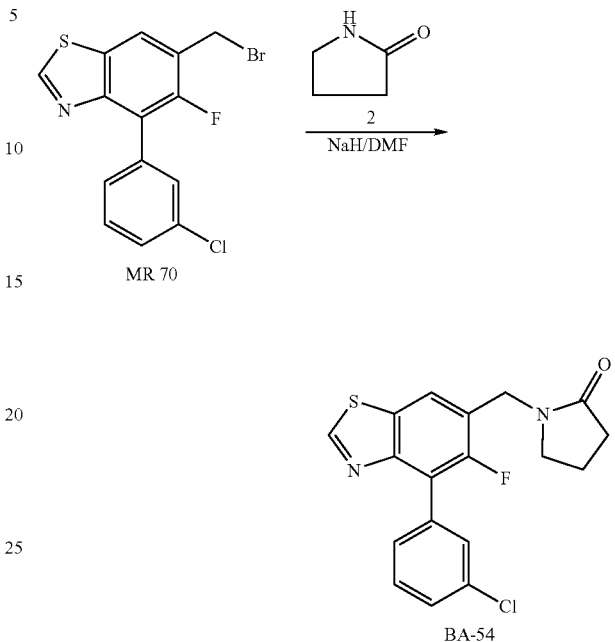

(MR 101). Synthesis of 1-[4-(3-Chloro-phenyl)-5-fluoro-benzothiazol-6-ylmethyl]-pyrrolidin-2-one (BA-54): To a cooled (0° C.) and stirred suspension of NaH (0.034 g, 0.84 mmol) in DMF (2.0 mL) was added a solution of pyrrolidine-2-one (0.07 g, 0.84 mmol) in DMF (0.5 ml). The reaction mixture was slowly warmed to room temperature, stirred for 0.5 h. Again cooled (0° C.), then a solution of MR 70 (0.15 g, 0.42 mmol) in DMF (0.5 mL) was added over 5 min. The reaction mixture was slowly warmed to room temperature, stirred for 2 h. Poured on to crushed ice-water, extracted with ethyl acetate (2×40 mL). The combined organic extracts were dried with Na₂SO4, filtered, and concentrated. The residue was purified by preparative thin layer chromatography using 1% methanol in dichloromethane to afford 0.087 g (58%) of BA-54 as a viscous liquid. 1H NMR (DMSO-d6, 400 MHz): 9.44 (s, 1 H), 8.11 (d, J=6.8 Hz, 1 H), 7.69 (s, 1 H), 7.5-7.62 (m, 4 H), 4.6 (s, 2 H), 3.37 (t, J=7.2 Hz, 2 H), 2.33 (t, J=7.2 Hz, 2 H), 1.95-2.06 (m, 2 H); MS (APCI+): 361.0 (M+1), LC-MS: 100%.

BA-55

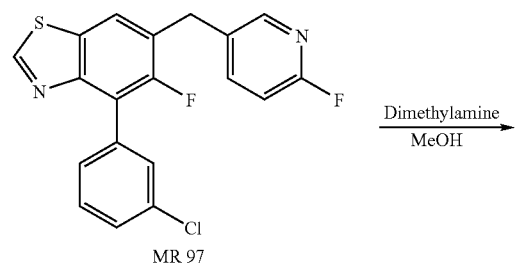

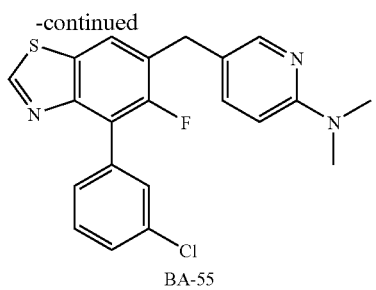

BA-55

(MR 102). Synthesis of {5-[4-(3-chloro-phenyl)-5-fluoro-benzothiazol-6-ylmethyl]-pyridin-2-yl}-dimethyl-amine (BA-55): To MR 97 (0.1 g, 0.27 mmol) was added 2M solution of dimethylamine in methanol (2 mL, 4 mmol). Vial was sealed and heated at 140° C. for 40 min. using Biotage intiator 11 microwave oven. The reaction mixture was concentrated, the residue was purified by preparative thin layer chromatography using 5% methanol in dichloromethane to afford 0.06 g (56%) of BA-55 as off-white solid. 1H NMR (DMSO-d6, 400 MHz): 9.39 (s, 1 H), 8.11 (d, J=6.8 Hz, 1 H), 8.05 (d, J=2.0 Hz, 1 H), 7.6 (s, 1 H), 7.5-7.59 (m, 3 H), 7.41 (dd, J=8.4, 2.4 Hz, 1 H), 6.59 (d, J=8.4 Hz, 1 H), 4.0 (s, 2 H), 2.97 (s, 6 H); MS (APCI+): 398.1 (M+1), LC-MS: 100%.

BA-57

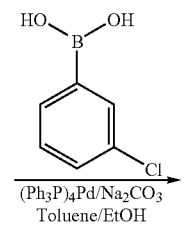

(MR 103). Synthesis of 4-(3-chloro-phenyl)-5-fluoro-6-(6-pyrrolidin-1-yl-pyridin-3-ylmethyl)-benzothiazole hydrochloride (BA-57): To MR 97 (0.13 g, 0.35 mmol) and Pyrrolidine (0.07 g, 1.05 mmol) was added 1,8-diazabicyclo[5.4.0]undec-7-ene (DBU) (0.27 g, 1.74 mmol). The reaction mixture was stirred and heated at 100° C. for 1 h. Cooled to room temperature, diluted with dichloromethane (6 mL), washed with 0.5 N HCl (2×4 mL), dried with Na₂SO₄, filtered, and concentrated. The residue was purified by silica gel column chromatography using 3% methanol in dichloromethane to afford 0.06 g (41%) of foamy solid. The solid was suspended in ether (2 mL), than 2M HCl-ether (0.5 mL, 1.0 mmol) was added, stirred for 1 h, than concentrated, again triturated with ether (2 mL), dried to afford 0.6 g (98%) of BA-57 as off-white solid. 1H NMR (DMSO-d6, 400 MHz): 13.27 (br s, 1 H), 9.44 (s, 1 H), 8.16 (d, J=6.8 Hz, 1 H), 7.85-7.95 (m, 2 H), 7.66 (s, 1 H), 7.51-7.58 (m, 3 H), 7.07 (d, J=9.2 Hz, 1 H), 4.14 (s, 2 H), 3.48-3.56 (m, 4 H), 1.92-2.7 (m, 4 H); MS (APCI+): 424.1 (M+1), LC-MS: 87.4%.

BA-58

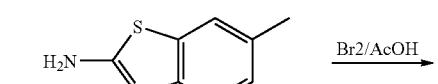

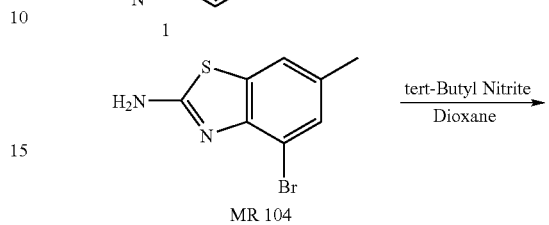

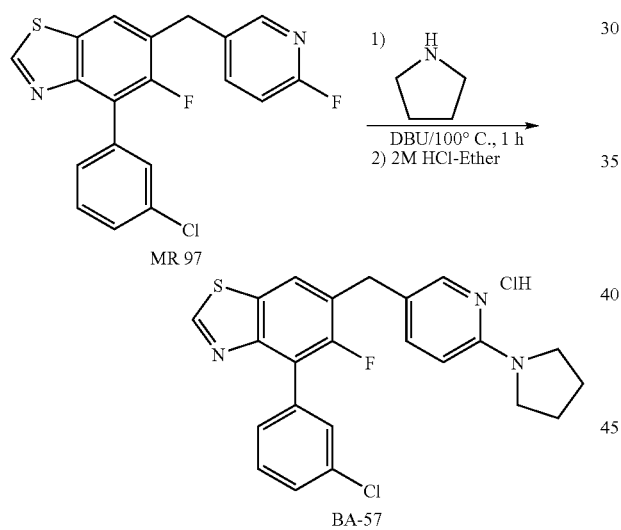

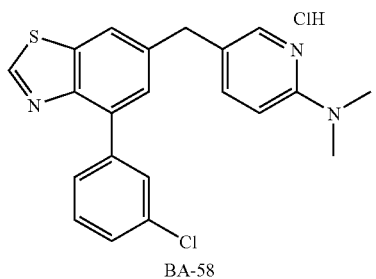

BA-58

(MR 104) Synthesis of 4-bromo-6-methyl-benzothiazol-2-ylamine: To a heated (80° C.) and stirred solution of 6-methyl-benzothiazol-2-ylamine (10.0 g, 60.89 mmol) in acetic acid (210 mL) was added a solution of bromine (19.46 g, 121.78 mmol) in acetic acid (40 mL) over 30 min. The reaction mixture was stirred at 80° C. for 20 h, cooled to room temperature than poured on to crushed ice-water (400 mL). Ammonium hydroxide solution (28%) was added to pH 8, stirred for 2 h. Filtered, washed with water, dried to afford 13.5 g (91%) of MR 104 as brown solid.

(MR 105) Synthesis of 4-bromo-6-methyl-benzothiazole: To MR 104 (13.4 g, 55.11 mmol) in dioxane (150 mL) was added tert-butyl nitrite (6.25 g. 60.63 mmol). The reaction mixture was stirred and heated at 60° C. for 1.0 h, concentrated. The residue was purified by silica gel column chromatography using 1:1 dichloromethane-hexanes to afford 4.45 g (34%) of MR 105 as orange solid.

(MR 106) Synthesis of 4-(3-chloro-phenyl)-6-methyl-benzothiazole: To MR 105 (2.03 g, 8.77 mmol), 3-chlorophenyl-boronic acid (2) (1.51 g, 9.64 mmol) and Pd(Ph$_3$P)$_4$ (0.51 g, 0.44 mmol) was added toluene (80 mL), EtOH (20 mL) and 2M NaCO$_3$ solution (8.8 mL, 17.54 mmol). Ar gas was bubbled through the stirred reaction for 15 min. The reaction was stirred at 80° C. under Ar for 20 h. The reaction was cooled to room temperature, H$_2$O (60 mL) and ethyl acetate (80 mL) were added. The layers were separated and the aqueous was extracted with ethyl acetate (2×40 mL). The combined organic extracts were dried with Na$_2$SO$_4$, filtered, and concentrated. The residue was purified by silica gel column chromatography using 20% ethyl acetate in hexanes to afford 2.23 g (98%) of MR 106 as brown viscous liquid.

(MR 107) Synthesis of 6-bromomethyl-4-(3-chloro-phenyl)-benzothiazole: To MR 106 (2.2 g, 8.47 mmol) and NBS (1.54 g, 8.55 mmol) in CCl$_4$ (50 mL) was added benzoylperoxide (0.1 g, 0.41 mmol). The reaction was stirred at 80° C. under N$_2$ for 18 h. The reaction was cooled to room temperature and concentrated. The residue was triturated with 20% ethyl acetate in hexanes to afford 2.9 g (99%) of MR 107 as a light brown solid.

(MR 108) Synthesis of 4-(4-(3-chloro-phenyl)-6-(6-fluoro-pyridin-3-ylmethyl)-benzothiazole: To MR 107 (2.8 g, 8.27 mmol), 2-fluoro-5-pyridylboronic acid (1.28 g, 9.09 mmol) and Pd(Ph$_3$P)$_4$ (0.48 g, 0.41 mmol) was added toluene (60 mL), EtOH (10 mL) and 2M NaCO$_3$ solution (8.3 mL, 16.54 mmol). Ar gas was bubbled through the stirred reaction for 15 min. The reaction was stirred at 80° C. under Ar for 3 h. The reaction was cooled to room temperature, H$_2$O (60 mL) and ethyl acetate (80 mL) were added. The layers were separated and the aqueous was extracted with ethyl acetate (2×40 mL). The combined organic extracts were dried with Na$_2$SO$_4$, filtered, and concentrated. The residue was purified by silica gel column chromatography using dichloromethane to afford 1.53 g (53%) of MR 108 as light yellow solid.

(MR 109). Synthesis of {5-[4-(3-chloro-phenyl)-benzothiazol-6-ylmethyl]-pyridin-2-yl}-dimethyl-amine hydrochloride (BA-58): To MR 108 (0.15 g, 0.42 mmol) was added 2M solution of dimethylamine in methanol (2.2 mL, 4.4 mmol). Vial was sealed and heated at 150° C. for 1 h. The reaction mixture was concentrated, the residue was purified by silica gel column chromatography using dichloromethane to afford 0.116 g (75%) of gummy solid. The solid was suspended in ether (2 mL), than 2M HCl-ether (0.8 mL, 1.6 mmol) was added, stirred for 1 h, than concentrated, again triturated with ether (2 mL), dried to afford 0.118 g (98%) of BA-58 as white solid. 1H NMR (DMSO-d6, 400 MHz): 13.4 (br s, 1 H), 9.42 (s, 1 H), 8.11 (d, J=1.6 Hz, 1 H), 8.02 (s, 1 H), 7.92-8.0 (m, 2 H), 7.69 (d, J=1.6 Hz, 1 H), 7.48-7.57 (m, 21 H), 7.19 (d, J=9.24 Hz, 1 H), 4.14 (s, 2 H), 3.19 (s, 6 H); MS (APCI+): 380.0 (M+1), LC-MS: 95.7%; HPLC 93.61% pure.

BA-59

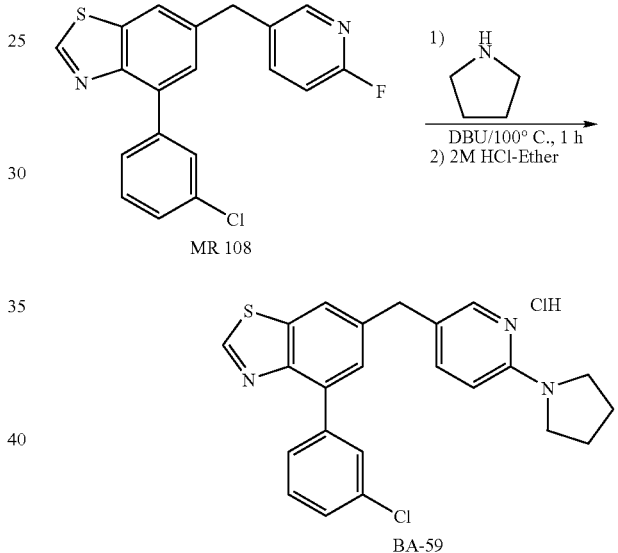

MR 108

BA-59

(MR 110). Synthesis of 4-(3-chloro-phenyl)-6-(6-pyrrolidin-1-yl-pyridin-3-ylmethyl)-benzothiazole hydrochloride (BA-59): To MR 108 (0.15 g, 0.42 mmol) and Pyrrolidine (0.09 g, 1.27 mmol) was added 1,8-diazabicyclo[5.4.0]undec-7-ene (DBU) (0.32 g, 2.11 mmol). The reaction mixture was stirred and heated at 100° C. for 1 h. Cooled to room temperature, diluted with dichloromethane (6 mL), washed with 0.5 N HCl (2×4 mL), dried with Na$_2$SO$_4$, filtered, and concentrated. The residue was purified by silica gel column chromatography using 2% methanol in dichloromethane to afford 0.103 g (60%) of viscous liquid. The viscous liquid (0.09 g, 0.23 mmol) was suspended in ether (2 mL), than 2M HCl-ether (0.5 mL, 1.0 mmol) was added, stirred for 1 h, than concentrated, again triturated with ether (2 mL), dried to afford 0.9 g (94%) of BA-59 as white solid. 1H NMR (DMSO-d6, 400 MHz): 13.25 (br s, 1 H), 9.42 (s, 1 H), 8.1 (d, J=1.6 Hz, 1 H), 8.0 (d, J=1.6 Hz, 1 H), 7.9-7.95 (m, 2 H), 7.81 (dt, J=7.2, 1.6 Hz 1 H), 7.67 (d, J=1.2 Hz), 7.481-7.56 (m, 2 H), 7.0 (d, J=8.4 Hz, 1 H), 4.11 (s, 2 H), 3.4-3.56 (m, 4 H), 1.95-2.17 (m, 4 H); MS (APCI+): 406.1 (M+1), LC-MS: 98.1%.

BA-55

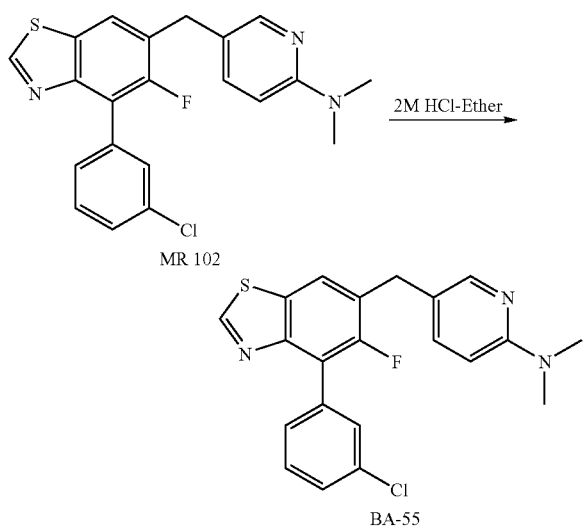

(MR 102). Synthesis of {5-[4-(3-chloro-phenyl)-5-fluoro-benzothiazol-6-ylmethyl]-pyridin-2-yl}-dimethyl-amine hydrochloride (BA-55): To MR 102 (0.1 g, 0.26 mmol) in ether (2 mL), than 2M HCl-ether (1.0 mL, 2.0 mmol) was added, stirred for 1 h, than concentrated, again triturated with ether (2 mL), dried to afford 0.11 g (98%) of BA-55 as white solid. 1H NMR (DMSO-d6, 400 MHz): 9.39 (s, 1 H), 8.11 (d, J=6.8 Hz, 1 H), 8.05 (d, J=2.0 Hz, 1 H), 7.6 (s, 1 H), 7.45-7.59 (m, 3 H), 7.45 (d, J=6.8 Hz, 1 H), 6.63 (d, J=8.8 Hz, 1 H), 4.01 (s, 2 H), 2.99 (s, 6 H); MS (APCI+): 398.1 (M+1), LC-MS: 98.9%; HPLC 98.5% pure.

BA-60

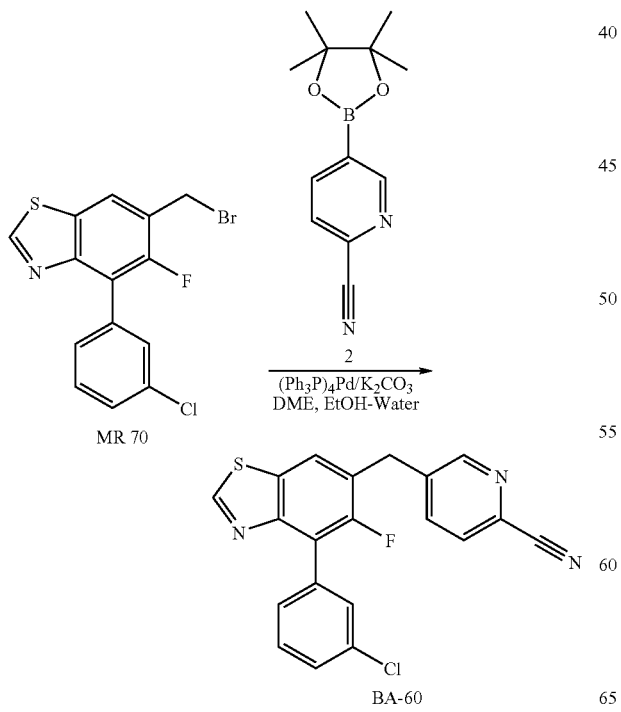

(MR 112). Synthesis of 5-[4-(3-chloro-phenyl)-5-fluoro-benzothiazol-6-ylmethyl]-pyridine-2-carbonitrile (BA-60): To MR 70 (0.8 g, 2.24 mmol), 5-(4,4,5,5-tetramethyl-[1,3,2]dioxaborolan-2-yl)-pyridine-2-carbonitrile (2) (0.57 g, 2.47 mmol) and (PPh₃)₄Pd (0.13 g, 0.11 mmol) was added toluene (30.0 mL), and EtOH (10.0 mL). The reaction mixture stirred for 5 min, than Na2CO3 (2M soln, 2.5 mL, 5.0 mmol) was added. Ar gas was bubbled through the stirred reaction for 15 min. Then the reaction was stirred at 80° C. for 1 h. The reaction was cooled to room temperature, concentrated. The residue was diluted with water (40 mL), extracted with ethyl acetate (2×30 mL), washed with brine (30 mL), dried with Na₂SO₄, filtered, and concentrated. The residue was purified by silica gel column chromatography using dichloromethane to afford 0.62 g (73%) of BA-60 as light brown solid. 1H NMR (DMSO-d6, 400 MHz): 9.43 (s, 1 H), 8.76 (d, J=1.6 Hz, 1 H), 8.21 (d, J=7.2 Hz, 1 H), 7.92-7.81 (m, 2 H), 7.66 (s, 1 H), 7.5-7.59 (m, 3 H), 4.32 (s, 2 H); MS (APCI−): 378.0 (M−1), LC-MS: 100%.

BA-61

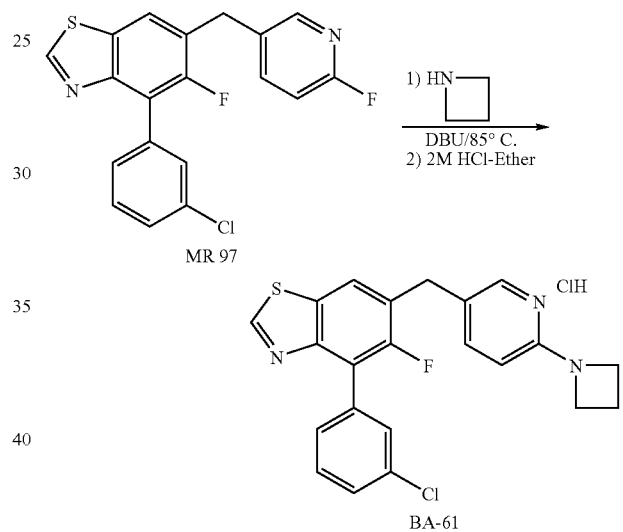

(MR 113) Synthesis of 6-(6-azetidin-1-yl-pyridin-3-ylmethyl)-4-(3-chloro-phenyl)-5-fluoro-benzothiazole hydrochloride (BA-61): To MR 97 (0.15 g, 0.45 mmol) and azetidine (0.07 g, 1.21 mmol) was added 1,8-diazabicyclo[5.4.0]undec-7-ene (DBU) (0.31 g, 2.01 mmol). The reaction mixture was stirred and heated at 85° C. for 15 min. Cooled to room temperature, diluted with dichloromethane (6 mL), washed with 0.5 N HCl (2×4 mL), dried with Na₂SO₄, filtered, and concentrated. The residue was purified by silica gel column chromatography using 5% methanol in dichloromethane followed by preparative thin layer chromatography using 1:1 ethyl acetate in hexanes to afford 0.022 g (13%) of off white solid. The solid was suspended in ether (2 mL), than 2M HCl-ether (0.5 mL, 1.0 mmol) was added, stirred for 1 h, than concentrated, again triturated with ether (2 mL), dried to afford 0.023 g (98%) of BA-61 as off-white solid. 1H NMR (DMSO-d6, 400 MHz): 9.44 (s, 1 H), 8.15 (d, J=7.2 Hz, 1 H), 7.95 (s, 1 H), 7.8-7.9 (m, 1 H), 7.66 (s, 1 H), 7.44-7.59 (m, 3 H), 6.8 (d, J=8.8 Hz, 1 H), 4.18-4.28 (m, 4 H), 4.11 (s, 2 H), 2.38-2.46 (m, 2H); MS (APCI+): 410.0 (M+1), LC-MS: 87%.

BA-63

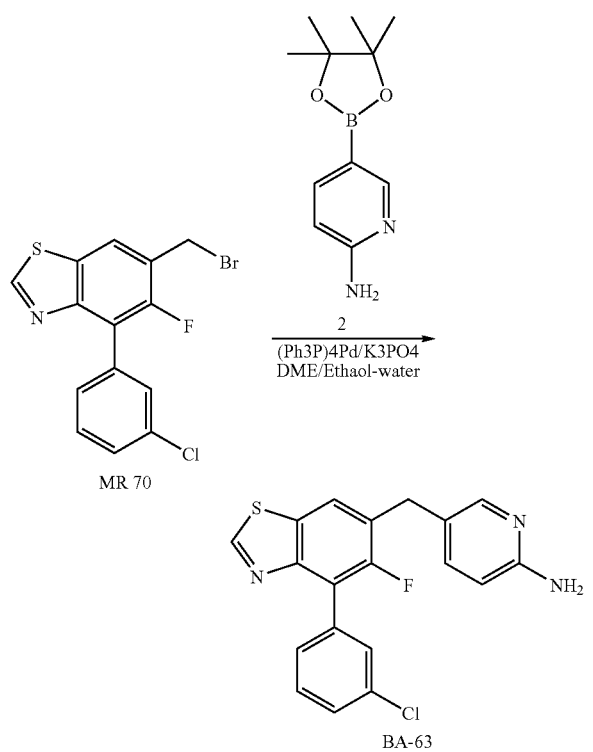

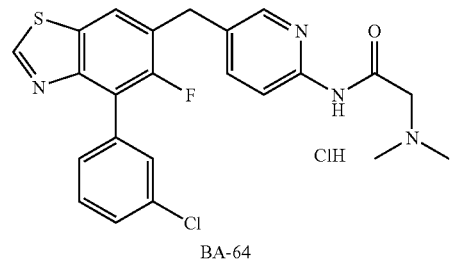

BA-64

(MR 114). Synthesis of N-{5-[4-(3-chloro-phenyl)-5-fluoro-benzothiazol-6-ylmethyl]-pyridin-2-yl}-2-dimethylamino-acetamide hydrochloride (BA-64): To dimethylamino-acetic acid (0.04 g, 0.41 mmol) in dichloromethane (2 mL) was added thionyl chloride (0.1 g, 0.81 mmol). The reaction mixture was stirred for 3 h, concentrated. THF (1 mL) was added under nitrogen atmosphere, than a solution of MR 114 (0.1 g, 0.27 mmol) in THF (1 mL) was added followed by diisopropylethylamine (0.14 g, 1.08 mmol). Stirred for 3 h, than water (4 mL) and ethyl acetate (10 mL) was added. The organic layer was separated and the aqueous layer was again washed with ethyl acetate (5 mL). The combined organic layers were washed with brine (4 mL), dried ($Na_2SO_4$), filtered, concentrated. The residue was purified by preparative thin layer chromatography using 5% methanol in dichloromethane to afford 0.027 g (22%) of off white solid. The solid (0.026 g, 0.06 mmol) was suspended in ether (2 mL), than 2M HCl-ether (0.5 mL, 1.0 mmol) was added, stirred for 1 h, than concentrated, again triturated with ether (2 mL), dried to afford 0.029 g (98%) of BA-64 as off-white solid. 1H NMR (DMSO-d6, 400 MHz): 11.13 (s, 1 H), 9.86 (br s, 1 H), 9.42 (s, 1 H), 8.35 (s, 1 H), 8.2 (d, J=7.2 Hz, 1 H), 7.95-8.05 (m, 1 H), 7.77 (dd, J=8, 2.4 Hz, 1 H), 7.56 (s, 1 H), 7.5-7.59 (m, 3 H), 4.17 (s, 2H), 3.68 (s, 2 H), 2.86 9 s, 6 H); MS (APCI-): 411.2 (M-1), LC-MS: 96%.

(MR 114). Synthesis of 5-[4-(3-chloro-phenyl)-5-fluoro-benzothiazol-6-ylmethyl]-pyridin-2-ylamine (BA-63): To MR 70 (0.81 g, 2.27 mmol), 2-amino-5-pyridineboronic acid pinacol ester (2) (0.56 g, 2.5 mmol) and $(PPh_3)_4Pd$ (0.13 g, 0.11 mmol) and $K_3PO_4$ (0.96 g, 4.54 mmol) was added DME (20.0 mL), and EtOH—$H_2O$ (1:1, 10.0 mL). Ar gas was bubbled through the stirred reaction for 5 min. The reaction was stirred and heated at 80° C. for 4 h. The reaction was cooled to room temperature, concentrated. Diluted with dichloromethane (60 mL), washed with water (2×50 mL), brine (30 mL), dried ($Na_2SO_4$), filtered, concentrated. The residue was purified by silica gel column chromatography using 5% methanol in dichloromethane to afford 0.31 g (37%) of BA-63 as light brown solid. 1H NMR (DMSO-d6, 400 MHz): 9.39 (s, 1 H), 8.1 (d, J=6.8 Hz, 1 H), 7.87 (d, J=2.0 Hz, 1 H), 7.66 (s, 1 H), 7.5-7.59 (m, 3 H), 7.28 (dd, J=8.0, 2.4 Hz, 1 H), 6.39 (d, J=8.4 Hz, 1H), 5.78 (s, 2 H), 3.95 (s, 2H); MS (APCI+): 370.2 (M+1), LC-MS: 98%.

BA-64

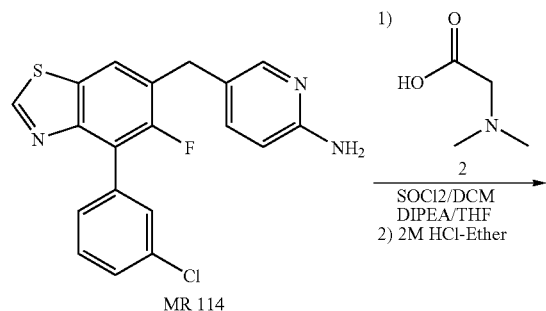

BA-66

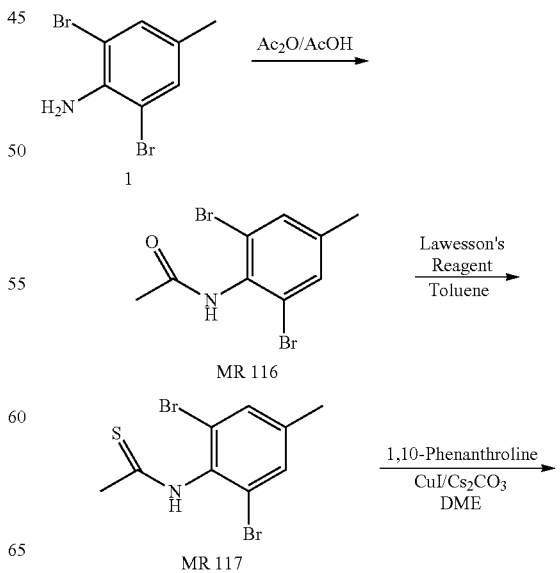

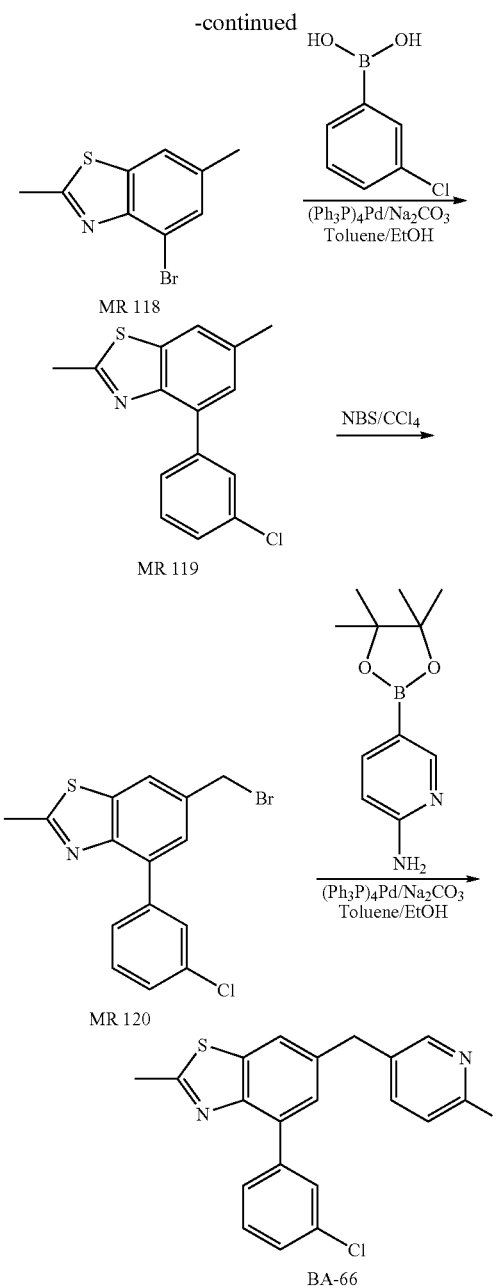

(MR 116) Synthesis of N-(2,6-dibromo-4-methyl-phenyl)-acetamide: To 2,6-dibromo-4-methyl-phenylamine (10.0 g, 37.74 mmol) in acetic acid (20 mL) was added acetic anhydride (5.0 g, 48.98 mmol). The reaction mixture was stirred and heated at 90° C. for 30 min, cooled to room temperature than poured on to crushed ice-water (300 mL). The white solid was filtered, washed with water, dried to afford 12.0 g (99%) of MR 116 as white solid.

(MR 117) Synthesis of N-(2,6-dibromo-4-methyl-phenyl)-thioacetamide: To MR 116 (1.0 g, 3.26 mmol) in toluene (20 mL) was added Lawesson's Reagent (0.66 g. 1.63 mmol). The reaction mixture was stirred and heated at reflux for 2.5 h, concentrated. The residue was purified by silica gel column chromatography using 1:1 dichloromethane-hexanes to afford 0.98 g (93%) of MR 117 as white solid.

(MR 118) Synthesis of 4-bromo-2,6-dimethyl-benzothiazole: To MR 117 (0.63 g, 1.93 mmol) in DME (8 mL) was added Copper(I)iodide (0.02 g. 0.1 mmol), 1,10-phenanthroline (0.04 g, 0.2 mmol) and cesium carbonate (0.95 g, 2.9 mmol). The reaction mixture was stirred and heated at 85° C. for 20 h, filtered over Celite, concentrated. The residue was purified by silica gel column chromatography using dichloromethane to afford 0.41 g (87%) of MR 118 as light yellow viscous liquid.

(MR 119) Synthesis of 4-(3-chloro-phenyl)-2,6-dimethyl-benzothiazole: To MR 118 (0.65 g, 2.68 mmol), 3-chlorophenylboronic acid (2) (0.46 g, 2.954 mmol) and Pd(Ph$_3$P)$_4$ (0.16 g, 0.13 mmol) was added toluene (40 mL), EtOH (10 mL) and 2M NaCO$_3$ solution (2.7 mL, 5.4 mmol). Ar gas was bubbled through the stirred reaction for 15 min. The reaction was stirred at 85° C. under Ar for 3 h. The reaction was cooled to room temperature, H$_2$O (60 mL) and ethyl acetate (80 mL) were added. The layers were separated and the aqueous was extracted with ethyl acetate (2×40 mL). The combined organic extracts were dried with Na$_2$SO$_4$, filtered, and concentrated. The residue was purified by silica gel column chromatography using 1:1 dichloromethane in hexanes to afford 0.7 g (98%) of MR 119 as viscous liquid.

(MR 120) Synthesis of 6-bromomethyl-4-(3-chloro-phenyl)-2-methyl-benzothiazole: To MR 119 (0.3 g, 1.1 mmol) and NBS (0.2 g, 1.1 mmol) in CCl$_4$ (30 mL) was added benzoylperoxide (0.02 g, 0.08 mmol). The reaction was stirred at 80° C. under N$_2$ for 1 h. The reaction was cooled to room temperature and concentrated. The residue was triturated with 1:1 dichloromethane in hexanes, concentrated to afford 0.4 g (98%) of MR 120 as a light brown solid.

(MR 121). Synthesis of 5-[4-(3-chloro-phenyl)-2-methyl-benzothiazol-6-ylmethyl]-pyridin-2-ylamine (BA-66): To MR 120 (0.4 g, 1.1 mmol), 2-amino-5-pyridineboronic acid pinacol ester (2) (0.19 g, 1.2 mmol) and (PPh$_3$)$_4$Pd (0.06 g, 0.05 mmol) and Na$_2$CO$_3$ solution (2M, 1.1 mL, 2.2 mmol) was added toluene (40.0 mL), and EtOH (10.0 mL). Ar gas was bubbled through the stirred reaction for 15 min. The reaction was stirred and heated at 80° C. for 3 h. The reaction was cooled to room temperature, H$_2$O (50 mL) and ethyl acetate (50 mL) were added. The layers were separated and the aqueous was extracted with ethyl acetate (2×40 mL). The combined organic extracts were dried with Na$_2$SO$_4$, filtered, and concentrated. The residue was purified by silica gel column chromatography using 5% methanol in dichloromethane than by preparative thin layer chromatography using 5% methanol in dichloromethane to afford 0.26 g (63%), of BA-66 as light yellow gummy liquid. 1H NMR (CDCl$_3$, 400 MHz): 8.0 (d, J=2.0 Hz, 1 H), 7.78-7.8 (m, 1 H), 7.66-7.7 (m, 1 H), 7.58 (d, J=2.0 Hz, 1 H), 7.25-7.41 (m, 4 H), 6.46 (d, J=8.4 Hz, 1 H), 4.4 (s, 2 H), 3.98 (s, 2H), 2.82 (s, 3 H); MS (APCI+): 366.1 (M+1), LC-MS: 96.5%.

BA-67

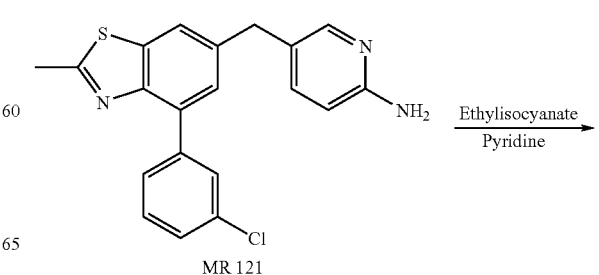

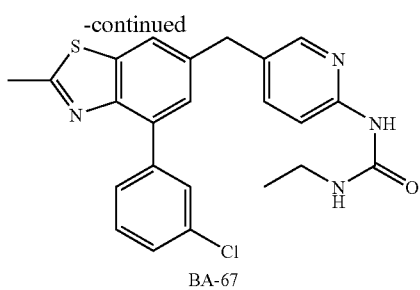

BA-67

(MR 122). Synthesis of 1-{5-[4-(3-chloro-phenyl)-2-methyl-benzothiazol-6-ylmethyl]-pyridin-2-yl}-3-ethyl-urea (BA-67): To MR 121 (0.25 g, 0.68 mmol) in pyridine (2.5 mL) was added ethylisocyanate (0.15 g, 2.05 mmol). The reaction mixture was stirred at room temperature for 72 h, concentrated. Water (10 mL) was added, stirred for 0.5 h, filtered, washed with water (5 mL), than ether (10 mL), dried. Again recrystallized from hot ethyl acetate to afford 0.083 g (28%) of BA-67 as light yellow crystalline solid. 1H NMR (DMSO-d6, 400 MHz): 9.08 (s, 1 H), 8.16 (d, J=2.0 Hz, 1 H), 8.06-8.12 (br s, 1 H), 7.91 (d, J=1.6 Hz, 1 H), 7.87 (t, J=2.4 Hz, 1 H), 7.74-7.78 (m, 1 H), 7.62 (dd, J=8.8, 2.4 Hz, 1 H), 7.44-7.54 (m, 3 H), 7.25 (d, J=8.8 Hz, 1 H), 4.04 (s, 2 H), 3.12-3.4 (m, 2 H), 2.78 (s, 3 H), 1.07 (t, J=7.2 Hz, 1 H); MS (APCI+): 437.1 (M+1), LC-MS: 100%; HPLC 98.7% pure.

BB-04

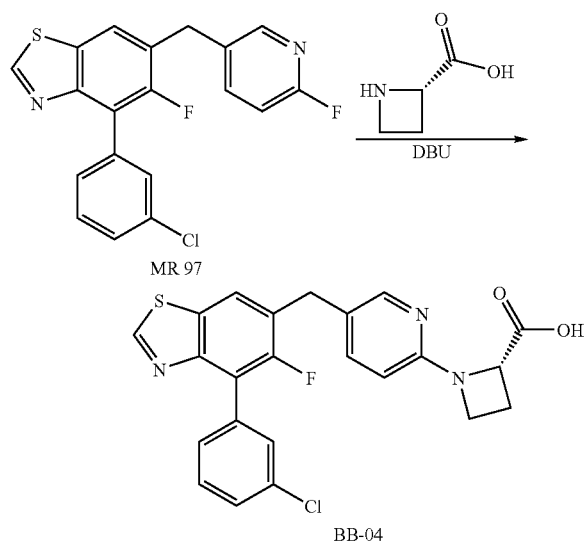

MR 97

BB-04

(MR 124) Synthesis of (S)-1-{5-[4-(3-chloro-phenyl)-5-fluoro-benzothiazol-6-ylmethyl]-pyridin-2-yl}-azetidine-2-carboxylic acid (BB-04): To MR 97 (0.3 g, 0.8 mmol) and L-azetidine-2-carboxylic acid (2) (0.16 g, 1.61 mmol) was added 1,8-diazabicyclo[5.4.0]undec-7-ene (DBU) (0.61 g, 4.02 mmol). The reaction mixture was stirred and heated at 150° C. for 30 min. Cooled to room temperature, diluted with dichloromethane (8 mL), washed with 0.5 N HCl (2×4 mL), dried with Na$_2$SO$_4$, filtered, and concentrated. The residue was purified by silica gel column chromatography using 5% methanol in dichloromethane to afford 0.057 g (16%) of BB-04 as light yellow solid. 1H NMR (DMSO-d6, 400 MHz): 9.4 (s, 1 H), 8.13 (d, J=6.8 Hz, 1 H), 8.05 (d, J=2.0 Hz, 1 H), 7.66 (s, 1 H), 7.5-7.59 (m, 4 H), 6.47 (d, J=8.0 Hz, 1 H), 4.6-4.7 (m, 1 H), 4.04 (s, 2 H), 3.8-3.96 (m, 2 H), 2.3-2.6 (m, 2 H); MS (APCI+): 454.0 (M+1), LC-MS: 100%.

BB-05

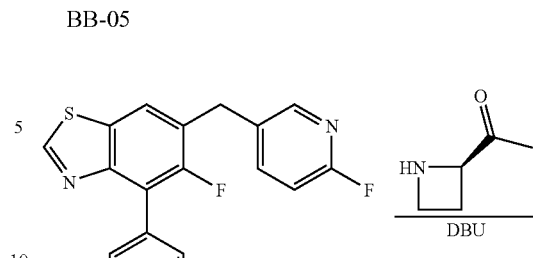

MR 97

BB-05

(MR 125) Synthesis of (R)-1-{5-[4-(3-chloro-phenyl)-5-fluoro-benzothiazol-6-ylmethyl]-pyridin-2-yl}-azetidine-2-carboxylic acid (BB-05): To MR 97 (0.3 g, 0.8 mmol) and D-azetidine-2-carboxylic acid (2) (0.16 g, 1.61 mmol) was added 1,8-diazabicyclo[5.4.0]undec-7-ene (DBU) (0.61 g, 4.02 mmol). The reaction mixture was stirred and heated at 100° C. for 30 min. Cooled to room temperature, diluted with dichloromethane (8 mL), washed with 0.5 N HCl (2×4 mL), dried with Na$_2$SO$_4$, filtered, and concentrated. The residue was purified by silica gel column chromatography using 5% methanol in dichloromethane to afford 0.074 g (20%) of BB-05 as off-white solid. 1H NMR (DMSO-d6, 400 MHz): 12.98 (s, 1 H), 9.4 (s, 1 H), 8.12 (d, J=7.2 Hz, 1 H), 8.05 (d, J=2.4 Hz, 1 H), 7.66 (s, 1 H), 7.46-7.58 (m; 4 H), 6.41 (d, J=8.8 Hz, 1 H), 4.52-4.63 (m, 1 H), H), 4.03 (s, 2 H), 3.75-3.85 (m, 2 H), 2.3-2.58 (m, 2 H); MS (APCI+): 454.0 (M+1), LC-MS: 100%; HPLC 97.5% pure.

BA-74

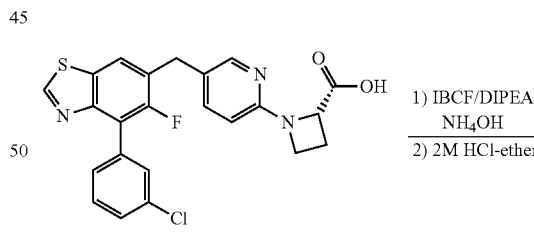

MR 124

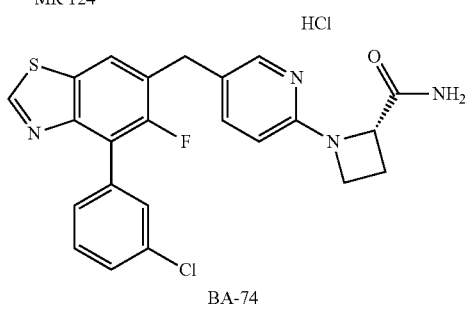

BA-74

(MR 126). Synthesis of (S)-1-{5-[4-(3-chloro-phenyl)-5-fluoro-benzothiazol-6-ylmethyl]-pyridin-2-yl}-azetidine-2-carboxylic acid amide hydrochloride (BA-74): To a cooled 0° C. and stirred solution of MR 124 (0.28 g, 0.62 mmol) in THF (4 mL) was added diisopropylethylamine (0.16 g, 1.23 mmol). The reaction mixture was stirred for 5 min, than isobutylchloroformate (0.1 g, 0.74 mmol) was added, stirred at 0° C. for 30 min. Ammonium hydroxide (28%, 2.0 mL) was added, warmed to room temperature, stirred for 18 h. The organic layer was separated, the aqueous layer was washed with ether (6 mL). The combined organic layers were dried with Na$_2$SO$_4$, filtered, and concentrated. The residue was purified by silica gel column chromatography using 5% methanol in dichloromethane than preparative thin layer chromatography using 5% methanol in dichloromethane to afford 0.059 g of white solid. The solid was suspended in ether (2.0 mL) was added 2M HCl in ether (0.5 mL, 1.0 mmol). The reaction mixture was stirred for 2 h at room temperature, concentrate under N$_2$ flow, than dried under vacuum to afford 0.06 g (21%) of BA-74 as white solid. 1H NMR (DMSO-d6, 400 MHz): 9.43 (s, 1 H), 8.16 (d, J=7.2 Hz, 1 H), 8.01 (d, J=2.0 Hz, 1 H), 7.85 (br s, 1 H), 7.66 (s, 1 H), 7.5-7.58 (m, 4 H), 7.36 (br s, 1 H), 6.7 (br s, 1 H), 4.82 (br s, 1 H), 4.11 (s, 2 H), 3.89-4.05 (m, 2 H), 2.3-2.58 (m, 2 H); MS (APCI+): 453.0 (M+1), LC-MS: 99.50%; HPLC 98.7% pure. BA-75 mL, 2.0 mmol). The reaction mixture was stirred for 1 h at room temperature, concentrate under N$_2$ flow, than dried under vacuum to afford 0.18 g (36%) of BA-75 as white solid. 1H NMR (DMSO-d6, 400 MHz): 9.43 (s, 1 H), 8.16 (d, J=7.2 Hz, 1 H), 8.01 (d, J=2.0 Hz, 1 H), 7.85 (br s, 1 H), 7.7 (s, 1 H), 7.66 (s, 1 H), 7.5-7.58 (m, 3 H), 7.38 (br s, 1 H), 6.7 (br s, 1 H), 4.86 (br s, 1 H), 4.121 (s, 2 H), 4.0-4.25 (m, 2 H), 2.6-2.75 (m, 1 H), 2.25-2.38 (m, 12 H); MS (APCI+): 453.0 (M+1), LC-MS: 97.8%; HPLC 97.4% pure.

BB-08

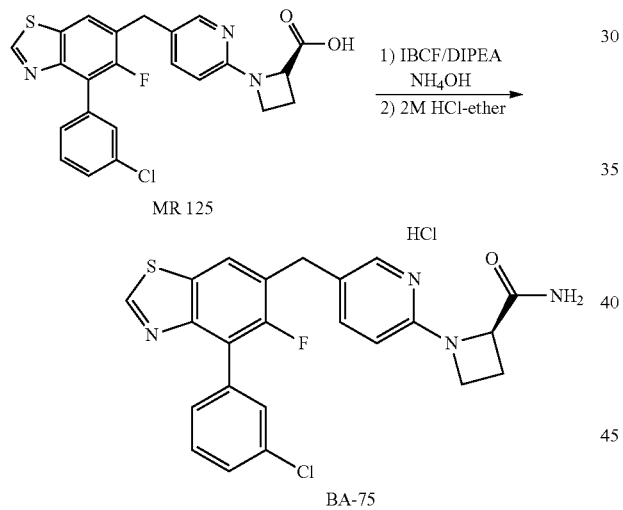

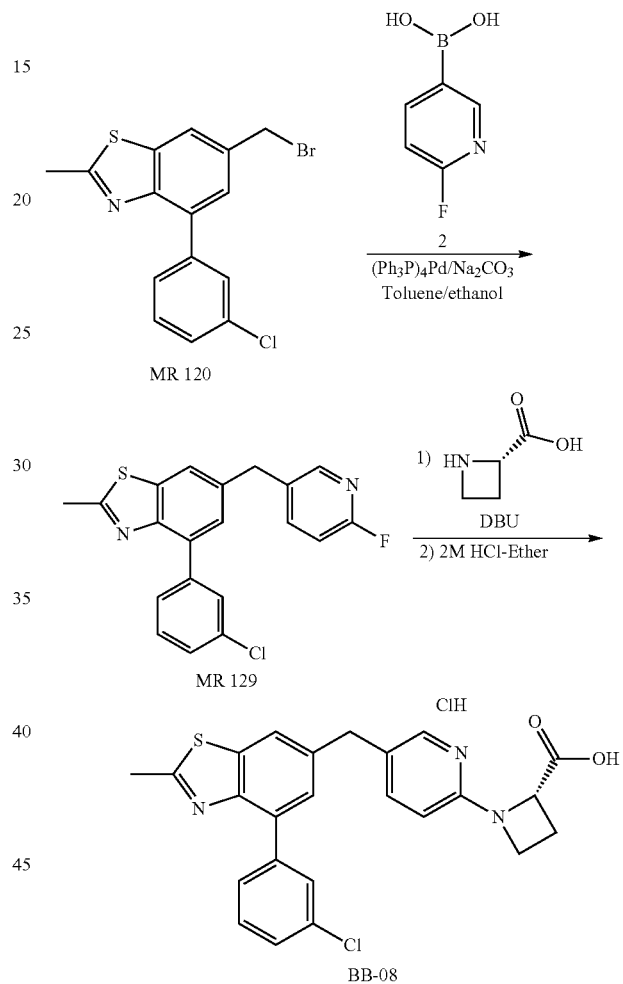

(MR 128). Synthesis of (R)-1-{5-[4-(3-chloro-phenyl)-5-fluoro-benzothiazol-6-ylmethyl]-pyridin-2-yl}-azetidine-2-carboxylic acid amide hydrochloride (BA-75): To a cooled 0° C. and stirred solution of MR 125 (0.5 g, 1.1 mmol) in THF (10 mL) was added diisopropylethylamine (0.28 g, 2.2 mmol). The reaction mixture was stirred for 5 min, than isobutylchloroformate (0.18 g, 1.3 mmol) was added, stirred at 0° C. for 45 min. Ammonium hydroxide (28%, 4.0 mL) was added, warmed to room temperature, stirred for 1.5 h. The reaction mixture was diluted with water (5 mL). The organic layer was separated, the aqueous layer was washed with ethyl acetate (2×20 mL). The combined organic layers were dried with Na$_2$SO$_4$, filtered, and concentrated. The residue was purified by silica gel column chromatography using 1:1 ethyl acetate in hexanes to pure ethyl acetate than preparative thin layer chromatography using 5% methanol in dichloromethane to afford 0.17 g of white solid. The solid was suspended in ether (3.0 mL) was added 2M HCl in ether (1.0

(MR 129) Synthesis of 4-(3-chloro-phenyl)-6-(6-fluoro-pyridin-3-ylmethyl)-2-methyl-benzothiazole: Prepared according to the procedure described in Scheme 17.

(MR 130). Synthesis of (S)-1-{5-[4-(3-chloro-phenyl)-2-methyl-benzothiazol-6-ylmethyl]-pyridin-2-yl}-azetidine-2-carboxylic acid hydrochloride (BB-08): To MR 129 (0.28 g, 0.76 mmol) and L-azetidine-2-carboxylic acid (2) (0.15 g, 1.52 mmol) was added 1,8-diazabicyclo[5.4.0]undec-7-ene (DBU) (0.58 g, 3.8 mmol). The reaction mixture was stirred and heated at 150° C. for 15 min. Cooled to room temperature, diluted with dichloromethane (8 mL), washed with 0.5 N HCl (2×4 mL), dried with Na$_2$SO$_4$, filtered, and concentrated. The residue was purified by silica gel column chromatography using 5% methanol in dichloromethane to afford 0.22 g of white solid. The solid was suspended in ether (4.0 mL) was added 2M HCl in ether (1.8 mL, 3.6 mmol). The reaction mixture was stirred for 1 h at room temperature, concentrate under N₂ flow, than dried under vacuum to afford 0.22 g (64%) of BB-08 as white solid. 1H NMR (DMSO-d6, 400 MHz): 8.08 (d, J=1.6 Hz, 1 H), 7.94 (d, J=1.6 Hz, 1 H), 7.87 (t, J=2.0 Hz, 1 H), 7.82 (br s, 1 H), 7.75-7.79 (m, 1 H), 7.46-7.58 (m 4 H), 6.76 (br s, 1 H), 4.86-5.07 (m, 1 H), 4.05 (s, 2 H), 3.98-4.2 (m, 2 H), 2.79 (s, 3 H), 2.65-2.75 (m, 1 H), 2.36-2.45 (m, 1 H); MS (APCI+): 450.0 (M+1), LC-MS: 98.3%.

BB-09

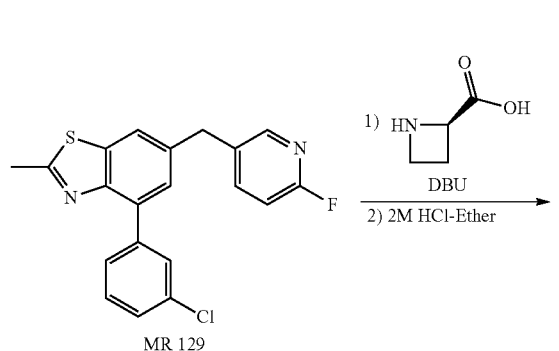

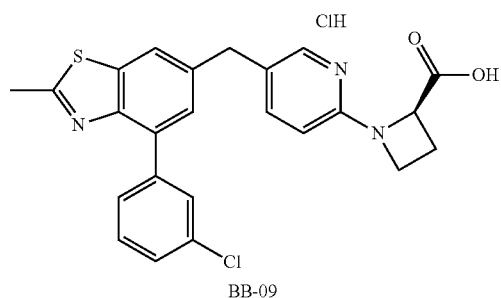

Synthesis of (R)-1-{5-[4-(3-chloro-phenyl)-2-methyl-benzothiazol-6-ylmethyl]-pyridin-2-yl}-azetidine-2-carboxylic acid hydrochloride (BB-09): To MR 129 (0.37 g, 1.0 mmol) and D-azetidine-2-carboxylic acid (2) (0.2 g, 2.01 mmol) was added 1,8-diazabicyclo[5.4.0]undec-7-ene (DBU) (0.76 g, 5.02 mmol). The reaction mixture was stirred and heated at 150° C. for 15 min. Cooled to room temperature, diluted with dichloromethane (8 mL), washed with 0.5 N HCl (2×4 mL), dried with Na₂SO₄, filtered, and concentrated. The residue was purified by silica gel column chromatography using 3% methanol in dichloromethane to afford 0.214 g of white solid. The solid was suspended in ether (4.0 mL) was added 2M HCl in ether (1.8 mL, 3.6 mmol). The reaction mixture was stirred for 1 h at room temperature, concentrate under N₂ flow, than dried under vacuum to afford 0.21 g (47%) of BB-09 as white solid 1H NMR (DMSO-d6, 400 MHz): 8.08 (d, J=1.6 Hz, 1 H), 7.94 (d, J=1.6 Hz, 1 H), 7.87 (t, J=2.0 Hz, 1 H), 7.83 (br s, 1 H), 7.75-7.79 (m, 1 H), 7.46-7.58 (m 4 H), 6.77 (br s, 1 H), 4.86-5.07 (m, 1 H), 4.05 (s, 2 H), 3.9-4.25 (m, 2 H), 2.79 (s, 3 H), 2.65-2.75 (m, 1 H), 2.36-2.45 (m, 1 H); MS (APCI+): 450.0 (M+1), LC-MS: 98.3%.

BB-06

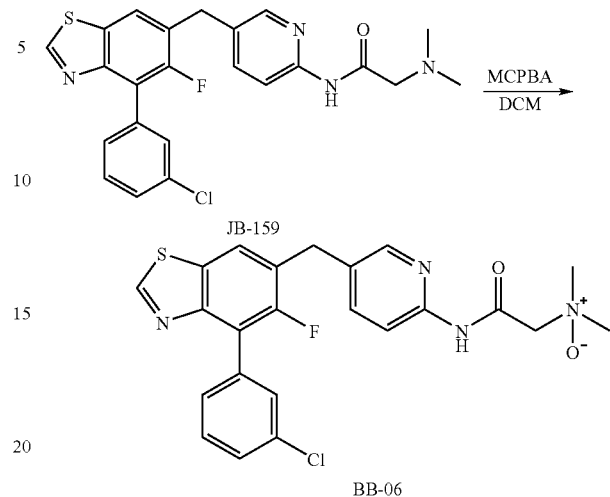

(JB-159)—previously synthesized by Munagala Rao (see experimental). Note—I have a higher yielding procedure which involves synthesizing the entire right hand portion as the boronic ester and then performing the Pd coupling as the final step.

(JB-160). Synthesis of the N-oxide of N-{5-[4-(3-chloro-phenyl)-5-fluoro-benzothiazol-6-ylmethyl]-pyridin-2-yl}-2-dimethylamino-acetamide (BB-06): In an 8 mL vial equipped with a stir bar was placed JB-159 (50 mg, 0.110 mmol) and dichloromethane (1.1 mL). The solution was cooled to 0° C. and then 3-chloroperbenzoic acid (77% max) (12.3 mg, 0.0550 mmol) was added and the solution was warmed to room temperature for 2 hours. The reaction was quenched with 5% aqueous potassium carbonate (3 mL) and the layers were separated. The aqueous portion was extracted with dichlormethane (4 mL) and the organic portions were combined, washed with brine (4 mL), dried (MgSO₄) and concentrated. The crude material was purified by preparative TLC (20×20 cm, 1500 microns) using 10% methanol/DCM as the eluent to produce 10 mg of BB-06 as a yellow solid in 19% yield. ¹H NMR (400 MHz, DMSO-d₆) δ 3.17 (s, 6 H), 4.02 (s, 2 H), 4.15 (s, 2 H), 7.52-7.58 (m, 4 H), 7.67 (s, 1 H), 7.70 (dd, J=9.4 Hz, 1 H), 8.01 (d, J=9 Hz, 1 H), 8.17 (d, J=7 Hz, 1 H), 8.29 (d, J=2 Hz, 1 H), 9.41 (s, 1 H). MS (APCI+): 471.0 (M+1) LC/MS: 95%

BA-73

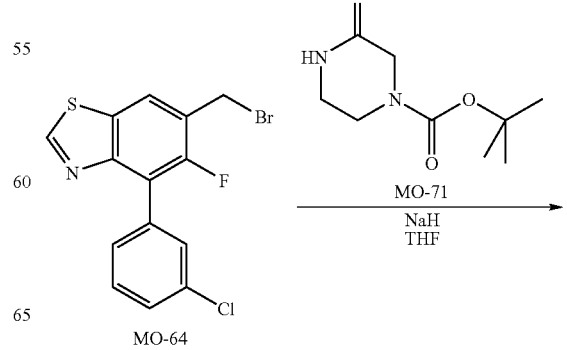

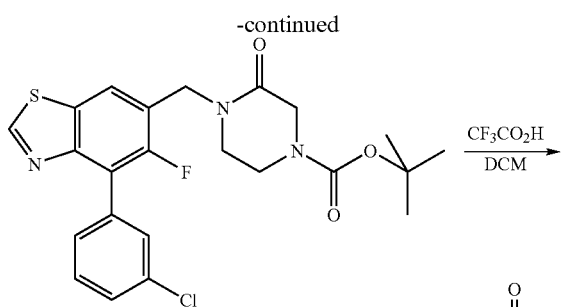

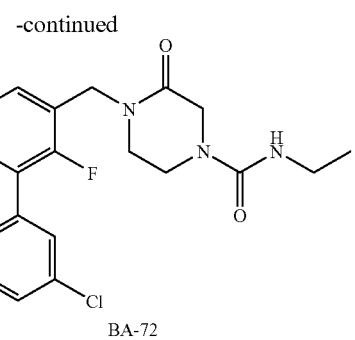

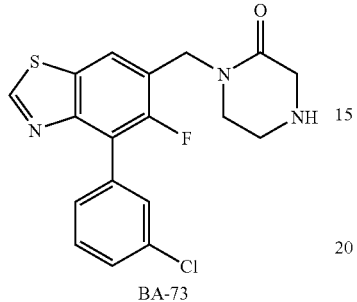

Synthesis of BOC-protected intermediate: To a suspension of sodium hydride (1.8 mmol, 1.2 eq) in 2 mL of tetrahydrofuran at 0-5° C. was added a suspension of MO-64 (1.57 mmol, 1.05 eq), and MO-71 (1.50 mmol, 1.0 eq). The resultant solution was stirred at 0-5° C. for 20 minutes, and them ambient temperature for 4 hours. The reaction was diluted with 10 mL of 15% ammonium chloride, and the aqueous portion extracted with 2 portions of ethyl acetate. The combined organics were washed with successive portions of water and brine, dried over magnesium sulfate, filtered and concentrated to afford the BOC protected intermediate in 82% yield. $^1$HNMR, CDCl$_3$; 400 MHz): 1.46 (s, 9H), 3.46 (dd, J=5.6, 5.2 Hz, 2H), 3.66 (dd, J=5.6, 5.2 Hz, 2H), 4.17 (s, 2H), 4.84 (s, 2H), 7.41-7.48 (M, 2H), 7.54-7.57 (M, 1H), 7.66 (d, J=1.2 Hz, 1H), 8.01 (d, J=6.4 Hz, 1H)

Synthesis of 1-[4-(3-Chloro-phenyl)-5-fluoro-benzothiazol-6-ylmethyl]-piperazin-2-one (BA-73): BOC-protected intermediate (1.24 mmol) was stirred with excess trifluoroacetic acid in dichloromethane at ambient temperature for 2.5 hours. The reaction was concentrated, the residue taken into ethyl acetate, and washed with saturated sodium bicarbonate until the pH of the aqueous was 8-9. The combined organics were washed with successive portions of water and brine, dried over magnesium sulfate, filtered and concentrated to afford the title compound as an oil in 63% yield. $^1$HNMR, DMSO-d$_6$; 400 MHz): 3.11 (dd, J=5.6, 5.2 Hz, 2H), 3.43 (dd, J=5.6, 5.2 Hz, 2H), 3.63 (s, 2H), 4.83 (s, 2H), 7.41-7.48 (M, 2H), 7.56 (m, 1H), 7.66 (d, J=1.6 Hz, 1H), 7.17 (d, J=6.4 Hz, 1H), 9.03 (s, 1H) LC/MS (84.4%) APCI$^+$-found: 376.0 calc'd: 375.9 m/z

BA-72

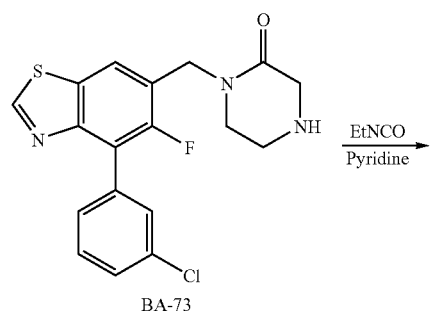

Synthesis of 4-[4-(3-Chloro-phenyl)-5-fluoro-benzothiazol-6-ylmethyl]-3-oxo-piperazine-1-carboxylic acid ethylamide (BA-72): To a solution of BA-73 (0.19 mmol, 1 eq) in 0.7 mL of pyridine at ambient temperature was added ethyl isocyanate (0.58 mmol, 3 eq), and the resulting mixture stirred for 18 hours at ambient temperature. The reaction was poured into water (10 mL), the solids filtered and washed with 2 portions of water and dried in vacuo over ethyl acetate vapors to afford the title compound BA-72 as a solid in 50% yield. $^1$HNMR, DMSO-d$_6$; 400 MHz): 1.01 (t, J=7.2 Hz, 3H), 3.06 (dd, J=6.4 Hz, 2H), 3.38 (dd, J=5.6 Hz, 2H), 3.6 (t, J=5.6, 5.2 Hz, 2H), 4.03 (s, 2H), 4.75 (s, 2H), 6.62 (dd, J=5.6, 5.2 Hz, 1H), 7.52-7.60 (M, 3H), 7.69 (s, 1H), 8.12 (d, J=7.2 Hz, 1H), 9.44 (s, 1H). LC/MS (87.8%): APCI$^+$ found: 447.1 calc'd: 446.9 m/z

BA-71

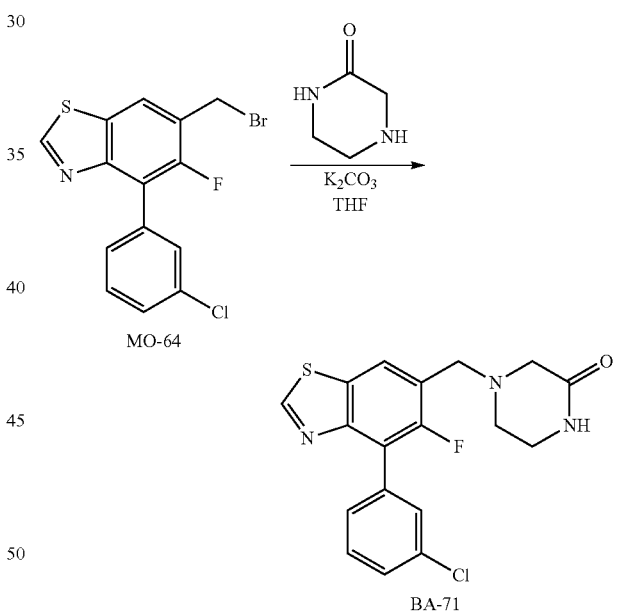

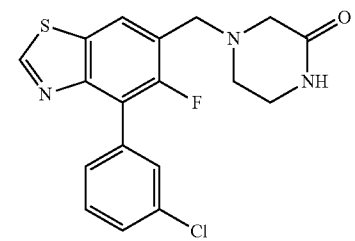

Synthesis of 4-[4-(3-Chloro-phenyl)-5-fluoro-benzothiazol-6-ylmethyl]-piperazin-2-one (BA-71): A mixture of MO-64 (0.32 mmol, 1.0 eq), potassium carbonate (1.8 mmol, 5.6 eq) and 2-oxo-piperazine (0.96 mmol, 3 eq) in 2 mL of tetrahydrofuran was stirred at ambient temperature for 4 hours. The reaction mixture was diluted with 50 mL of water, and Stirred for 20 minutes. The solids were collected by filtration, washed with 2 portions of water, 2 portions of hexanes, and dried in vacuo at 35-40° C. for 18 hours to afford the title compound BA-71 as a solid in 62% yield. $^1$HNMR, DMSO-d$_6$; 400 MHz): 2.80 (dd, J=5.6, 5.2 Hz, 2H), 3.40-3.44 (M, 2H), 3.85 (d, 0.8 Hz, 2H), 5.95 (s, 1H), 7.41-7.47 (M, 2H), 7.56 (dd, J=7.2, 1.6 Hz, 1H), 7.67 (d, J=1.2 Hz, 1H), 8.00 (d, J=6.4 Hz, 1H), 9.04 (s, 1H). LC/MS (92.8%): APCI+ found: 376.0 calc'd: 375.9 m/z

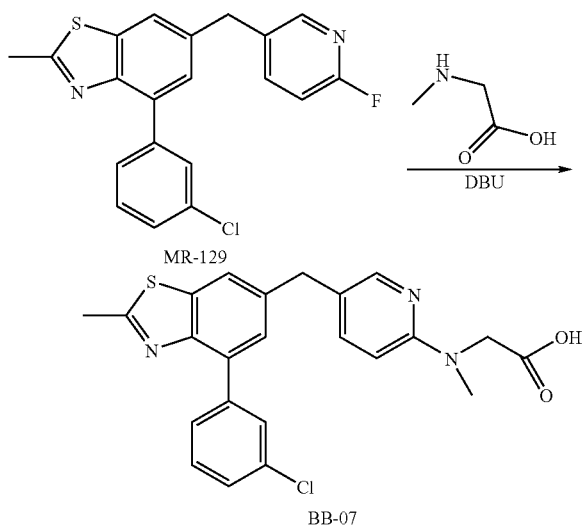

Synthesis of ({5-[4-(3-Chloro-phenyl)-2-methyl-benzothiazol-6-ylmethyl]-pyridin-2-yl}-methyl-amino)-acetic acid (BB-07): To MR 129 (0.23 g, 0.62 mmol) and methylamino-acetic acid (2) (0.11 g, 1.24 mmol) was added 1,8-diazabicyclo[5.4.0]undec-7-ene (DBU) (0.44 ml 5 eq.). The reaction mixture was stirred and heated at 150° C. for 20 min. Cooled to room temperature, diluted with dichloromethane (8 mL), washed with 0.1 N HCl (2×4 mL), dried with $Na_2SO_4$, filtered, and concentrated. The residue was purified by silica gel preparative plate using 7.5% methanol in dichloromethane to afford BB-07 (0.16 g) as a sticky solid. This was triturated with 25% ether/heptane (4.0 mL) to afford 100 mg product. 1H NMR ($CDCl_3$, 400 MHz): 7.99 (s, 1H), 7.78 (t, J=4 Hz, 1 H), 7.68 (dd, J=8, 1.6 Hz, 1 H), 7.58 (s, 1 H), 7.46 (dd, J=8.8, 2 Hz, 1 H), 7.42-7.34 (m, 2 H), 7.28 (s, 1 H), 6.65 (d, J=8.8 Hz, zH1 H), 4.15 (bs, 2 H), 4.02 (s, 2H), 3.125 (s, 3 H), 2.82 (s, 3H); MS (APCI+): 438 (M+1), LC-MS: 98%.

| CmpdNo | NMR |
| --- | --- |
| BA-01 | 1H NMR (CHLOROFORM-d, 400 MHz): d = 8.67 (s, 2H), 7.57-7.62 (m, 2H), 7.41 (d, J = 1.6 Hz, 2H), 7.26 (s, 6H), 7.24 (d, J = 1.7 Hz, 2H), 7.17 (s, 4H), 7.00 (t, J = 8.7 Hz, 4H), 5.18 (s, 3H), 4.06 (s, 4H), 1.56 ppm (s, 22H) |
| BA-02 | 1H NMR (DMSO-d6, 400 MHz): d = 9.30 (s, 1H), 8.64 (t, J = 2.0 Hz, 1H), 8.27 (d, J = 8 Hz, 1H), 8.22 (dd, J = 8.4, 1.6 Hz, 1H), 7.86 (brs, 3H), 7.76 (t, J = 8.0 Hz, 1H), 7.69 (brs, 1H), 7.64 (s, 1H), 5.48 ppm (s, 2H) |
| BA-03 | 1H NMR (CHLOROFORM-d, 400 MHz): d = 8.13 (s, 3H), 7.83-7.94 (m, 6H), 7.45 (d, J = 1.2 Hz, 3H), 7.28 (d, J = 1.3 Hz, 3H), 7.26 (s, 3H), 7.19 (dd, J = 8.4, 5.4 Hz, 6H), 6.95-7.06 (m, 6H), 5.22 (s, 6H), 4.06 (s, 6H), 1.58(s, 6H), 1.26 ppm (s, 2H) |
| BA-04 | 1H NMR (CHLOROFORM-d, 400 MHz): d = 7.25-7.28 (m, 11H), 7.13-7.21 (m, 9H), 6.97-7.04 (m, 6H), 6.89-6.97 (m, 10H), 6.01 (s, 7H), 4.03 ppm(s, 7H) |
| BA-05 | 1H NMR (CHLOROFORM-d, 400 MHz): d = 7.56 (d, J = 1.5 Hz, 2H), 7.30-7.38 (m, 6H), 7.25-7.30 (m, 9H), 7.05 (s, 4H), 6.90 (s, 6H), 6.01 (s, 4H), 5.91 (s, 2H), 5.29-5.31 ppm(m, 3H) |
| BA-07 | 1 H NMR (CHLOROFORM-d, 400 MHz): d = 7.80 (s, 7H), 7.59 (s, 3H), 7.35 (s, 2H), 7.26 (s, 4H), 7.22 (d, J = 1 .6 Hz, 3H), 7.17 (dd, J = 8.4, 5.4 Hz, 5H), 7.00 (t, J = 8.7 Hz, 5H), 4.05 (s, 5H), 2.73 (br. s., 11H), 1.25 ppm (s, 4H) |
| BA-08 | 1H NMR (CHLOROFORM-d, 400 MHz): d = 7.42 (s, 1H), 7.26 (d, J = 0.7 Hz, 7H), 7.28 (s, 2H), 7.15 (dt, J = 2.3, 1.2 Hz, 3H), 6.89 (d, J = 8.1 Hz, 2H), 6.08 (d, J = 1.7 Hz, 1H), 6.00 (d, J = 0.7 Hz, 3H), 5.16 (s, 3H), 4.07 (s, 3H), 3.75 (d, J = 0.7 Hz, 5H), 1.57 (s, 15H), 0.00 ppm (s, 5H) |
| BA-09 | 1H NMR (DMSO-d6, 400 MHz): d = 7.86 (d, J = 2.1 Hz, 4H), 7.60 (s, 4H), 7.46 (d, J = 1.6 Hz, 4H), 7.27 (s, 8H), 7.09 (d, J = 1.5 Hz, 5H), 7.00-7.06 (m, 4H), 6.27 (t, J = 1.9 Hz, 4H), 6.07 (s, 8H), 5.37 ppm (s, 8H) |
| BA-10 | 1H NMR (CHLOROFORM-d, 400 MHz): d = 8.65-8.68 (m, 2H), 8.18-8.22 (m, 3H), 8.07 (dd, J = 7.7, 0.8 Hz, 3H), 7.52-7.63 (m, 5H), 7.47 (d, J = 2.3 Hz, 5H), 7.21-7.32 (m, 6H), 6.28-6.33 (m, 2H), 5.42 (s, 5H), 5.30 (s, 4H), 1.60 (s, 13H), 0.00 ppm (s, 3H) |
| BA-11 | 1H NMR (400 MHz, DMSO-d6) 8.32 (dd, J = 8.3, 1.5 Hz, 1H), 8.21 (d, J = 1.5 Hz, 2H), 7.39 (dd, J = 8.4, 5.7 Hz, 2H), 6.95-7.22 (m, 3H), 6.11 (s, 2H), 4.20 (s, 2H) |
| BA-12 | 1H NMR (DMSO-d6, 400 MHz): d = 8.23 (s, 4H), 7.87 (s, 4H), 7.62 (s, 7H), 7.46 (s, 4H), 7.34 (s, 3H), 6.26 (s, 3H), 5.39 (s, 7H), 2.64 ppm (s, 11H) |
| BA-13 | 1H NMR (CHLOROFORM-d, 400 MHz): d = 7.88 (t, J = 1.7 Hz, 3H), 7.62-7.67 (m, 3H), 7.44-7.50 (m, 3H), 7.25-7.37 (m, 8H), 7.14-7.22 (m, 8H), 6.95-7.02 (m, 5H), 5.23-5.34 (m, 6H), 4.02 (s, 6H), 1 .57 (s, 6H), 1.19-1.30 (m, 2H), 0.00 ppm (s, 1H) |
| BA-14 | 1H NMR (DMSO-d6, 400 MHz): d = 7.86 (s, 4H), 7.64 (s, 5H), 7.46 (s, 9H), 7.40 (s, 7H), 7.30 (d, J = 1.6 Hz, 7H), 6.27 (t, J = 2.0 Hz, 4H), 5.76 (s, 6H), 5.39 ppm (s, 7H) |
| BA-15 | (DMSO-d6, 400 MHz), 3.81 (s, 2H), 4.84 (bs, 2H), 6.49 (d, J = 8.4 Hz, 2H), 6.89(d, J = 8.4 Hz, 2H), 7.21 (s, 1H), 7.37 (bs, 2H), 7.68 (t, J = 8.4 Hz, 1H), 7.89 (d, J = 8 Hz, 1H), 8.15 (m, 1H), 8.23 (dd, 1H), 8.26 (s, 1H) |
| BA-16 | 1H NMR (DMSO-d6, 400 MHz): 10.13 (br s, 2H), 7.82 (br s, 1H), 7.64 (d, J = 7.2 Hz, 1H), 7.53 (s, 1H), 7.4-7.5 (m, 3H), 7.36 (d, J = 8.4 Hz, 2H), 7.3 (d, J = 8.4 Hz, 2H), 4.48 (br s, 2H), 4.03 (s, 2H); |
| BA-18 | 1H NMR(DMSO-d6, 400 MHz): d = 9.58 (s, 2H), 7.82 (s, 1H), 7.53 (s, 4H), 7.45 (s, 2H), 7.23-7.27 (m, 5H), 7.12 (d, J = 8.5 Hz, 3H), 3.95 (s, 3H), 3.57 (br. s., 24H), 2.93 (s, 5H), 0.00 ppm (s, 2H) |
| BA-19 | 1H NMR (DMSO-d6, 400 MHz): 9.62 (s, 1H), 7.76 (br s, 2H), 7.59 (d, J = 7.2 Hz, 1H), 7.53 (s, 1H), 7.4-7.5 (m, 3H), 7.22 (d, J = 8.4 Hz, 2H), 7.14 (d, J = 8.4 Hz, 2H), 3.95 (s, 2H), 2.94 (s, 3H); |

-continued

| CmpdNo | NMR |
|---|---|
| BA-20 | (DMSO-d6, 400 MHz), 3.05 (s, 3H), 4.82 (s, 2H), 6.68 (d, J = 8.4 Hz, 2H), 7.14 (d, J = 8.4 Hz, 2H), 7.2 (s, 1H), 7.25 (s, 1H), 7.39 (d, J = 8 Hz, 1H), 7.47 (t, J = 8.4 Hz, 1H), 7.64 (bs, 2H), 7.8 (d, J = 8 Hz, 1H), 8.06 (s, 1H), 9.56 (s, 1H) |
| BA-21 | 1H NMR (DMSO-d6, 400 MHz): 8.46 (s, 1H), 7.69 (br s, 2H), 7.55 (d, J = 7.2 Hz, 1H), 7.53 (s, 1H), 7.4-7.5 (m, 4H), 7.31 (d, J = 8.4 Hz, 2H), 7.09 (d, J = 8.4 Hz, 2H), 3.9 (s, 2H); |
| BA-22 | 1H NMR (DMSO-d6, 400 MHz): d = 8.13 (s, 1H), 7.99 (d, J = 7.6 Hz, 1H), 7.50-7.63 (m, 4H), 6.97-7.09 (m, J = 8.2 Hz, 2H), 6.52-6.61 (m, J = 8.2 Hz, 2H), 4.94 (s, 2H), 3.99 (s, 2H), 2.68-2.69 (m, 3H), 2.69 ppm (s, 3H) |
| BA-23 | 1H NMR (DMSO-d6, 400 MHz): 9.42 (s, 1H), 8.18 (d, J = 6.8 Hz, 1H), 7.65 (s, 1H), 7.5-7.59 (m, 3H), 7.33 (d, J = 8.4 Hz, 2H), 7.16 (d, J = 8.4 Hz, 2H), 4.16 (s, 2H); |
| BA-24 | (DMSO-d6, 400 MHz), 2.63 (s, 3H), 4.02 (s, 2H), 5.78 (s, 2H), 7.16 (d, J = 8.4 Hz, 2H), 7.29 (d, J = 8.4 Hz, 2H), 7.44-7.47 (m, 1H), 7.51-7.55 (s, 3H), 7.93 (d, J = 8 Hz, 1H), 8.07 (d, J = 2Hz, 1H), 8.41 (s, 1H) |
| BA-25 | 1H NMR (METHANOL-d4, 400 MHz): d = 9.19 (s, 3H), 7.95 (s, 3H), 7.79 (s, 3H), 7.66 (s, 3H), 7.40-7.51 (m, 14H), 7.34 (d, J = 8.3 Hz, 7H), 4.26 ppm (s, 6H) |
| BA-26 | 1H NMR (DMSO-d6, 400 MHz): d = 7.79 (s, 3H), 7.59 (s, 3H), 7.40 (s, 13H), 7.29 (d, J = 8.2 Hz, 10H), 4.03 (s, 6H), 3.25 (s, 4H), 1.03 ppm (s, 4H) |
| BA-27 | 1H NMR (METHANOL-d4, 400 MHz): d = 7.52 (s, 5H), 7.32 (s, 4H), 7.17 (s, 3H), 4.05 (s, 3H), 2.66 ppm (br. s., 19H) |
| BA-28 | 1 H NMR (acetone, 400 MHz): d = 9.23 (s, 1H), 7.98 (d, J = 1 .6 Hz, 3H), 7.97 (br. s., 1H), 7.82 (s, 1H), 7.81 (t, J = 1.3 Hz, 1H), 7.62 (d, J = 1.5 Hz, 1H), 7.40-7.52 (m, 6H), 7.20 (d, J = 8.5 Hz, 3H), 5.36 (br. s., 3H), 4.15 (s, 3H), 2.81 (s, 8H), 2.09 (s, 1H), 2.05 (dt, J = 4.4, 2.2 Hz, 17H), 1.29 ppm (s, 1H) |
| BA-29 | 1H NMR (DMSO-d6, 400 MHz): 8.31 (s, 1H), 7.65 (s, 2H), 7.54 (d, J = 7.2 Hz, 1H), 7.52 (s, 1H), 7.4-7.48 (m, 3H), 7.29 (d, J = 8.4 Hz, 2H), 7.09 (d, J = 8.4 Hz, 2H), 6.0-6.05 (m, 1H), 3.89 (s, 2H), 3.2-3.6 (m, 2H), 1.03 (t, J = 7.24 Hz, 3H); |
| BA-30 | 1H NMR (DMSO-d6, 400 MHz): 10.59 (s, 1H), 9.41 (s, 1H), 7.17 (d, J = 6.8 Hz, 1H), 7.67 (s, 1H), 7.64 (d, J = 8.8 Hz, 1H), 7.5-7.6 (m, 3H), 7.3 (d, J = 8.4 Hz, 2H), 4.15 (s, 2H), 3.82 (q, J = 6.8 Hz, 2H), 0.98 (t, J = 6.8 Hz, 3H); |
| BA-31 | (CDCl3, 400 MHz), 2.57 (t, 6H), 3.45 (t, 6H), 3.78 (s, 2H), 4.44 (bs, 2H), 7.41-7.47(m, 2H), 7.55-7.57 (m, 1H), 7.66 (d, 2H), 8 (d, J = 6.4 Hz, 1H), 9.02 (s, 1H) |
| BA-32 | (DMSO-d6, 400 MHz), 4.05 (bs, 2H), 6.85 (d, J = 8.4 Hz, 1H), 7.18 (d, J = 8.4 Hz, 1H), 7.26 (d, J = 7.2Hz, 1H), 7.29 (s, 1H), 7.37-7.45 (m, 3H), 7.47 (t, J = 8.4 Hz, 1H), 7.65 (bs, 2H), 7.9 (d, J = 7.2 Hz, 1H), 8.13 (s, 1H) |
| BA-33 | 1H NMR (DMSO-d6, 400 MHz): 10.4 (br s, 1H), 9.43 (s, 1H), 8.18 (d, J = 2.0 Hz, 1H), 8.16 (d, J = 7.2 Hz, 1H), 7.92 (d, J = 8.4 Hz, 1H), 7.75 (br s, 1H), 7.67 (s, 1H), 7.5-7.6 (m, 3H), 7.34 (d, J = 8.8 Hz, 1H), 4.17 (s, 2H), 3.15-3.24 (m, 2H), 1.09 (t, J = 7.2 Hz, 3H); |
| BA-38 | 1H NMR (DMSO-d6, 400 MHz): 9.41 (s, 1H), 8.14 (d, J = 4.4 Hz, 1H), 8.14 (s, 1H), 7.67 (s, 1H), 7.63 (dd, J = 8.4, 2.4 Hz, 1H), 7.5-7.59 (m, 3H), 6.78 (d, J = 8.48 Hz, 1H), 4.11 (s, 2H), 3.82 (s, 3H); |
| BA-39 | $^1$H NMR (400 MHz, CDCl$_3$): 8.98 (s, 1 H), 7.68 (d, J = 6.8 Hz, 1H), 7.6 (s, 1H), 7.67 (s, 1H), 7.56 (dd, J = 7.2, 1.2 Hz, 1H), 7.38-7.46 (m, 2H), 7.2 (t, J = 8.0 Hz, 1H), 6.86(d, J = 7.6 Hz, 1H), 6.7-6.76 (m, 2H), 5.3 (s, 1H), 4.13(s, 2H); |
| BA-40 | 1H NMR (DMSO-d6, 400 MHz): 10.04 (s, 1H), 9.41 (s, 1H), 8.23 (d, J = 2.4 Hz, 1H), 8.15 (d, J = 7.2 Hz, 1H), 7.76 (d, J = 8.8 Hz, 1H), 7.64-7.69 (m, 2H), 7.5-7.58 (m, 3H), 4.13 (s, 2H), 4.09-4.1 6 (q, J = 7.2 Hz, 2H), 1.22 (t, J = 7.2 Hz, 3H); |
| BA-43 | (CDCl3, 400 MHz), 2.57 (t, 6H), 3.68-3.75 (overlap, 8H), 7.41-7.47(m, 2H), 7.55-7.57 (m, 1H), 7.66 (d, 2H), 8.01 (d, J = 6.4 Hz, 1H), 9.02 (s, 1H) |
| BA-44 | (CDCl3, 400 MHz), 2.53-2.57 (m, 4H), 3.5 (t, 2H), 3.66 (t, 2H), 3.78 (s, 3H), 7.41-7.47(m, 2H), 7.55-7.58 (m, 1H), 7.66 (d, 1H), 8.0 (d, J = 6.4 Hz, 1H), 9.02 (s, 1H) |
| BA-45 | (DMSO-d6, 400 MHz), 1.13 (t, 3H), 1.69-1.97 (m, 4H), 3.15 (t, 2H), 3.48 (t, 2H), 3.98 (m, 3H), 4.48 (d, 2H), 7.32(d, 1H), 7.55-7.62 (m, 2H), 7.73 (s, 1H), 8.47 (d, J = 6.4 Hz, 1H), 9.57 (s, 1H), 10.02 (bs, 1H) |
| BA-46 | (CDCl3, 400 MHz), 1.45-1.55 (m, 2H), 1.98 (d, 2H), 2.25-2.31 (t, 2H), 2.9 (d, 2H), 3.58-3.6 (m, 1H), 3.74 (s, 2H), 4.27 (s, 2H), 4.36 (d, 1H), 7.39-7.47(m, 2H), 7.55-7.57 (m, 1H), 7.66 (d, 1H), 7.98 (d, J = 6.4 Hz, 1H), 9.01 (s, 1H) |
| BA-47 | (CDCl3, 400 MHz), 1.46-1.56 (m, 2H), 1.87 (d, 2H), 2.16-2.21 (overlap, 4H), 2.77 (m, 1H), 2.93 (d, 2H), 3.74 (s, 2H), 7.39-7.46(m, 2H), 7.54-7.57 (m, 1H), 7.66 (d, J = 1.6 Hz, 1H), 8.01 (d, J = 6.4 Hz, 1H), 9 (s, 1H) |
| BA-48 | (CDCl3, 400 MHz), 2.55 (t, 4H), 2.94 (t, 4H), 3.75 (s, 2H), 7.39-7.47(m, 2H), 7.55-7.57 (m, 2H), 7.66 (d, 1H), 8.01 (d, J = 6.4 Hz, 1H), 9.01 (s, 1H) |
| BA-49 | (CDCl3, 400 MHz), 1.25 (t, 3H), 2.53 (t, 4H), 3.52 (t, 4H), 3.77 (s, 2H), 4.14 (q, 2H), 7.41-7.47(m, 2H), 7.55-7.57 (m, 1H), 7.66 (d, 1H), 8(d, J = 6.4 Hz, 1H), 9.02 (s, 1H) |
| BA-50 | (CDCl3, 400 MHz), 2.31 (s, 3H), 2.51 (t, 4H), 2.61 (t, 4H), 3.77 (s, 2H), 7.39-7.46(m, 2H), 7.54-7.57 (m, 1H), 7.66 (d, 1H), 8 (d, J = 6.4 Hz, 1H), 9.01 (s, 1H) |
| BA-51 | 1H NMR (DMSO-d6, 400 MHz): 9.39 (s, 1H), 8.45 (s, 1H), 8.1 (d, J = 7.2 Hz, 1H), 7.66 (s, 1H), 7.5-7.59 (m, 4H), 7.32 (d, J = 8.5 Hz, 2H), 7.14 (d, J = 8.5 Hz, 2H), 5.77 (s, 2H), 4.06 ppm (s, 2H); |
| BA-52 | 1H NMR (DMSO-d6, 400 MHz): 10.78 (s, 1H), 9.58 (s, 1H), 8.52 (d, J = 6.8 Hz, 1 H, 7.75 (s, 1H), 7.54-7.68 (m, 3H), 6.73 (s, 1H), 4.55 (s, 2H), 3.47 (m, 2H), 3.0-3.2 (m, 6H), 1.01 ppm (t, J = 7.2 Hz, 3H); |

Methods of the invention parallel the compositions and formulations. The methods comprise administering to a patient in need of treatment a therapeutically effective amount of a compound according to the invention. The present invention also provides a method for inhibiting phosphodiesterase 4.

In-vitro assay for PDE4 enzymes. The in-vitro activity of PDE4 enzymes and the in-vitro potency of therapeutic agents described in the present invention was measured using a real-time, enzyme-coupled spectrophotometric assay. By using three different coupling enzymes, the product of the PDE4 reaction is coupled to the oxidation of the reduced form β-nicotinamide adenine dinucleotide (NADH), which dissipation can be monitored spectrophotmetrically at 340 nM.

Assay description. Buffer A containing 50 mM Tris, pH 8.0, 16 mM $MgCl_2$ and 80 mM KCl is prepared and stored at room temperature. Buffer B containing 50 mM Tris, pH 8.0 is prepared and stored at toom temperature. Stock solutions of the following reagents are prepared in Buffer B and stored at −20° C.: Adenosine-5'-triphosphate (ATP), cyclic adenosine-5'-monophosphate (cAMP), phosphoenolpyruvate (PEP) and NADH. An assay mix is prepared by mixing Buffer A, trichloroethylphosphine (TCEP), ATP, PEP, NADH, myokinase (MK), pyruvate kinase (PK), lactate dehydroganese (LDH) and PDE4 to a final volume of 20 mL, which is enough for a single 96-well assay plate. Assay mix (180 μL) and test article (10 μL) in 1:1 DMSO/$H_2O$ mixture is pre-incubated at room temperature for 10 min. The enzymatic reaction is initiated by addition of cAMP (10 μL). Final concentration of all components in the assay (200 μL/well) are as follows: 10 mM $MgCl_2$, 50 mM KCl, 5 mM TCEP, 2.5% DMSO, 0.4 mM NADH, 1 mM PEP, 0.04 mM ATP, 5 units MK, 1 unit PK, 1 unit LDH and appropriate amount of PDE4. Reaction progress curves are monitored in a plate reader capable of measuring light absorbance at 340 nM. A decrease in light absorbance at 340 nm is due to oxidation of NADH. Positive controls containing no test article and negative controls containing no test article and no cAMP are included on every assay plate. Reaction rates are determined from the slopes of the linear portions of the progress curves. All data is percent normalized with respect to controls and presented as percent inhibition.

The results of testing of representative species are shown below:

TABLE 3

| Example No | Synthetic Method | h4D7<br>A < 1 uM, B1-10 uM,<br>C = 10-20 uM,<br>D > 30 uM | h4B1<br>A < 1 uM, B1-10 uM,<br>C = 10-20 uM,<br>D > 30 uM |
|---|---|---|---|
| 1 | A | A | B |
| 2 | Etc. | A | A |
| 3 |  | A | B |
| 4 |  | A | B |
| 5 |  | B | ND |
| 6 |  | B | C |
| 7 |  | A | B |
| 8 |  | A | B |
| 9 |  | B | B |
| 11 |  | A | B |
| 10 |  | A | C |
| 12 |  | A | B |
| 13 |  | A | B |
| 14 |  | A | B |
| 15 |  | A | A |
| 16 |  | A | ND |
| 17 |  | B | B |
| 18 |  | A | B |
| 19 |  | B | B |
| 20 |  | A | B |
| 21 |  | A | A |
| 22 |  | A | A |
| 27 |  | A | A |
| 23 |  | A | A |
| 24 |  | A | A |
| 25 |  | A | A |
| 26 |  | A | A |
| 28 |  | A | A |
| 30 |  | A | A |
| 37 |  | A | B |

TABLE 3-continued

| Example No | Synthetic Method | h4D7<br>A < 1 uM, B1-10 uM,<br>C = 10-20 uM,<br>D > 30 uM | h4B1<br>A < 1 uM, B1-10 uM,<br>C = 10-20 uM,<br>D > 30 uM |
|---|---|---|---|
| 31 |  | A | A |
| 32 |  | A | A |
| 33 |  | A | A |
| 34 |  | A | A |
| 35 |  | A | A |
| 38 |  | A | B |
| 39 |  | A | B |
| 40 |  | A | D |
| 41 |  | B | C |
| 42 |  | B | C |
| 44 |  | B | C |
| 45 |  | A | B |
| 46 |  | B | ND |
| 36 |  | A | A |
| 47 |  | B | ND |

The activity of PDE4 inhibitors described in the present invention was also measured using in an ex-vivo assay measuring leukotriene E4 (LTE4) in human whole blood after Sephadex stimulation. The anti-inflammatory activity of therapeutic agents of the present invention is demonstrated by the inhibition of eosinophil activation as measured by sephadex bead stimulated LTE4 production in whole human blood. For each sample, 356 μl of heparinized human whole blood (Vacutainer tube #6480) is added to wells of a 96 well plate. Then, 4 μl of a series of compound dilutions (in DMSO) are added in triplicates, suspension mixed and allowed to incubate at 37° C. for 15 min with gentle shaking. After that, blood samples are stimulated by adding 40 μL of Sephadex G-15 beads (Sigma-Aldrich, Sweden). The beads are predissolved in PBS (0.16 g/mL PBS). After mixing, the suspension is incubated at 37° C. for 90 min. Then, 8 μL of 15% EDTA/PBS is added to each sample, mixed and plate centrifuged for 5 min at 115×g at 21° C. and supernatants taken. In each plate, 10 positive controls and 10 negative controls are used, containing DMSO instead of compound solution. The positive controls are stimulated with Sephadex as described for the samples, and in the negative controls (unstimulated), Sephadex solution is replaced by PBS. $LTE_4$ levels in the resulting plasma samples are determined using a commercial enzyme-linked immunoassay (Cayman Chemical Company, Ann Arbor, Mich.) according to the manufacturer's instructions. Tables 4 and 5 provide data for some representative examples:

TABLE 4

| IC50 for human PDE4D isozyme<br>A < 5 uM, B = 5-20 uM, C = 20-40 uM | |
|---|---|
| CmpdNo | hPDE4D |
| BA-01 | A |
| BA-02 | A |
| BA-03 | A |
| BA-04 | A |
| BA-05 | A |
| BA-06 | A |
| BA-07 | A |
| BA-08 | A |
| BA-09 | A |
| BA-10 | A |
| BA-11 | A |
| BA-12 | A |
| BA-13 | A |
| BA-14 | A |
| BA-15 | A |
| BA-16 | A |

TABLE 4-continued

IC50 for human PDE4D isozyme
A < 5 uM, B = 5-20 uM, C = 20-40 uM

| CmpdNo | hPDE4D |
|---|---|
| BA-18 | A |
| BA-19 | A |
| BA-20 | A |
| BA-21 | A |
| BA-22 | A |
| BA-23 | A |
| BA-24 | A |
| BA-25 | A |
| BA-26 | A |
| BA-27 | A |
| BA-28 | A |
| BA-29 | A |
| BA-30 | A |
| BA-31 | A |
| BA-32 | A |
| BA-33 | A |
| BA-38 | A |
| BA-39 | A |
| BA-40 | A |
| BA-43 | A |
| BA-44 | A |
| BA-45 | A |
| BA-46 | A |
| BA-47 | A |
| BA-48 | A |
| BA-49 | A |
| BA-50 | A |
| BA-51 | A |
| BA-52 | A |
| BA-53 | A |
| BA-54 | A |
| BA-55 | A |
| BA-57 | A |
| BA-58 | A |
| BA-59 | A |
| BA-60 | A |
| BA-61 | A |
| BA-63 | A |
| BA-64 | A |
| BA-66 | A |
| BA-67 | A |
| BA-71 | A |
| BA-72 | A |
| BA-73 | A |
| BA-74 | A |
| BA-75 | A |

TABLE 5

IC50 for human PDE4B isozyme
A < 5 uM, B = 5-20 uM, C = 20-40 uM

| CmpdNo | hPDE4B |
|---|---|
| BA-01 | A |
| BA-02 | A |
| BA-03 | A |
| BA-04 | A |
| BA-05 | A |
| BA-06 | A |
| BA-07 | A |
| BA-08 | A |
| BA-09 | A |
| BA-10 | A |
| BA-11 | A |
| BA-12 | A |
| BA-13 | A |
| BA-14 | A |
| BA-15 | A |
| BA-16 | A |
| BA-18 | B |
| BA-19 | B |

TABLE 5-continued

IC50 for human PDE4B isozyme
A < 5 uM, B = 5-20 uM, C = 20-40 uM

| CmpdNo | hPDE4B |
|---|---|
| BA-20 | A |
| BA-21 | A |
| BA-22 | A |
| BA-23 | A |
| BA-24 | A |
| BA-25 | A |
| BA-26 | A |
| BA-27 | A |
| BA-28 | A |
| BA-29 | A |
| BA-30 | A |
| BA-31 | A |
| BA-32 | A |
| BA-33 | A |
| BA-38 | A |
| BA-39 | A |
| BA-40 | A |
| BA-43 | A |
| BA-44 | B |
| BA-45 | B |
| BA-46 | B |
| BA-47 | B |
| BA-48 | B |
| BA-49 | A |
| BA-51 | A |
| BA-52 | C |
| BA-53 | A |
| BA-54 | A |
| BA-55 | A |
| BA-58 | A |
| BA-59 | C |
| BA-60 | A |
| BA-61 | A |
| BA-63 | A |
| BA-64 | A |
| BA-67 | A |
| BA-71 | A |
| BA-72 | A |
| BA-73 | A |
| BA-74 | A |
| BA-75 | A |

Persons of skill in the art accept that positive results in PDE4 models are predictive of therapeutic utility as discussed above.

We claim:

1. A compound of formula I:

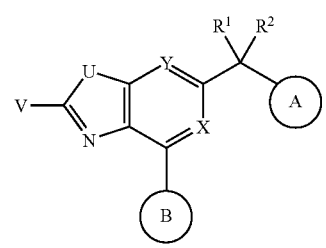

or a pharmaceutically acceptable salt thereof wherein
U is selected from the group consisting of —S— and —O—;
V is selected from the group consisting of H, $CH_3$, $NH_2$, and $CF_3$;
X is selected from the group consisting of CH, C—F, C—Cl, C—Br, C—I, C—$NH_2$, C—OH, C—$OCH_3$, N, and N—O;

Y is selected from the group consisting of N, CH, CF and C-lower alkyl;
$R^1$ is H or lower alkyl;
$R^2$ is selected from the group consisting of H, alkyl, OH, $NH_2$, and $OCH_3$;
B is an optionally substituted, mono- or bicyclic aryl or heteroaryl; and
A is an optionally substituted heterocycle or an optionally substituted carbocycle.

2. A compound or salt according to claim 1 wherein Y is N.

3. A compound or pharmaceutically acceptable salt according to claim 1 wherein Y is CH.

4. A compound or pharmaceutically acceptable salt according to claim 1 wherein U is S.

5. A compound or pharmaceutically acceptable salt according to claim 1 wherein U is O.

6. A compound or pharmaceutically acceptable salt according to claim 1 wherein V is selected from H, $CH_3$ and $NH_2$.

7. A compound or pharmaceutically acceptable salt according to claim 1 wherein B is phenyl which has a substituent at the 3-position, the 4-position or at both the 3- and 4-positions.

8. A compound or pharmaceutically acceptable salt according to claim 7 wherein B is selected from 3-chlorophenyl, 3-nitrophenyl, 3-cyanophenyl, 3-bromophenyl, 3-acetylphenyl, 3-trifluoromethylphenyl, and 3-methylthiophenyl.

9. A compound or pharmaceutically acceptable salt according to claim 1 wherein B is benzo[c][1,2,5]oxadiazol-5-yl or benzo[d][1,3]dioxol-5-yl.

10. A compound or pharmaceutically acceptable salt according to claim 1 wherein $R^1$ is H and $R^2$ is chosen from H and OH.

11. A compound or pharmaceutically acceptable salt according to claim 1 wherein A is optionally substituted phenyl.

12. A compound or pharmaceutically acceptable salt according to claim 1 wherein A is selected from the group consisting of optionally substituted 5- and 6-membered ring nitrogen heterocycles.

13. A compound or pharmaceutically acceptable salt according to claim 12 wherein A is selected from the group consisting of optionally substituted pyridinyl, morpholin-4-yl, piperazin-1-yl, piperidiny-1-yl, imidazol-1-yl, pyrazol-1-yl, and pyrazol-5-yl.

14. A compound or pharmaceutically acceptable salt according to claim 1 wherein X is selected from the group consisting of CH, C—F, C—OH and N.

15. A compound or pharmaceutically acceptable salt according to claim 1 wherein
X is selected from the group consisting of CH, C—F, C—OH and N;
Y is N or CH;
U is O;
V is selected from H, $CH_3$ and $NH_2$;
B is benzo[c][1,2,5]oxadiazol-5-yl or phenyl which has a substituent at the 3-position, the 4-position or at both the 3- and 4-positions;
$R^1$ is H;
$R^2$ is chosen from H and OH; and
A is selected from the group consisting of optionally substituted phenyl and optionally substituted 5- and 6-membered ring nitrogen heterocycles.

16. A compound or pharmaceutically acceptable salt according to claim 1 wherein

X is selected from the group consisting of CH, C—F, C—OH and N;
Y is N or CH;
U is S;
V is selected from H, $CH_3$ and $NH_2$;
B is benzo[c][1,2,5]oxadiazol-5-yl or phenyl which has a substituent at the 3-position, the 4-position or at both the 3- and 4-positions;
$R^1$ is H;
$R^2$ is chosen from H and OH; and
A is selected from the group consisting of optionally substituted phenyl and optionally substituted 5- and 6-membered ring nitrogen heterocycles.

17. A compound or pharmaceutically acceptable salt according to claim 14 wherein B is selected from benzo[d][1,3]dioxol-5-yl, 3-chlorophenyl, 3-nitrophenyl, 3-cyanophenyl, 3-bromophenyl, 3-acetylphenyl, 3-trifluoromethylphenyl, and 3-methylthiophenyl.

18. A compound or pharmaceutically acceptable salt according to claim 17 wherein A is selected from the group consisting of optionally substituted pyridinyl, morpholin-4-yl, piperazin-1-yl, piperidiny-1-yl, imidazol-1-yl, pyrazol-1-yl, and pyrazol-5-yl.

19. A compound or pharmaceutically acceptable salt according to claim 1 of formula

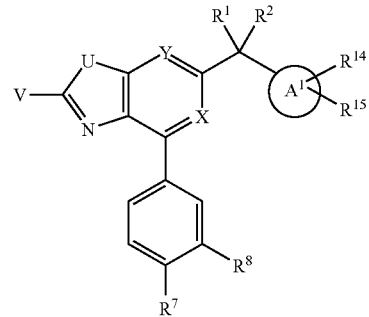

wherein
$A^1$ is phenyl, five-membered heteroaryl, six-membered heteroaryl, 4-7 membered non-aryl heterocycle or fused bicycle;
$R^7$ is H or F;
$R^8$ is chosen from halogen, nitro, acetyl, hydroxyethyl, amino, methylthio, trifluoromethyl, methoxymethyl, methoxycarbonyl, trifluoromethoxy, cyano and 1,3,4-thiadiazol-2-yl, or taken together $R^7$ and $R^8$ are methylenedioxy, =N—O—N=, —NH—CH=N— or difluoromethylenedioxy;
$R^{14}$ is chosen from H, halogen, haloalkyl, alkyl, acyl, alkoxyalkyl, hydroxyalkyl, carbonyl, phenyl, heteroaryl, benzenesulfonyl, hydroxy, alkoxy, haloalkoxy, oxaalkyl, carboxy, alkoxycarbonyl, alkoxycarbonylalkyl, alkoxycarbonylamino, carboxyalkyl, alkoxycarbonylaminoalkyl, carboxyalkylcarbonylamino, carboxamido, aminocarbonyloxy, alkylaminocarbonyl, dialkylaminocarbonyl, aminocarbonylalkyl, cyano, acetoxy, nitro, amino, alkylamino, dialkylamino, aminoalkyl, (alkyl)(aryl)aminoalkyl, alkylaminoalkyl, dialkylaminoalkyl, dialkylaminoalkoxy, alkyl(hydroxyalkyl)amino, heterocyclylalkoxy, mercapto, alkylthio, alkylsulfonyl, alkylsulfonylamino, alkylsulfinyl, alkylsulfonyl, arylthio, arylsulfonyl, arylsulfonylamino, arylsulfinyl, arylsulfonyl, acylaminoalkyl, acylaminoalkoxy, acylamino, amidino, aryl, benzyl, heterocyclyl, heterocyclylalkyl, phenoxy, benzyloxy, heteroaryloxy, heterocyclylamino, hydroxyimino, alkoxyimino, oxaalkyl, aminosulfonyl, trityl, amidino, guanidino, ureido, —NHC(=O)NHalkyl, —NHC(=O)NH-heterocyclyl, -alkyl-NHC(=O)N(alkyl)$_2$, heterocyclylalkylcarbonylamino, benzyloxyphenyl, benzyloxy, the residues of amino acids, amino acid amides, protected residues of aminoacids, protected residues of amino acid amides, N-methylated amino acids and N-methylated amino acid amides;

$R^{15}$ is chosen from H, NO$_2$, OH, NH$_2$, and —NHSO$_2$NH$_2$; or $R^{15}$ together with $R^{14}$ forms methylene dioxy.

20. A compound or pharmaceutically acceptable salt according to claim 1 of formula

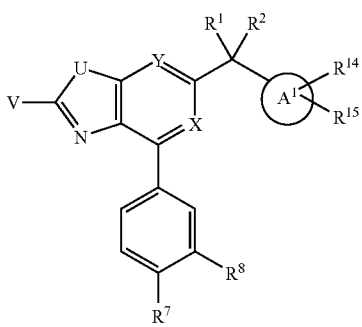

wherein
A$^1$ is phenyl, five-membered heteroaryl, six-membered heteroaryl, 4-7 membered non-aryl heterocycle or fused bicycle;
R$^7$ is H or F;
R$^8$ is chosen from halogen, nitro, acetyl, hydroxyethyl, amino, methylthio, trifluoromethyl, methoxymethyl, methoxycarbonyl, trifluoromethoxy, cyano and 1,3,4-thiadiazol-2-yl, or taken together R$^7$ and R$^8$ are methylenedioxy, =N—O—N=, —NH—CH=N— or difluoromethylenedioxy;
R$^{14}$ is chosen from H, —CH$_3$, —CH$_2$CF$_3$, —CF$_3$, —CHO, —COOH, —CN, halogen, —OH,, —OEt, —C(=O)NH$_2$, —C(=O)NHEt, —C(=O)NMe$_2$ —COOCH$_3$, —COOEt, —CH$_2$NHC(=O)NH$_2$, —CH(CH$_3$)NHC(=O)NH$_2$, —CH$_2$NHC(=O)H, —CH$_2$NHC(=O)CH$_3$, —CH$_2$C(=O)NH$_2$, —CH$_2$COOH, —CH$_2$COOEt, —CH$_2$NHC(=O)OEt, —CH$_2$NHC(=O)O—C$_6$H$_5$, —CH$_2$NHC(=O)C(=O)NH$_2$, —CH$_2$NHC(=O)NHEt, —C(CH$_3$)$_2$OH, —CH$_2$NHC(=O)N(CH$_3$)$_2$, —CH$_2$NHC(=O)NHCH$_3$, —CH$_2$NH$_2$, —CH(CH$_3$)NH$_2$, —C(CH$_3$)$_2$NH$_2$, —CH$_2$OH, —CH$_2$CH$_2$OH, —CH$_2$NHSO$_2$CH$_3$, —CH$_2$OC(=O)NHEt, —OCH$_3$, —OC(=O)NH$_2$, —OCH$_2$CH$_2$N(CH$_3$)$_2$, —OCH$_2$CH$_2$OCH$_3$, —NHC(=O)NH$_2$, —NHC(=O)NHEt, —NHCH$_3$, —NHEt, —NH(tBoc), —NHCH$_2$COOH, —N(CH$_3$)CH$_2$COOH, —NHC(=O)NHCH$_2$CH$_2$Cl, —NHSO$_2$NH$_2$, —NHEt, —N(CH$_3$)$_2$, —NH$_2$, —NH(CH$_3$)C(=O)NH$_2$, —NHSO$_2$CH$_3$, —N(SO$_2$CH$_3$)$_2$, —NHC(=O)OCH$_3$, —NHC(=O)OtBu, —NHC(=O)CH$_3$, —SO$_2$NH$_2$, —NHC(=O)CH$_2$CH$_2$COOH, —NHC(=O)NHCH$_2$COOH, —CH$_2$NHCHO, —NHC(=O)NHCH$_2$COOEt, —NHC(=O)NH(CH$_2$)$_3$COOEt, —NHC(=O)NH(CH$_2$)$_2$COOEt, —N(CH$_3$)CH$_2$CH$_2$OH, —NHC(=O)OEt, —N(Et)C(=O)OEt, —NHC(=O)NH(CH$_2$)$_2$COOH, —NHC(=O)CH$_2$N(CH$_3$)$_2$, —NHC(=O)NH(CH$_2$)$_3$COOH, —NHC(=O)CH$_2$NH$_2$, —NHC(=O)CH$_2$CH$_2$NH$_2$, —NHC(=O)CH$_2$NH(tBoc),

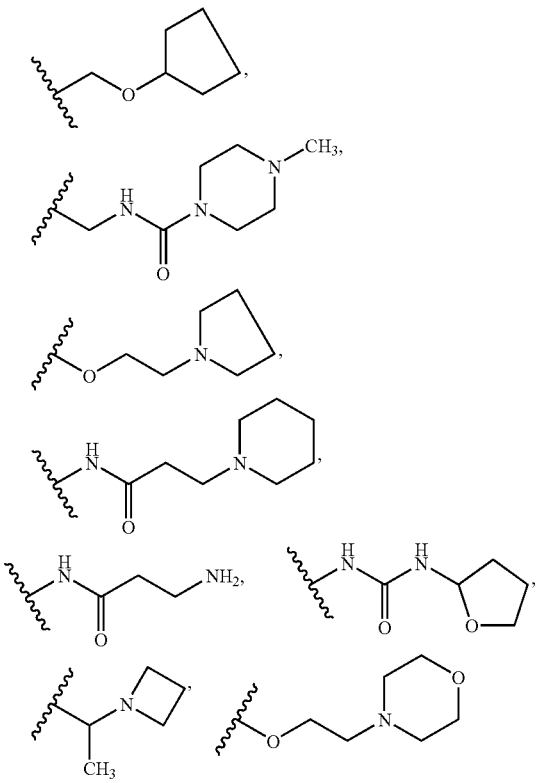

and monocyclic heterocycle substituted with any of the foregoing;
$R^{15}$ is chosen from H, NO$_2$, OH, NH$_2$, and —NHSO$_2$NH$_2$; or
$R^{15}$ together with $R^{14}$ forms methylene dioxy.

21. A pharmaceutical composition comprising a pharmaceutically acceptable carrier and a compound or pharmaceutically acceptable salt according to claim 1.

22. A pharmaceutical composition comprising
(a) a pharmaceutically acceptable carrier;
(b) a compound or pharmaceutically acceptable salt according to claim 1; and
(c) an agent chosen from cholinesterase inhibitors, NMDA antagonists, calpain inhibitors and antioxidants.

23. A pharmaceutical composition according to claim 22 wherein said agent is chosen from tacrine, huperzine, donepezil, lanicemine, remacemide, neramexane, memantine, vitamin E and coenzyme Q10.

24. A method for the treatment of a disease or condition mediated by peripheral phosphodiesterase-4 comprising administering to a mammal in need thereof a therapeutically effective amount of a compound according to claim 1, wherein said disease or condition is chosen from stroke, myocardial infarct, cardiovascular inflammatory conditions, asthma and COPD.

25. A method according to claim 24 wherein said disease or condition is chosen from stroke, myocardial infarct, and cardiovascular inflammatory conditions.

26. A method according to claim 24 wherein said disease or condition is chosen from asthma and COPD.

27. A method for treating or preventing bone loss comprising administering to a mammal in need thereof a therapeutically effective amount of a compound according to claim 1.

28. A method for treating bladder inflammation, bladder overactivity and pain arising from bladder inflammation comprising administering to a mammal in need thereof a therapeutically effective amount of a compound according to claim 1.

* * * * *